(12) United States Patent
Levy et al.

(10) Patent No.: US 10,081,633 B2
(45) Date of Patent: Sep. 25, 2018

(54) ADENYLYL CYCLASE INHIBITORS, PHARMACEUTICAL COMPOSITIONS AND METHOD OF USE THEREOF

(71) Applicants: Daniel E. Levy, San Mateo, CA (US); Patricio Abarzúa, West Caldwell, NJ (US)

(72) Inventors: Daniel E. Levy, San Mateo, CA (US); Patricio Abarzúa, West Caldwell, NJ (US)

( * ) Notice: Subject to any disclaimer, the term of this patent is extended or adjusted under 35 U.S.C. 154(b) by 0 days.

(21) Appl. No.: 15/626,975

(22) Filed: Jun. 19, 2017

(65) Prior Publication Data

US 2017/0362235 A1 Dec. 21, 2017

Related U.S. Application Data

(60) Provisional application No. 62/352,198, filed on Jun. 20, 2016.

(51) Int. Cl.
| | | |
|---|---|---|
| *C07D 473/24* | (2006.01) | |
| *C07D 471/04* | (2006.01) | |
| *C07D 487/04* | (2006.01) | |
| *C07D 473/34* | (2006.01) | |

(52) U.S. Cl.
CPC ......... *C07D 473/34* (2013.01); *C07D 471/04* (2013.01); *C07D 487/04* (2013.01)

(58) Field of Classification Search
CPC ... C07D 471/04; C07D 473/34; C07D 487/04
See application file for complete search history.

(56) References Cited

U.S. PATENT DOCUMENTS

2009/0264383 A1* 10/2009 Hastings .............. A61K 31/416
514/46

* cited by examiner

*Primary Examiner* — Erich A Leeser

(57) ABSTRACT

The present invention relates to novel adenine based inhibitors of adenylyl cyclase of the formula:

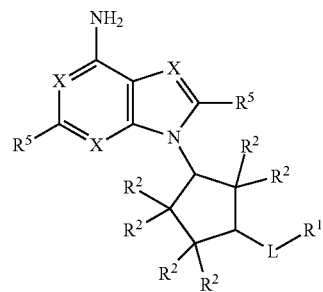

wherein X, L, R1, R2, R5 are those defined herein. Compounds of the present invention are useful to treat cardiovascular diseases. The present invention also relates to a method of preventing heart failure by administering an effective amount of compound according to the invention following vascular injury and reperfusion therapy.

12 Claims, 3 Drawing Sheets

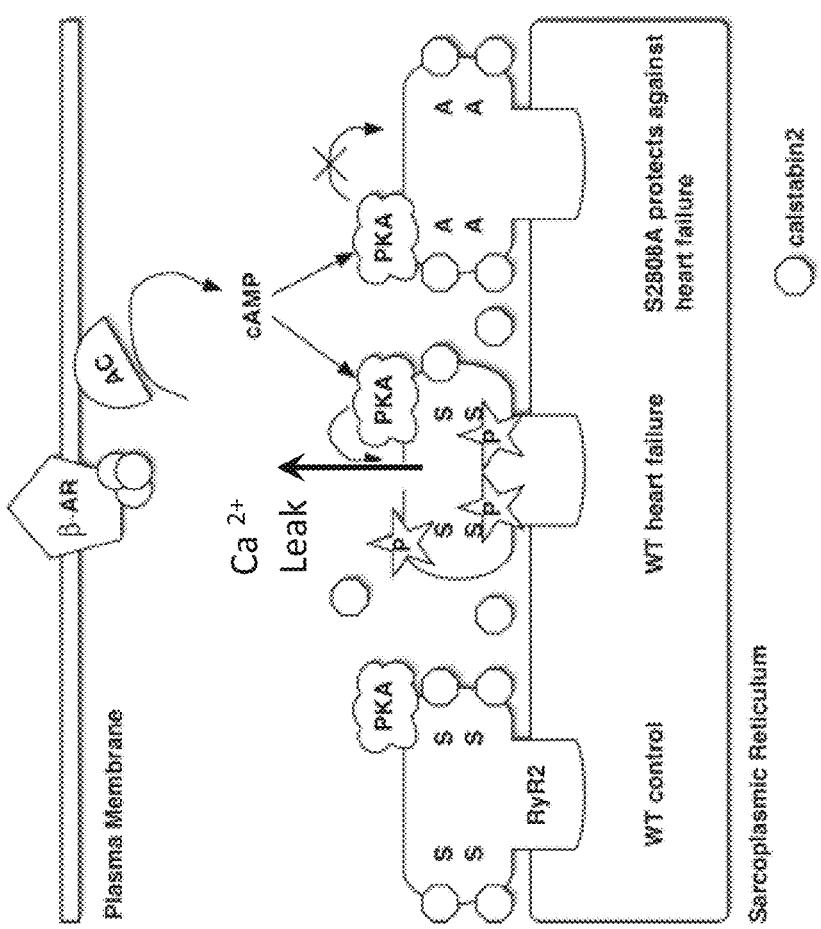
Figure 1. Cascade from cAMP production to calcium leakage from the sarcoplasmic reticulum
Marks, 2006

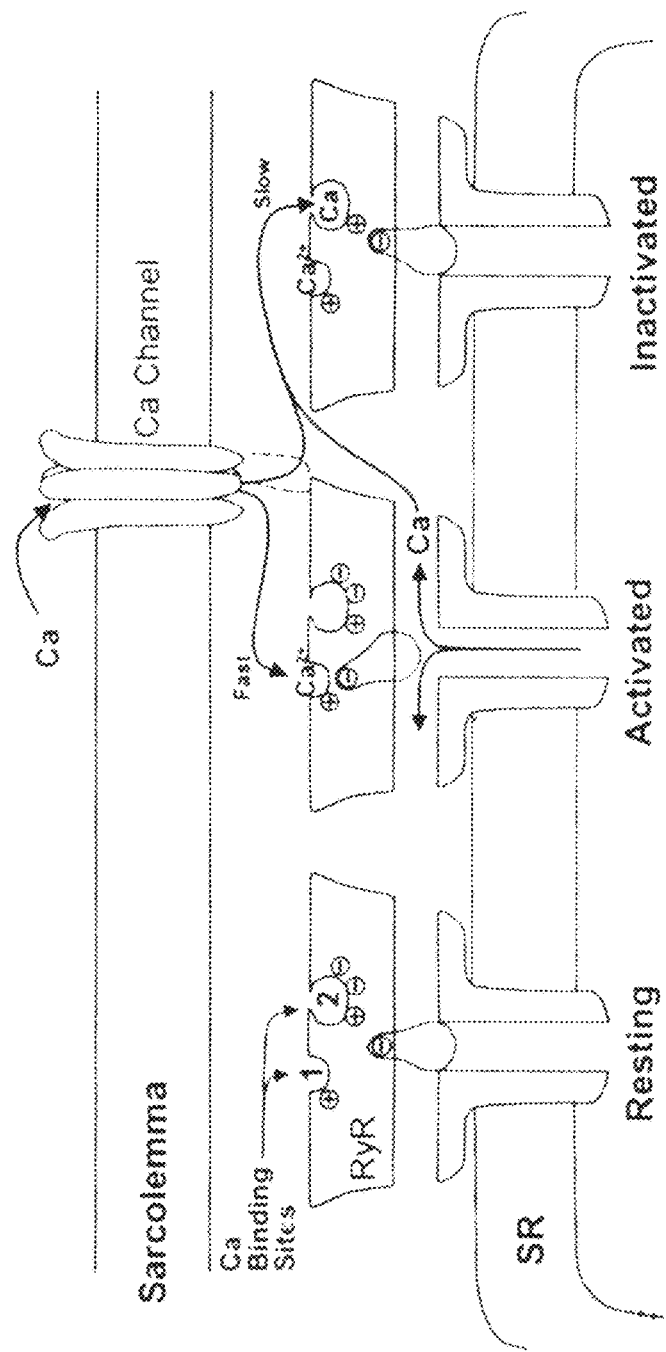

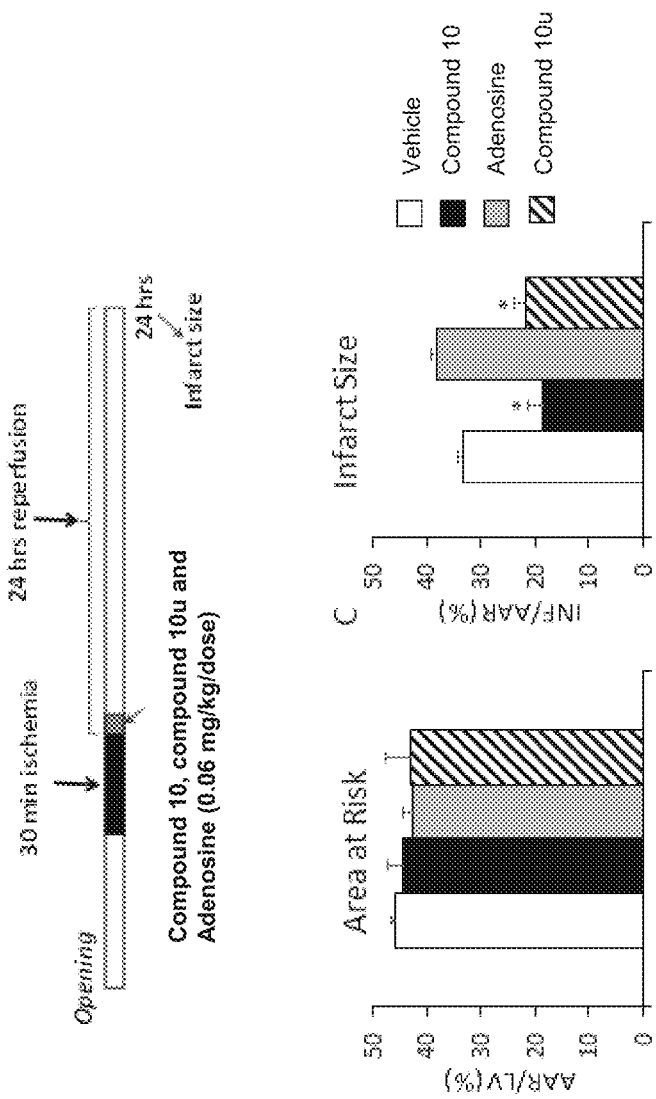
Figure 3. AC5 inhibitors of the present invention reduce infarct size when administered after reperfusion

ADENYLYL CYCLASE INHIBITORS, PHARMACEUTICAL COMPOSITIONS AND METHOD OF USE THEREOF

GOVERNMENT LICENSE RIGHTS

This invention was made with government support under SBRI grant R44HL112512 awarded by NHLBI. The government has certain rights in the invention.

RELATED U.S. APPLICATION DATA

Provisional application No. 62/352,198 filed on Jun. 20, 2016

BACKGROUND OF THE INVENTION

Cardiovascular disease represents a major cause of death worldwide. Despite the advances in the treatment of Acute Myocardial Infarction (AMI) and Heart Failure (HF) over the past several decades, these diseases are the most significant for health in the U.S. According to the 2009 heart disease and stroke statistics as part of the American Heart Association (AHA) statistical update, it is estimated that 1 out of every 5 deaths in the United States is caused by coronary artery heart disease.

Although numerous interventions have been studied over the past 50 years to limit infarct size in patients presenting with MI, almost none have made it to the clinics. A major reason is that almost all of these therapies require administering the agent before the ischemic episode, which is impractical in patients coming to the hospital with MI. Many of the adjunctive therapies along with reperfusion therapy have failed in clinical trials.

More than 900,000 Americans suffer a myocardial infarction each year, one-third of these are diagnosed as acute ST-segment elevation myocardial Infarction (STEMI), and the 30-day mortality rate from this disease is about 30%. Thus, there is a need for novel therapeutic agents capable of minimizing or preventing damage to the human myocardium during ischemic episodes.

Presently, approximately 5.1 million people in the United States suffer from HF. In 2009, one in nine deaths listed HF as a contributing cause. Furthermore, of those who develop HF, approximately half will die within 5 years. Finally, the annual cost of HF care to the healthcare system is estimated at $32 billion dollars. Thus, there is a need for novel therapeutic agents capable of minimizing or preventing development of or advancement of HF.

β-Adrenergic signaling is a key process in cardiovascular, central nervous system and metabolic regulation. Unfortunately, the prolonged use of β-agonists and β-antagonists is plagued by poor tissue selectivity, sensitization and desensitization following therapy, and dynamic changes to the β-adrenergic receptors that are inconsistent among disease states. Through β-adrenergic signaling, adenylyl cyclases are activated.

The adenylyl cyclases (ACs) are a family of enzymes that are key elements of signal transduction by virtue of their ability to convert adenosine triphosphate (ATP) to cyclic adenosine monophosphate (cAMP). cAMP is a key regulator of PKA leading to calcium signaling in the human myocardium. At least nine isoforms of adenylyl cyclase are known and unique isoform combinations are expressed in a tissue specific manner. Type V AC is the predominant isoform found in heart tissue. Thus, the development of isoform specific inhibitors of adenylyl cyclase is a useful strategy toward the design of novel therapeutic agents targeting cardiac function.

SUMMARY OF THE INVENTION

The present invention relates to novel potent inhibitors of adenylyl cyclase of Formula I:

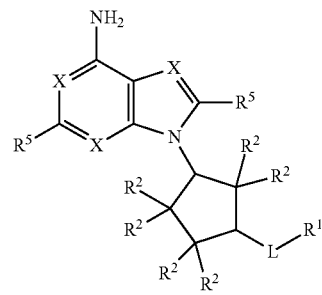

wherein,
$R^1$ is COOH, COOCH$_3$, CONH$_2$ or CONHOH;
Each $R^2$ is independently H, $C_1$-$C_6$ alkyl or —(CH$_2$)$_m$—$R^3$, wherein at least 3 $R^2$ groups must be H; or, independently of other $R^2$ groups, two $R^2$ groups residing on adjacent carbon atoms join to form a carbon-carbon double bond;
Each $R^3$ is independently OR$^4$, N(R$^4$)$_2$, SR$^4$, COOH, COOCH$_3$ or CONH$_2$;
Each $R^4$ is independently H or $C_1$-$C_6$ alkyl;
Each $R^8$ is independently F, Cl, Br, I, OH, OR$^6$, N(R$^6$)$_2$, SR$^6$, $C_1$-$C_6$ alkyl, CF$_3$, NO$_2$, COOH, COOCH$_3$, CONH$_2$ SO$_3$H, PO$_3$H or CN;
Each $R^6$ is independently H or $C_1$-$C_6$ alkyl;
$R^7$ is H or $C_1$-$C_6$ alkyl;
L is a direct link or —(CH$_2$)$_n$—Y—(CH$_2$)$_o$—;
Each X is independently N or CH;
Y is a direct link, O, S or NR$^7$;
Each m of each $R^2$ is an integer from 0 to 5;
n is an integer from 0 to 5;
o is an integer from 0 to 5, wherein if L is not a direct link, o is not 0;
Each stereogenic center is independently either R or S; and,
If all $R^2$ groups are H, at least one of $R^5$ is not H or at least one of X is not N.

Another aspect of this invention relates to pharmaceutically acceptable salt forms of a structure of Formula I.
Another aspect of this invention relates to pharmaceutically acceptable co-crystal forms of a structure of Formula I.
Another aspect of this invention relates to a method of preparing a compound of Formula I

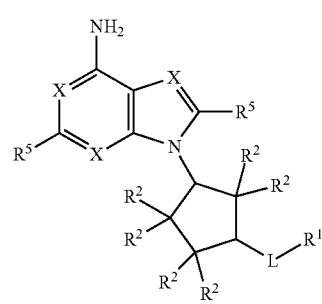

wherein,
$R^1$ is COOH, COOCH$_3$, CONH$_2$ or CONHOH;
Each $R^2$ is independently H, $C_1$-$C_6$ alkyl or —(CH$_2$)$_m$—$R^3$, wherein at least 3 $R^2$ groups must be H; or, independently of other $R^2$ groups, two $R^2$ groups residing on adjacent carbon atoms join to form a carbon-carbon double bond;

Each $R^3$ is independently $OR^4$, $N(R^4)_2$, $SR^4$, COOH, $COOCH_3$ or $CONH_2$;
Each $R^4$ is independently H or $C_1$-$C_6$ alkyl;
Each $R^5$ is independently F, Cl, Br, I, OH, $OR^6$, $N(R^6)_2$, $SR^6$, $C_1$-$C_6$ alkyl, $CF_3$, $NO_2$, COOH, $COOCH_3$, $CONH_2$ $SO_3H$, $PO_3H$ or CN;
Each $R^6$ is independently H or $C_1$-$C_6$ alkyl;
$R^7$ is H or $C_1$-$C_6$ alkyl;
L is a direct link or —$(CH_2)_n$—Y—$(CH_2)_o$—;
Each X is independently N or CH;
Y is a direct link, O, S or $NR^7$;
Each m of each $R^2$ is an integer from 0 to 5;
n is an integer from 0 to 5;
o is an integer from 0 to 5, wherein if L is not a direct link, o is not 0;
Each stereogenic center is independently either R or S; and,
If all $R^2$ groups are H, at least one of $R^8$ is not H or at least one of X is not N;
Comprising the steps of:
(1) Reacting a compound of Formula II with a compound of Formula III

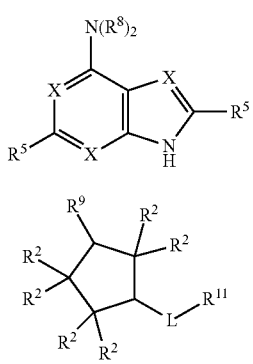

wherein, all substitutions are defined according to claim 1 and wherein,
Each $R^8$ is independently H or a suitable protecting group selected from the list comprising but not limited to Boc, Cbz, Fmoc, Teoc, benzyl and benzylidene;
$R^9$ is Cl, Br, I or $OR^{10}$;
$R^{10}$ is H, Methanesulfonyl, Trifluoromethanesulfonyl, Toluenesulfonyl or Nitrophenylsulfonyl;
$R^{11}$ is $COOR^{12}$; and,
$R^{12}$ is H or $C_1$-$C_6$ alkyl.
(2) Removing a protecting group if a protecting group is present.
(3) Converting a carboxylic acid or an ester to a hydroxamic acid.
Another aspect of this invention relates to pharmaceutical compositions comprising a compound of Formula I or a pharmaceutically acceptable salt or co-crystal thereof, and a pharmaceutically acceptable diluent or carrier.
The compounds of the present invention directly inhibit adenylyl cyclases and are therefore useful for treating cardiovascular diseases in patients suffering from such disorders.
Another aspect of this invention relates to a method of treating a cardiovascular disease in a patient by administering an effective amount of an adenylyl cyclase inhibitor to a patient diagnosed with congestive heart failure or ischemic reperfusion injury.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:
FIG. 1 is an illustration of the cascade from cAMP production to calcium leakage from the sarcoplasmic reticulum.
FIG. 2 is an illustration of how calcium leakage from the sarcoplasmic reticulum leads to myocyte contraction.
It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.
FIG. 3 demonstrates that i.v. administration of AC5 inhibitors of the present invention to mice after coronary artery reperfusion reduce infarct size.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.
The embodiments of the present invention provide structures and methods for preparing structures that are useful as treatments for various cardiovascular diseases and other vasospastic disorders.

1. General Description of the Compounds in at Least Some Embodiments of the Invention At least one embodiment of the present invention provides a structure of Formula I

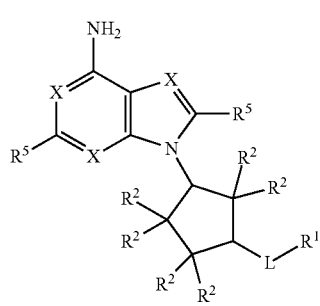

wherein,
$R^1$ is COOH, $COOCH_3$, $CONH_2$ or CONHOH;
Each $R^2$ is independently H, $C_1$-$C_6$ alkyl or —$(CH_2)_m$—$R^3$, wherein at least 3 $R^2$ groups must be H; or, independently of other $R^2$ groups, two $R^2$ groups residing on adjacent carbon atoms join to form a carbon-carbon double bond;

Each $R^3$ is independently $OR^4$, $N(R^4)_2$, $SR^4$, COOH, $COOCH_3$ or $CONH_2$;

Each $R^4$ is independently H or $C_1$-$C_6$ alkyl;

Each $R^8$ is independently F, Cl, Br, I, OH, $OR^6$, $N(R^6)_2$, $SR^6$, $C_1$-$C_6$ alkyl, $CF_3$, $NO_2$, COOH, $COOCH_3$, $CONH_2$ $SO_3H$, $PO_3H$ or CN;

Each $R^6$ is independently H or $C_1$-$C_6$ alkyl;

$R^7$ is H or $C_1$-$C_6$ alkyl;

L is a direct link or —$(CH_2)_n$—Y—$(CH_2)_o$—;

Each X is independently N or CH;

Y is a direct link, O, S or $NR^7$;

Each m of each $R^2$ is an integer from 0 to 5;

n is an integer from 0 to 5;

o is an integer from 0 to 5, wherein if L is not a direct link, o is not 0;

Each stereogenic center is independently either R or S; and,

If all $R^2$ groups are H, at least one of $R^5$ is not H or at least one of X is not N.

At least some embodiments of the present invention further provide a method for preparing a structure of Formula I, pharmaceutical compositions comprising a structure of Formula I and methods of using a structure of Formula I to treat cardiovascular diseases.

2. Compounds and Definitions

Compounds of this embodiment include those described generally above, and are further illustrated by the classes, subclasses, and species disclosed herein. As used herein, the following definitions shall apply unless otherwise indicated. In at least some embodiments, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

An "alkyl" group refers, in one embodiment, to a saturated aliphatic hydrocarbon, including straight-chain, branched-chain and cyclic alkyl groups. In one embodiment, the alkyl group has 1-12 carbons. In another embodiment, the alkyl group has 1-7 carbons. In another embodiment, the alkyl group has 1-6 carbons. In another embodiment, the alkyl group has 1-4 carbons. The alkyl group may be unsubstituted or substituted by one or more groups selected from halogen, hydroxy, alkoxy, carboxylic acid, aldehyde, carbonyl, amido, cyano, alkylamido, dialkylamido, nitro, amino, alkylamino, dialkylamino, carboxyl, thio and thioalkyl.

An "alkenyl" group refers, in another embodiment, to an unsaturated hydrocarbon, including straight chain, branched chain and cyclic groups having one or more double bonds. The alkenyl group may have one double bond, two double bonds, three double bonds, etc. In another embodiment, the alkenyl group has 2-12 carbons. In another embodiment, the alkenyl group has 2-6 carbons. In another embodiment, the alkenyl group has 2-4 carbons. In another embodiment, the alkenyl group is ethenyl (—CH=$CH_2$) Examples of alkenyl groups that may be included are ethenyl, propenyl, butenyl, cyclohexenyl, etc. The alkenyl group may be unsubstituted or substituted by a halogen, hydroxy, alkoxy carbonyl, amido, alkylamido, dialkylamido, nitro, cyano, amino, alkylamino, dialkylamino, carboxyl, thio and/or thioalkyl.

An "alkynyl" group refers, in another embodiment, to an unsaturated hydrocarbon, including straight chain, branched chain and cyclic groups having one or more triple bonds. The alkynyl group may have one triple bond, two triple bonds, three triple bonds, etc. In another embodiment, the alkynyl group has 2-12 carbons. In another embodiment, the alkynyl group has 2-6 carbons. In another embodiment, the alkynyl group has 2-4 carbons. In another embodiment, the alkynyl group is ethynyl. Examples of alkenyl groups are ethynyl, propynyl, butynyl, cyclohexynyl, etc. The alkynyl group may be unsubstituted or substituted by a halogen, hydroxy, alkoxy carbonyl, cyano, amido, alkylamido, dialkylamido, nitro, amino, alkylamino, dialkylamino, carboxyl, thio and/or thioalkyl.

In one embodiment, the term "halogen" refers, in one embodiment to F, in another embodiment to Cl, in another embodiment to Br, and in another embodiment to I.

A "carbocyclic ring" group refers, in one embodiment, to a saturated or non-saturated hydrocarbon ring. In one embodiment, the carbocyclic ring group has 4-12 carbons. In another embodiment, the carbocyclic ring group has 4-8 carbons. In another embodiment, the carbocyclic ring comprises of 2-3 fused rings. The alkyl group may be unsubstituted or substituted by one or more groups selected from halogen, hydroxy, alkoxy, carboxylic acid, aldehyde, carbonyl, amido, cyano, alkylamido, dialkylamido, nitro, amino, alkylamino, dialkylamino, carboxyl, thio and thioalkyl. The carbocyclic ring may be substituted by one or more groups selected from halogen, hydroxy, alkoxy, carboxylic acid, aldehyde, carbonyl, amido, cyano, alkylamido, dialkylamido, nitro, amino, alkylamino, dialkylamino, carboxyl, thio and thioalkyl.

A "heterocycle" group refers, in one embodiment, to a ring structure comprising in addition to carbon atoms, sulfur, oxygen, nitrogen or any combination thereof, as part of the ring. In another embodiment, the heterocycle is a 3-12 membered ring. In another embodiment, the heterocycle is a 6 membered ring. In another embodiment, the heterocycle is a 5-7 membered ring. In another embodiment, the heterocycle is a 4-8 membered ring. In another embodiment, the heterocycle group may be unsubstituted or substituted by a halogen, haloalkyl, hydroxyl, alkoxy, carbonyl, amido, alkylamido, dialkylamido, cyano, nitro, $CO_2H$, amino, alkylamino, dialkylamino, carboxyl, thio and/or thioalkyl. In another embodiment, the heterocycle ring may be fused to another saturated or unsaturated cycloalkyl or heterocyclic 3-8 membered ring. In another embodiment, the heterocyclic ring is a saturated ring. In another embodiment, the heterocyclic ring is an unsaturated ring.

An "aryl" group refers, in one embodiment, to an aromatic ring structure comprising 6-14 carbon atoms. In one embodiment, the aryl group has 6 carbons. In another embodiment, the aryl group has 12 carbons. In another embodiment, the aryl group has 14 carbon atoms. The aryl group may be unsubstituted or substituted by one or more groups selected from halogen, hydroxy, alkoxy, carboxylic acid, aldehyde, carbonyl, amido, cyano, alkylamido, dialkylamido, nitro, amino, alkylamino, dialkylamino, carboxyl, thio and thioalkyl. The carbocyclic ring may be substituted by one or more groups selected from halogen, hydroxy, alkoxy, carboxylic acid, aldehyde, carbonyl, amido, cyano, alkylamido, dialkylamido, nitro, amino, alkylamino, dialkylamino, carboxyl, thio and thioalkyl.

A "heteroaryl" group refers, in one embodiment, to an aromatic ring structure comprising in addition to carbon atoms, sulfur, oxygen, nitrogen or any combination thereof, as part of the ring. In another embodiment, the heteroaryl group is a 5-14 membered ring. In another embodiment, the heteroaryl group is a 5-membered ring. In another embodiment, the heteroaryl group is a 6-membered ring. In another embodiment, the heteroaryl group is a bicyclic ring structure containing 9 atoms. In another embodiment, the heteroaryl group is a bicyclic ring structure containing 10 atoms. In another embodiment, the heteroaryl group is a bicyclic ring structure containing 14 atoms. The heteroaryl group may be unsubstituted or substituted by one or more groups selected from halogen, hydroxy, alkoxy, carboxylic acid, aldehyde, carbonyl, amido, cyano, alkylamido, dialkylamido, nitro, amino, alkylamino, dialkylamino, carboxyl, thio and thioalkyl. The carbocyclic ring may be substituted by one or more groups selected from halogen, hydroxy, alkoxy, carboxylic acid, aldehyde, carbonyl, amido, cyano, alkylamido, dialkylamido, nitro, amino, alkylamino, dialkylamino, carboxyl, thio and thioalkyl.

A "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

A "pharmaceutically acceptable co-crystal" refers to those co-crystals which are, within the scope of sound medical judgment, suitable for use in contact with the tissues of humans and lower animals without undue toxicity, irritation, allergic response and the like, and are commensurate with a reasonable benefit/risk ratio. Cocrystals are crystals that contain two or more non-identical molecules that form a crystalline structure. The intermolecular interactions between the non-identical molecules in the resulting crystal structures can result in physical and chemical properties that differ from the properties of the individual components. Such properties can include, for example, melting point, solubility, chemical stability, mechanical properties and others.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention. In certain embodiments, a warhead moiety, $R^1$, of a provided compound comprises one or more deuterium atoms.

3. Description of Exemplary Embodiments

At least one embodiment of the present invention provides a structure of Formula I

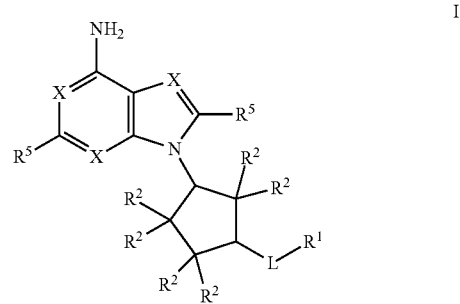

wherein,
$R^1$ is COOH, COOCH$_3$, CONH$_2$ or CONHOH;
Each $R^2$ is independently H, $C_1$-$C_6$ alkyl or —(CH$_2$)$_m$—$R^3$, wherein at least 3 $R^2$ groups must be H; or, independently of other $R^2$ groups, two $R^2$ groups residing on adjacent carbon atoms join to form a carbon-carbon double bond;
Each $R^3$ is independently OR$^4$, N(R$^4$)$_2$, SR$^4$, COOH, COOCH$_3$ or CONH$_2$;
Each $R^4$ is independently H or $C_1$-$C_6$ alkyl;
Each $R^5$ is independently F, Cl, Br, I, OH, OR$^6$, N(R$^6$)$_2$, SR$^6$, $C_1$-$C_6$ alkyl, CF$_3$, NO$_2$, COOH, COOCH$_3$, CONH$_2$ SO$_3$H, PO$_3$H or CN;
Each $R^6$ is independently H or $C_1$-$C_6$ alkyl;
$R^7$ is H or $C_1$-$C_6$ alkyl;
L is a direct link or —(CH$_2$)$_n$—Y—(CH$_2$)$_o$—;
Each X is independently N or CH;
Y is a direct link, O, S or NR$^7$;
Each m of each $R^2$ is an integer from 0 to 5;
n is an integer from 0 to 5;

o is an integer from 0 to 5, wherein if L is not a direct link, o is not 0;

Each stereogenic center is independently either R or S; and,

If all $R^2$ groups are H, at least one of $R^5$ is not H or at least one of X is not N.

At least some embodiments of the present invention further provide a method for preparing a structure of Formula I, pharmaceutical compositions comprising a structure of Formula I and methods of using a structure of Formula I to treat cardiovascular diseases.

As defined generally above, $R^1$ is COOH, $COOCH_3$, $CONH_2$ or CONHOH. In some embodiments, $R^1$ is COOH. In some embodiments, $R^1$ is $COOCH_3$. In some embodiments, $R^1$ is $CONH_2$. In some embodiments, $R^1$ is CONHOH.

As defined generally above, each $R^2$ is independently H, $C_1$-$C_6$ alkyl or —$(CH_2)_m$—$R^3$, wherein at least 3 $R^2$ groups must be H; or, independently of other $R^2$ groups, two $R^2$ groups residing on adjacent carbon atoms join to form a carbon-carbon double bond. In some embodiments, each $R^2$ is independently H, $C_1$-$C_6$ alkyl or —$(CH_2)_m$—$R^3$, wherein at least 3 $R^2$ groups must be H. In some embodiments, two $R^2$ groups residing on adjacent carbon atoms join to form a carbon-carbon double bond and any remaining $R^2$ groups are independently H, $C_1$-$C_6$ alkyl or —$(CH_2)_m$—$R^3$, wherein at least 3 $R^2$ groups must be H.

As defined generally above, each $R^3$ is independently $OR^4$, $N(R^4)_2$, $SR^4$, COOH, $COOCH_3$ or $CONH_2$.

As defined generally above, each $R^4$ is independently H or $C_1$-$C_6$ alkyl.

As defined generally above, each $R^5$ is independently F, Cl, Br, I, OH, $OR^6$, $N(R^6)_2$, $SR^6$, $C_1$-$C_6$ alkyl, $CF_3$, $NO_2$, COOH, $COOCH_3$, $CONH_2$ $SO_3H$, $PO_3H$ or CN.

As defined generally above, each $R^6$ is independently H or $C_1$-$C_6$ alkyl.

As defined generally above, $R^7$ is H or $C_1$-$C_6$ alkyl. In some embodiments, $R^7$ is H. In some embodiments, $R^7$ is $C_1$-$C_6$ alkyl.

As defined generally above, L is a direct link or —$(CH_2)_n$—Y—$(CH_2)_o$—.

As defined generally above, Each X is independently N or CH. In some embodiments one of X is N and two of X are CH. In some embodiments, two of X are N and one of X is CH. In some embodiments, three of X are N. In some embodiments, three of X are CH.

As defined generally above, Y is a direct link, O, S or $NR^7$. In some embodiments, Y is O. In some embodiments, Y is S. In some embodiments, Y is $NR^7$.

As defined generally above, each m of each $R^2$ is an integer from 0-5. In some embodiments, m is 0. In some embodiments, at least one of m is 1. In some embodiments, at least one of m is 2. In some embodiments, at least one of m is 3. In some embodiments, at least one of m is 4. In some embodiments, at least one of m is 5.

As defined generally above, n is an integer from 0-5. In some embodiments, n is 0. In some embodiments, n is 1. In some embodiments, n is 2. In some embodiments, n is 3. In some embodiments, n is 4. In some embodiments, n is 5.

As defined generally above, o is an integer from 0-5, wherein if L is not a direct link, o is not 0. In some embodiments, when L is not a direct link, o is 1. In some embodiments, when L is not a direct link, o is 2. In some embodiments, when L is not a direct link, o is 3. In some embodiments, when L is not a direct link, o is 4. In some embodiments, when L is not a direct link, o is 5. In some embodiments, when L is a direct link, o is 0. In some embodiments, when L is a direct link, o is 1. In some embodiments, when L is a direct link, o is 2. In some embodiments, when L is a direct link, o is 3. In some embodiments, when L is a direct link, o is 4. In some embodiments, when L is a direct link, o is 5.

As defined generally above, each stereogenic center is independently either R or S. In some embodiments, at least one stereogenic center is R and at least one stereogenic center is S. In some embodiments, at least two stereogenic centers are R and the other stereogenic centers are S. In some embodiments, at least two stereogenic centers are S and the other stereogenic centers are R.

As defined generally above, if all $R^2$ groups are H, at least one of $R^8$ is not H or at least one of X is not N.

Another embodiment of the present invention provides a structure of Formula I

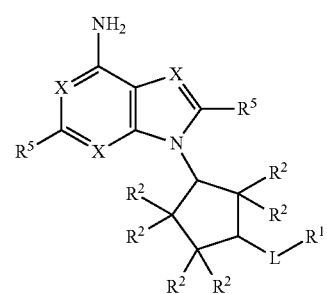

wherein,
$R^1$ is COOH or CONHOH;
Each $R^2$ is independently H, $C_1$-$C_6$ alkyl or —$(CH_2)_m$—$R^3$, wherein at least 3 $R^2$ groups must be H;
Each $R^3$ is $OR^4$;
Each $R^4$ is H;
Each $R^8$ is independently F, OH, $OR^6$, $N(R^6)_2$, $SR^6$, $C_1$-$C_6$ alkyl, $CF_3$, $NO_2$, COOH, $CONH_2$, or CN;
Each $R^6$ is H;
$R^7$ is H or $C_1$-$C_6$ alkyl;
L is a direct link or —$(CH_2)_n$—Y—$(CH_2)_o$—;
Each X is independently N or CH;
Y is a direct link, O or $NR^7$;
m is an integer from 0 to 3;
n is an integer from 0 to 3;
o is an integer from 0 to 3, wherein if L is not a direct link, o is not 0;
Each stereogenic center is independently either R or S; and,
If all $R^2$ groups are H, at least one of $R^5$ is not H or at least one of X is not N.

Yet another embodiment of the present invention provides a structure of Formula I

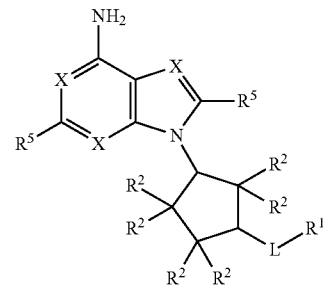

wherein,
$R^1$ is CONHOH;
Each $R^2$ is independently H, $C_1$-$C_6$ alkyl or —$(CH_2)_m$—$R^3$, wherein at least 3 $R^2$ groups must be H;
Each $R^3$ is $OR^4$;
Each $R^4$ is H;

Each $R^5$ is independently F, OH, $OR^6$, $N(R^6)_2$, $SR^6$, $C_1$-$C_6$ alkyl, $CF_3$, $NO_2$, COOH, $CONH_2$, or CN;
Each $R^6$ is H;
L is a direct link;
Each X is independently N or CH;
m is an integer from 0 to 3;
Each stereogenic center is independently either R or S; and,
If all $R^2$ groups are H, at least one of $R^5$ is not H or at least one of X is not N.

Another embodiment of the present invention provides a structure of Formula I

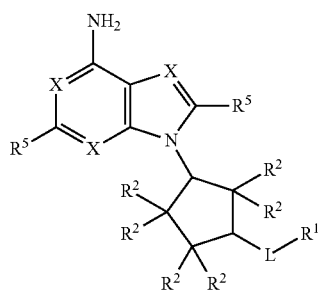

I wherein, said structure of Formula I further comprises a pharmaceutically acceptable salt form Another embodiment of the present invention provides a structure of Formula I

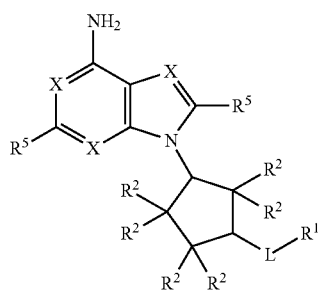

I wherein, said structure of Formula I further comprises a pharmaceutically acceptable co-crystal form Another aspect of this invention relates to a method of preparing a compound of Formula I

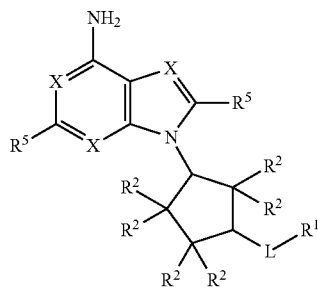

I wherein,
$R^1$ is COOH, $COOCH_3$, $CONH_2$ or CONHOH;
Each $R^2$ is independently H, $C_1$-$C_6$ alkyl or —$(CH_2)_m$—$R^3$, wherein at least 3 $R^2$ groups must be H; or, independently of other $R^2$ groups, two $R^2$ groups residing on adjacent carbon atoms join to form a carbon-carbon double bond;
Each $R^3$ is independently $OR^4$, $N(R^4)_2$, $SR^4$, COOH, $COOCH_3$ or $CONH_2$;
Each $R^4$ is independently H or $C_1$-$C_6$ alkyl;
Each $R^8$ is independently F, Cl, Br, I, OH, $OR^6$, $N(R^6)_2$, $SR^6$, $C_1$-$C_6$ alkyl, $CF_3$, $NO_2$, COOH, $COOCH_3$, $CONH_2$ $SO_3H$, $PO_3H$ or CN;
Each $R^6$ is independently H or $C_1$-$C_6$ alkyl;
$R^7$ is H or $C_1$-$C_6$ alkyl;
L is a direct link or —$(CH_2)_n$—Y—$(CH_2)_o$—;
Each X is independently N or CH;
Y is a direct link, O, S or $NR^7$;
Each m of each $R^2$ is an integer from 0 to 5;
n is an integer from 0 to 5;
o is an integer from 0 to 5, wherein if L is not a direct link, o is not 0;
Each stereogenic center is independently either R or S; and,
If all $R^2$ groups are H, at least one of $R^5$ is not H or at least one of X is not N;

Comprising the steps of:
(4) Reacting a compound of Formula II with a compound of Formula III

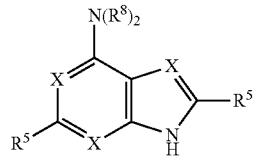

II

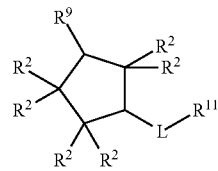

III wherein, all substitutions are defined according to claim 1 and wherein,
Each $R^8$ is independently H or a suitable protecting group selected from the list comprising but not limited to Boc, Cbz, Fmoc, Teoc, benzyl and benzylidene;
$R^9$ is Cl, Br, I or $OR^{10}$;
$R^{10}$ is H, Methanesulfonyl, Trifluoromethanesulfonyl, Toluenesulfonyl or Nitrophenylsulfonyl;
$R^{11}$ is $COOR^{12}$; and,
$R^{12}$ is H or $C_1$-$C_6$ alkyl.
(5) Removing a protecting group if a protecting group is present.
(6) Converting a carboxylic acid or an ester to a hydroxamic acid.

As defined generally above, each $R^8$ is independently H or a suitable protecting group selected from the list comprising but not limited to Boc, Cbz, Fmoc, Teoc, benzyl and benzylidene. In some embodiments, each $R^8$ is the same. In some embodiments, at least one of $R^8$ is H. In some embodiments, at least one of $R^8$ is Boc. In some embodiments, at least one of $R^8$ is Cbz. In some embodiments, at least one of $R^8$ is Fmoc. In some embodiments, at least one of $R^8$ is Teoc. In some embodiments, at least one of $R^8$ is benzyl. In some embodiments, at least one of $R^8$ is benzylidene.

As defined generally above, $R^9$ is Cl, Br, I or $OR^1$. In some embodiments, $R^9$ is Cl. In some embodiments, $R^9$ is Br. In some embodiments, $R^9$ is I. In some embodiments, $R^9$ is $OR^{10}$.

As defined generally above, $R^{10}$ is H, Methanesulfonyl, Trifluoromethanesulfonyl, Toluenesulfonyl or Nitrophenylsulfonyl. In some embodiments, $R^{10}$ is H. In some embodiments, $R^{10}$ is methanesulfonyl. In some embodiments, $R^{10}$ is trifluoromethanesulfonyl. In some embodiments, $R^{10}$ is toluenesulfonyl. In some embodiments, $R^{10}$ is nitrophenylsulfonyl.

As defined generally above, $R^{11}$ is $COOR^{12}$.

As defined generally above, $R^{12}$ is H or $C_1$-$C_6$ alkyl. In some embodiments, $R^{12}$ is H. In some embodiments, $R^{12}$ is $C_1$-$C_6$ alkyl.

Another aspect of this invention relates to a pharmaceutical composition comprising an effective amount of a structure of Formula I or a pharmaceutically acceptable salt or co-crystal thereof, and a pharmaceutically acceptable diluent or carrier.

Another aspect of this invention relates to a method of treating a cardiovascular disease comprising administering an effective amount of a pharmaceutical composition of comprising a structure of Formula I to a patient in need thereof. In some embodiments, said cardiovascular disease is congestive heart failure. In some embodiments, said cardiovascular disease is ischemic reperfusion injury.

In at least some embodiments of the present invention, compounds of Formula I are prepared according to the following schemes. One of ordinary skill in the art will recognize that alternative reagents and reactants can be used to generate the same target compounds and intermediates.

As illustrated in Scheme 1, commercially available racemic compound 1 is resolved providing the required enantiomer compound 2 by fractional recrystallization of the brucine salt of compound 1. Conversion of the carboxylic acid of compound 2 forming methyl ester compound 3 is achieved on reaction with acidic methanol. The ketone is then stereospecifically reduced to an alcohol on treatment with sodium borohydride yielding compound 4. Final conversion of the alcohol to the corresponding mesylate compound 5 is achieved on reaction with methanesulfonyl chloride.

Scheme 1-Preparation of intermediate compound 5

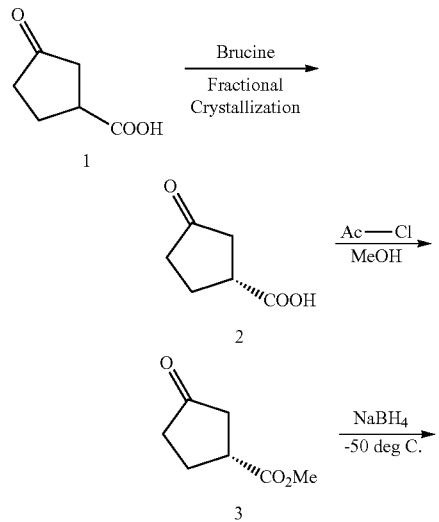

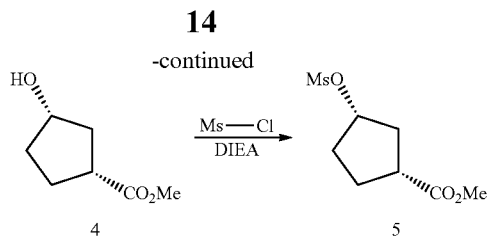

Relating to Scheme 1, one of ordinary skill in the art will recognize that chiral amines other than brucine are useful for the chiral resolution of racemic compound 1. Such chiral amines include, but are not limited to, S-methylbenzylamine, R-methylbenzylamine, quinine, cinchonine and strychnine. Furthermore, one of ordinary skill in the art will recognize that chiral resolution of compound 1 may also be achieved through generation of diastereomeric amide or diastereomeric ester derivatives followed by chromatographic separation of diastereomers and hydrolysis to liberate the required chiral compound 2. Such diastereomeric amides and esters are represented by, but not limited to, compound 6 and compound 7 illustrated in FIG. 1.

FIG. 1—Representative Diastereomeric Amide and Diastereomeric Ester Analogs of Racemic Compound 1

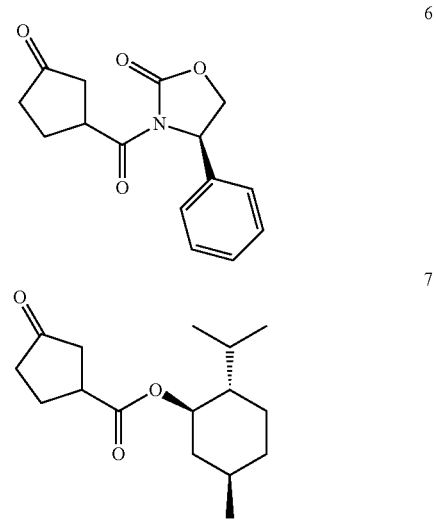

Further relating to Scheme 1, one of ordinary skill in the art will recognize that alternate and useful methods for the formation of methyl ester compound 3 are available. Such methods include, but are not limited to, reaction with reagents such as dimethyl sulfate, methyl iodide, diazomethane, trimethylsilyl diazomethane and methyl triflate. Additionally, one of ordinary skill in the art will recognize that reducing agents other than sodium borohydride are useful in the conversion of compound 3 to compound 4. Such reducing agents include, but are not limited to, sodium cyanoborohydride, sodium triacetoxyborohydride, lithium borohydride and borane. Furthermore, one of ordinary skill in the art will recognize that alternatives to the mesylate group of compound 5 are useful. Such mesylate alternatives include, but are not limited to, hydroxyl groups, chlorides, bromides, iodides, triflates, tosylates and nosylates.

As illustrated in Scheme 2, compound 8 is coupled with compound 5 under basic conditions. Subsequent treatment with trifluoroactic acid cleaves the Boc protecting groups yielding compound 9. Final reaction of compound 9 with hydroxylamine yields the desired hydroxamic acid compound 10.

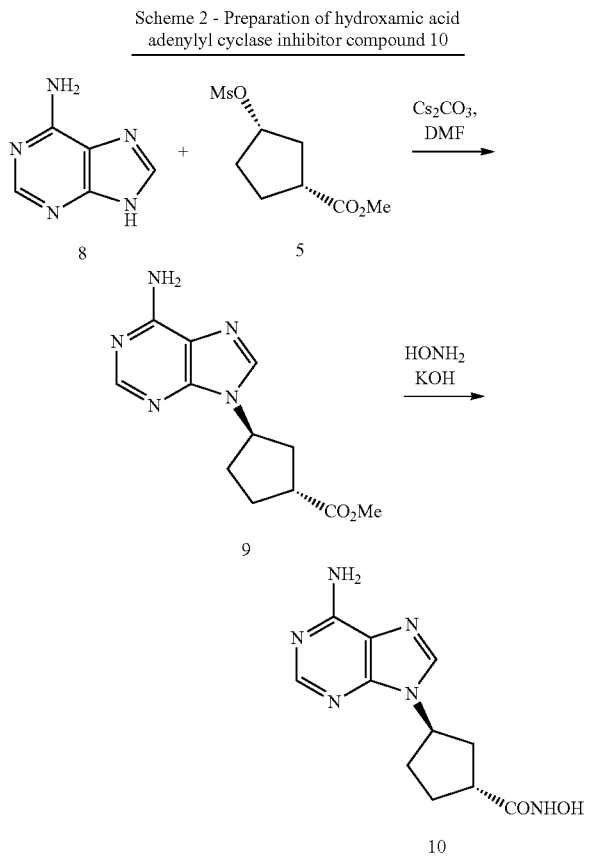

Relating to Scheme 2, one of ordinary skill in the art will recognize that native adenine or adenine derivatives bearing a free NH2 group are useful substrates for the chemistry illustrated in Scheme 2. Furthermore, one of ordinary skill in the art will recognize that in certain instances, protection of compound 8 (adenine) or compound 8 analogs (adenine derivatives) may be required. A non-limiting example of a protection strategy for compound 8 or compound 8 analogs is the placement of two Boc groups on the C-6 amino group. In addition to the Boc protecting group, one of ordinary skill in the art will recognize that alternate protecting groups are also useful for execution of the chemistry illustrated in Scheme 2. Such protecting groups include, but are not limited to, Cbz, Fmoc, Teoc, benzyl and benzylidene.

Further relating to Scheme 2, one of ordinary skill in the art will recognize that the coupling reaction between compound 8 and compound 5 (or related structures) may be executed using alternatives to the mesylate of compound 5. Such alternatives include, but are not limited to, leaving groups such as Cl, Br, I, OTf, OTs, and ONs. Furthermore, utilizing Mitsunobu chemistry, one of ordinary skill in the art will recognize that OH is an appropriate leaving group.

Relating to the hydroxamic acid formation of Scheme 2, one of ordinary skill in the at will recognize that alternative methods for the preparation of hydroxamic acids are available and include, but are not limited to, initial reaction with O-benzylhydroxylamine followed by catalytic hydrogenation to effect cleavage of the benzyl group and liberating the free hydroxamic acid.

Relating to both Scheme 1 and to Scheme 2, one of ordinary skill of the art will recognize that alternatives to compound 5 and to compound 8 are either available from commercial sources or by chemical synthesis. When chemical synthesis is required, compound 8 analogs and compound 5 analogs are available using chemistry generally known to one of ordinary skill in the art.

At least some of the embodiments of the present invention provide one or more intermediates of a synthetic method of the invention. In certain aspects, intermediates are compounds having one or more of the formulas selected from the following non-inclusive list:

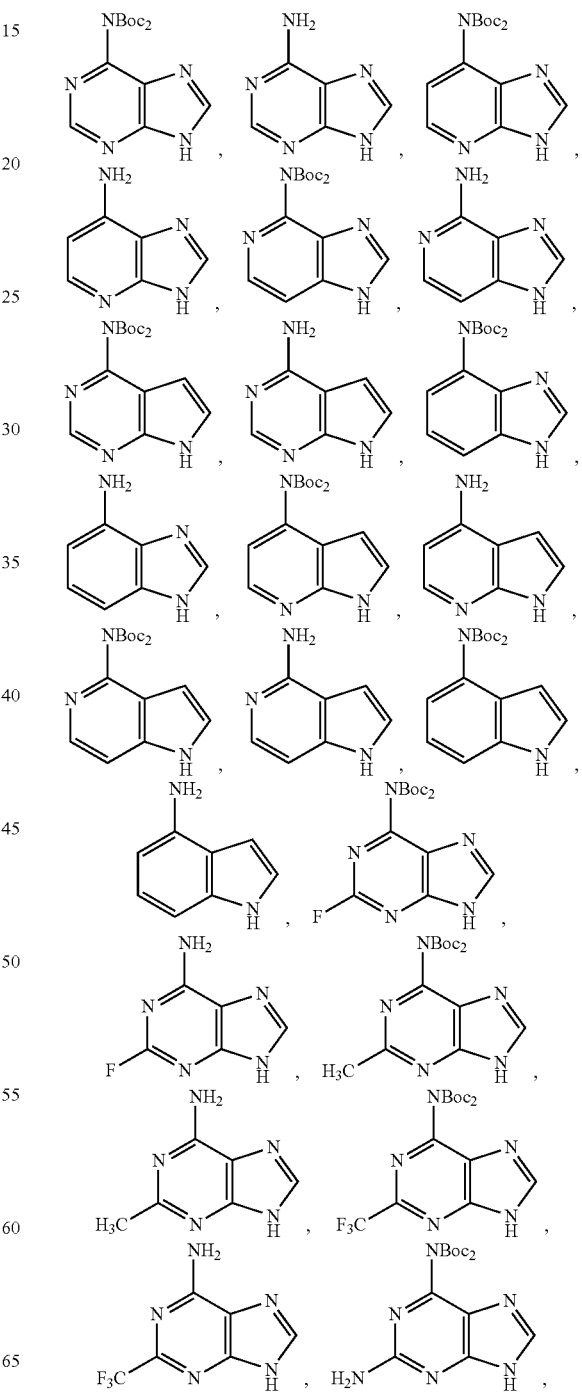

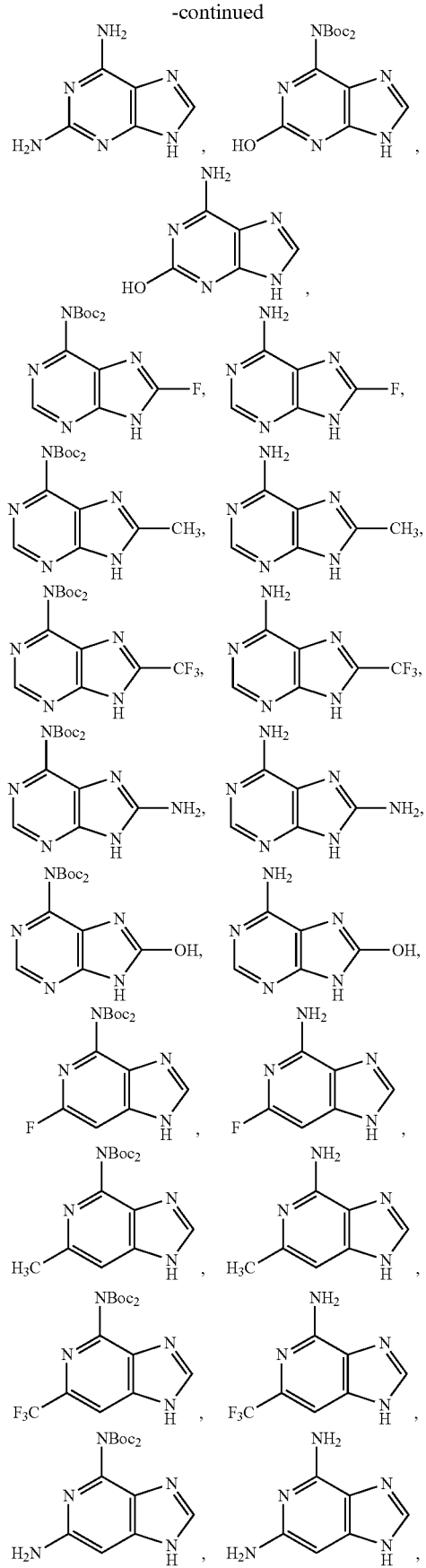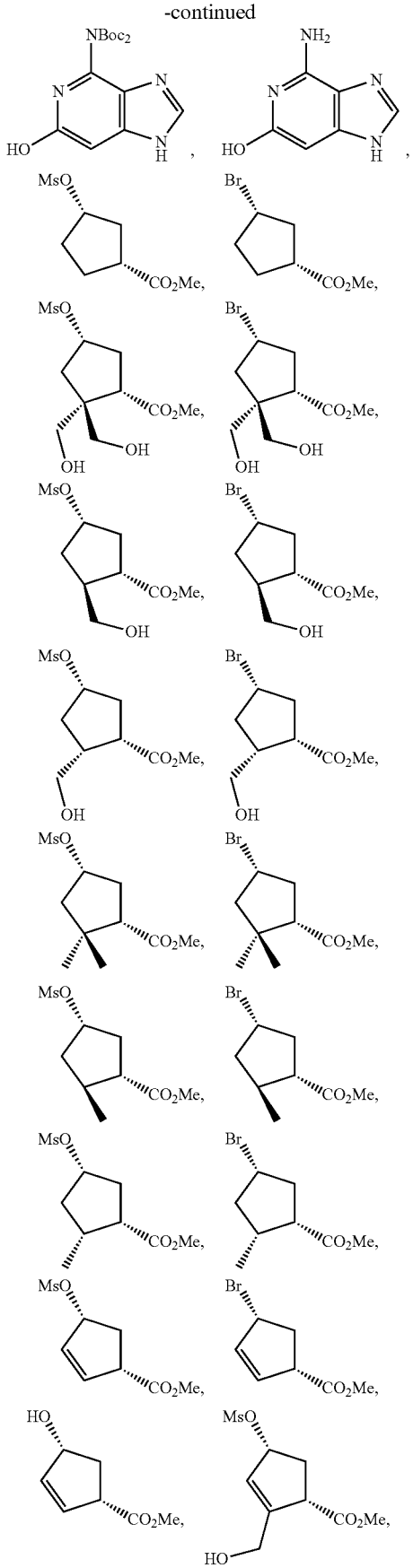

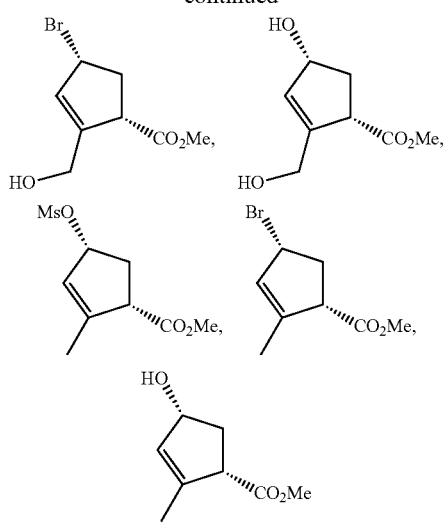

Exemplary compounds of Formula I are set forth in Table 1, below:

TABLE 1

| Compound ID | Compound Structure |
|---|---|
| 10 | (adenine-cyclopentyl-CONHOH) |
| 10a | (4-aminoimidazo[4,5-c]pyridine-cyclopentyl-COOH) |
| 10b | (4-aminoimidazo[4,5-c]pyridine-cyclopentyl-CONHOH) |
| 10c | (7-deazaadenine-cyclopentyl-COOH) |
| 10d | (7-deazaadenine-cyclopentyl-CONHOH) |
| 10e | (4-amino-pyrrolo[3,2-c]pyridine-cyclopentyl-COOH) |
| 10f | (4-amino-pyrrolo[3,2-c]pyridine-cyclopentyl-CONHOH) |
| 10g | (adenine-cyclopentyl-COOH with CH$_2$OH) |

TABLE 1-continued

Exemplary Compounds of Formula I

| Compound ID | Compound Structure |
|---|---|
| 10h | adenine-cyclopentyl with CONHOH and CH2OH substituents |
| 10i | adenine-cyclopentyl with CONHOH and CH2OH substituents |
| 10j | 2-fluoroadenine-cyclopentyl-CONHOH |
| 10k | 2-methyladenine-cyclopentyl-CONHOH |
| 10l | 2-trifluoromethyladenine-cyclopentyl-CONHOH |
| 10m | 2,6-diaminopurine-cyclopentyl-CONHOH |
| 10n | 2-hydroxyadenine-cyclopentyl-CONHOH |
| 10o | 8-methyladenine-cyclopentyl-CONHOH |
| 10p | 8-trifluoromethyladenine-cyclopentyl-CONHOH |
| 10q | 8-aminoadenine-cyclopentyl-CONHOH |

TABLE 1-continued

Exemplary Compounds of Formula I

| Compound ID | Compound Structure |
|---|---|
| 10r | adenine with cyclopentyl-CONHOH, 8-OH |
| 10s | adenine with methyl-cyclopentyl-CONHOH |
| 10t | 2-F adenine with methyl-cyclopentyl-CONHOH |
| 10u | 6-F imidazo[4,5-c]pyridine with methyl-cyclopentyl-CONHOH |
| 10v | 6-F imidazo[4,5-c]pyridine with cyclopentyl-CONHOH |

In certain embodiments, the present invention provides any compound selected from those depicted in Table 1, above, or a pharmaceutically acceptable salt or a pharmaceutically acceptable co-crystal thereof.

Compounds or salts thereof or co-crystals thereof provided by the present invention may be utilized in any of a variety of forms. For example, in some embodiments, provided compounds (or salts thereof or co-crystals thereof) are utilized in a solid form; in some such embodiments, provided compounds (or salts thereof or co-crystals thereof) are utilized in an amorphous solid form. In some embodiments, provided compounds are utilized in a crystalline solid form. In some embodiments, provided compounds (or salts thereof or co-crystals thereof) are utilized in a solid form (e.g., a crystalline solid form) that is a solvate or hydrate.

According to some embodiments, the invention provides a composition comprising a compound of this invention or a pharmaceutically acceptable derivative thereof and a pharmaceutically acceptable carrier, adjuvant, or vehicle.

In certain embodiments, the invention provides compositions containing an amount of compound effective to measurably inhibit adenylyl cyclase, in a biological sample or in a patient. In certain embodiments, the amount of compound in compositions of this invention is such that is effective to measurably inhibit an adenylyl cyclase mediated biological process in a biological sample or in a patient. In certain embodiments, provided compositions contain a unit dose amount of a compound described herein, wherein administration of such unit dose amount as part of a therapeutic regimen correlates with a desired pharmacologic and/or therapeutic outcome.

Compounds and compositions described herein are useful in the treatment of any of a variety of diseases, disorders, and conditions. In some embodiments, provided compounds and compositions are useful in the treatment of diseases, disorders, or conditions associated with activity of adenylyl cyclase.

Compounds and compositions described herein are useful in the treatment of any of a variety of diseases, disorders, and conditions. In some embodiments, provided compounds and compositions are useful in the treatment of diseases, disorders, or conditions associated with activity of adenylyl cyclase.

Regarding adenylyl cyclase, □-adrenergic signaling is a key process associated with cardiovascular, metabolic and central nervous system functions. Current therapies utilizing β-agonists and β-antagonists generally are inadequate relative to tissue selectivity and sensitization and desensitization due to prolonged exposure. Furthermore, these classes of therapeutics may cause side effects that impact the cardiovascular and pulmonary system. Additional potential side effects may relate to insulin-induced hypoglycemia and sexual dysfunction.

In mammals, adenylyl cyclases are integral membrane proteins associated to G-protein coupled receptors (GPCR) that influence cardiac function such as β-adrenergic receptor. Adenylyl cyclase type V isoform being the predominant isoform in cardiac tissue. As illustrated in FIG. 1, adenylyl cyclase converts ATP into cAMP. cAMP then activates Protein Kinase A (PKA) which, in turn, phosphorylates the ryanodine receptor at the sarcoplasmic reticulum in cardiomyocytes. This phosphorylation step then leads to calcium leakage from the sarcoplasmic reticulum.

As illustrated in FIG. 2, calcium leaking from the sarcoplasmic reticulum can populate a high affinity calcium binding site on the sarcoplasmic reticulum. This interaction then leads to release of cardiomyocyte intramolecular calcium stores resulting in cardiomyocyte contraction. When the calcium levels are high enough, a low affinity calcium binding site is populated resulting in re-containment of cardiomyocyte calcium back into the sarcoplasmic reticulum.

Because cardiomyocyte contractions are regulated by calcium signaling and because calcium signaling in cardiac tissue is regulated by cAMP levels, inhibitors of type V adenylyl cyclase are useful therapeutics for the modulation of cardiac function in patients suffering from heart diseases.

EXAMPLES

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

In executing the following exemplary synthetic protocols, the following relates to particulars relevant to equipment and analytical protocols. Microwave reactions were carried out utilizing an Anton Paar, Monowave 300. Preparative HPLC were carried out utilizing a Shimadzu [Prominence LC-20AP], Kinetex C-18 column (250×21.2 mm, 5µ) and the following method. Solvent A=Acetonitrile, Solvent B=0.01% TFA in Water (10:90). Flow Rate: 30 ml/min. LC-MS analyses were carried utilizing a Shimadzu [LCMS-2020], Kinetex, C-18 column (50×2.1 mm, 1.7µ) with the following method. Solvent A=Acetonitrile, B=0.01% TFA in water; Initial 95% of solvent B, then run gradient, which should reach 90% solvent A within 10 min and hold 90% solvent A for another 5 min. Flow Rate: 0.4 ml/min.

Examples 1-4—Preparation of Compound 5

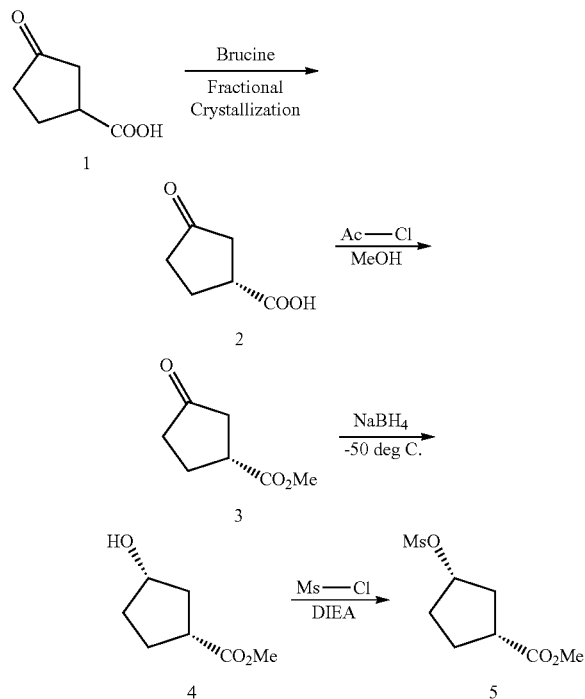

Example 1—Preparation of (R)-3-oxocyclopentanecarboxylic acid (Compound 2)

Compound 1 (57 g, 445.3 mmoles) and brucine (193.2 g, 489.8 mmoles) were combined with water (1.036 L) and heated to reflux until a clear solution was observed. The mixture was allowed to cool to room temperature. The resulting crystals were collected by filtration, washed with water and dried. The resulting crystals were recrystallized from water (500 mL) three times giving (R)-3-oxocyclopentanecarboxylic acid brucine salt in 99.71% ee as determined by chiral HPLC.

(R)-3-oxocyclopentanecarboxylic acid brucine salt (110 g) was combined with water (484 mL) and heated to reflux until a clear solution was observed. $NH_4OH$ (25% in $H_2O$, 352 mL) was added dropwise at 80 deg C. over 20 min (pH=12) and the resulting mixture was allowed to cool to room temp. The solids were removed by filtration and the filtrate was concentrated. The resulting crude residue was diluted with water (50 mL) and acidified with 1N HCL. The product was extracted with ether (3×50 mL). The ether extracts were dried over anhydrous sodium sulfate, filtered and concentrated to dryness giving a compound 2 as a white solid in 15% yield. SOR: $|\alpha|_5^{2C}$ +23.1° (C=1.0 in MeOH). $^1$HNMR (500 MHz, DMSO-$d_6$) δ ppm: 12.4 (brs, 1H), 3.1 (m, 1H), 2.4-2.2 (m, 2H), 2.25-2.15 (m, 3H), 2.0 (m, 1H); Mass (m/z): 129.4 (M+H).

Example 2—Preparation of (R)-methyl 3-oxocyclopentanecarboxylate (Compound 3)

Acetyl chloride (6.66 mL, 93.7 mmoles) was slowly added to MeOH (300 mL) and cooled to 0 deg C. (R)-3-oxocyclopentanecarboxylic acid 2 (10 g, 78.1 mmoles) was dissolved in MeOH (30 mL) and added to the acetyl chloride/methanol mixture. The reaction was stirred at room temp for 4 h after which, it was concentrated to dryness. Purification of the residue on silica gel (30% EtOAc in hexane) gave compound 3 as a pale-yellow oil in 86% yield.

SOR: $|\alpha|_5^{2C}$ +37.78° (C=1.0 in CHCl$_3$). $^1$HNMR (500 MHz, DMSO-$d_6$) δ ppm: 3.65 (s, 3H), 3.25-3.15 (m, 1H), 2.45-2.25 (m, 2H), 2.25-2.15 (m, 3H), 2.05-1.95 (m, 1H); Mass (m/z): 143.6 (M+H).

Example 3—Preparation of (1R,3S)-methyl 3-hydroxycyclopentanecarboxylate (Compound 4)

Compound 3 (10 g, 70.4 mmoles) was dissolved in MeOH (120 mL) and cooled −50 deg C. NaBH$_4$ (3.21 g, 84.5 mmoles) was added to the compound 3 solution (10 g, 0.0704 mol) in portions. The resulting mixture was stirred for 60 min at −50 deg C., after which it was quenched with glacial acetic acid (pH~6) at −50 deg C. The reaction mixture was concentrated to dryness and the residue was purified on silica gel (30% EtOAc in Hexane) giving compound 4 as a colorless oil and a diastereomeric mixture in 76.6% yield.

Compound 4 (10 g) was purified by PREP HPLC, giving diastereomerically pure compound 4 as a colorless oil in 46.6% yield. $^1$HNMR (500 MHz, DMSO-$d_6$) δ ppm: 4.55 (s, 1H), 4.1-4.0 (m, 1H), 3.6 (s, 3H), 2.8-2.7 (m, 1H), 2.1-2.0 (m, 1H), 1.9-1.8 (m, 1H), 1.8-1.7 (m, 1H), 1.7-1.6 (m, 2H), 1.5 (m, 1H): Mass (m/z): 145.5 (M+H); Chiral HPLC Purity: 99.96%.

Example 4—Preparation of (1R,3S)-methyl 3-(methylsulfonyloxy)cyclopentanecarboxylate (Compound 5)

Compound 4 (1 g, 6.944 mmoles) was dissolved in anhydrous dichloromethane (20 mL) and diisopropyl ethyl-amine (1.8 mL, 10.41 mmoles) was added. The resulting solution was cooled to 0 deg C. and methanesulfonyl chloride (0.67 mL, 8.68 mmoles) was slowly added at 0 deg C. The reaction was stirred at 0 deg C. for 1 h, after which it was concentrated to dryness. Purification of the residue on silica gel (40% ethyl acetate in hexane) gave compound 5 as a pale-yellow oil in 66.8% yield. $^1$HNMR (500 MHz, DMSO-$d_6$) δ ppm: 5.1 (m, 1H), 3.65 (s, 3H), 3.2 (s, 3H), 2.95-2.85 (m, 1H), 2.4-2.3 (m, 1H), 2.1-2.0 (m, 1H), 1.95-1.8 (m, 4H); Mass (m/z): 223.5 (M+H).

Examples 5-7—Preparation of Compound 10j

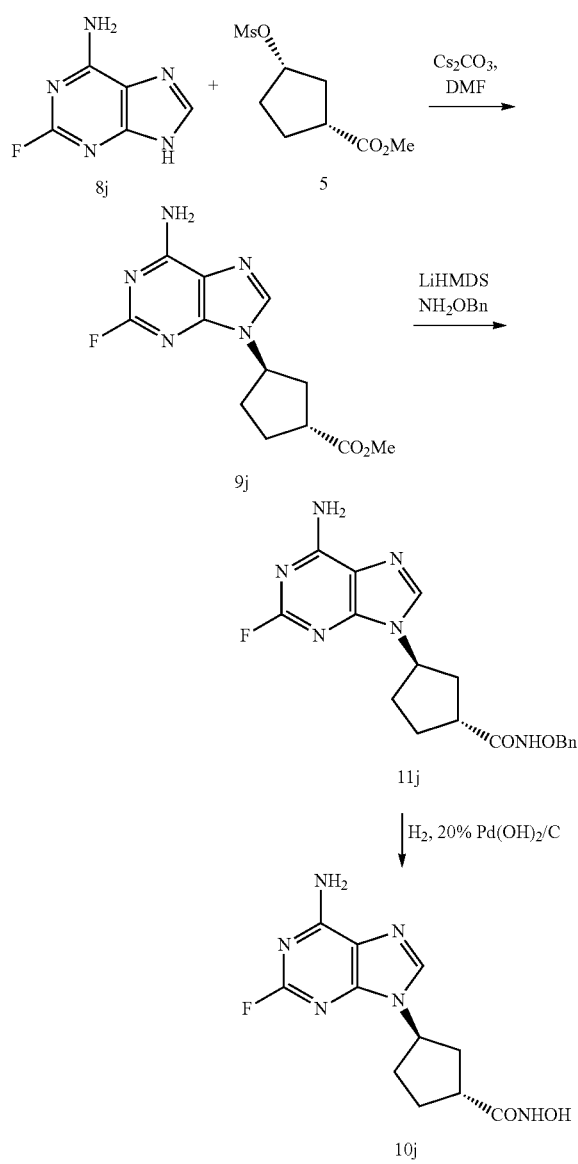

Example 5—Preparation of (1R,3R)-methyl 3-(6-amino-2-fluoro-9H-purin-9-yl)cyclopentanecarboxylate (Compound 9j)

2-Fluoroadenine (compound 8j, 200 mg, 1.306 mmoles) and compound 5 (377 mg, 1.698 mmoles) were dissolved in anhydrous N,N-dimethylformamide (5 mL) cesium carbonate (425 mg, 1.306 mmoles) was added. The resulting mixture was stirred at 80 deg C. for 5 hours. After cooling to room temperature, the mixture was filtered and concentrated to dryness. The residue was purified on basic alumina (2% methanol in dichloromethane) giving compound 9j (142 mg, 39% yield) as an off-white solid. $^1$HNMR (500 MHz, DMSO-$d_6$) δ ppm: 8.2 (s, 1H), 7.85-7.65 (brs, 2H), 4.9 (m, 1H), 3.7 (s, 3H), 3.3-3.2 (m, 1H), 2.4 (m, 1H), 2.3-2.2 (m, 3H), 2.1 (m, 1H), 1.9 (m, 1H): Mass (m/z): 280.4 (M+H).

Example 6—Preparation of (1R,3R)-3-(6-amino-2-fluoro-9H-purin-9-yl)-N-(benzyloxy)cyclopentanecarboxamide (Compound 11j)

Compound 9j (140 mg, 0.5012 mmoles) and O-benzylhydroxylamine hydrochloride (160 mg, 1.002 mmoles) were dissolved in anhydrous tetrahydrofuran (5 mL) and cooled to −78 deg C. under argon. Lithium hexamethyldisilazide (LiHMDS, 1.4M in tetrahydrofuran, 1.1 mL, 1.553 mmoles) was slowly added to the solution with stirring. After stirring for 2 hours at −78 deg C., the reaction was quenched with saturated aqueous NH$_4$Cl solution (15 mL). The aqueous phase was extracted with ethyl acetate (3×15 mL) and the combined organic layers were dried over anhydrous sodium sulfate, filtered and concentrated to dryness. The residue was purified on basic alumina (5% methanol in dichloromethane) giving compound 11j (39 mg, 21% yield) as a white solid. Mass (m/z): 371.5 (M+H).

Example 7—Preparation of (1R,3R)-3-(6-amino-2-fluoro-9H-purin-9-yl)-N-hydroxycyclopentanecarboxamide (Compound 10j)

Compound 11j (80 mg, 0.2162 mmoles) was dissolved in methanol (5 mL) and 20% palladium hydroxide on carbon (10 mg) was added. The reaction mixture was degassed under vacuum and stirred under a hydrogen atmosphere for 3 hours. The mixture was filtered through Celite and washed with methanol (10 mL). The filtrate was concentrated to dryness and the residue was triturated with ether (1 mL) giving compound 10j (24 mg, 39% yield) as an off-white solid. $^1$HNMR (500 MHz, DMSO-$d_6$) δ ppm: 8.2 (s, 1H), 7.85-7.65 (brs, 2H), 4.9 (m, 1H), 2.9-2.8 (m, 1H), 2.4 (m, 1H), 2.3-2.0 (m, 5H), 1.8 (m, 1H): Mass (m/z): 281.3 (M+H).

Examples 8-9—Preparation of Compound 10k

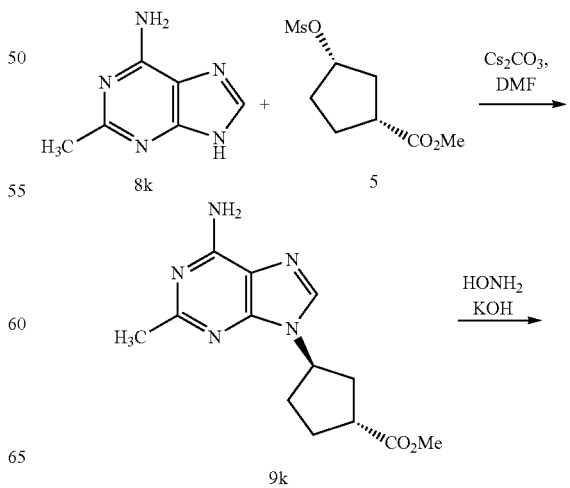

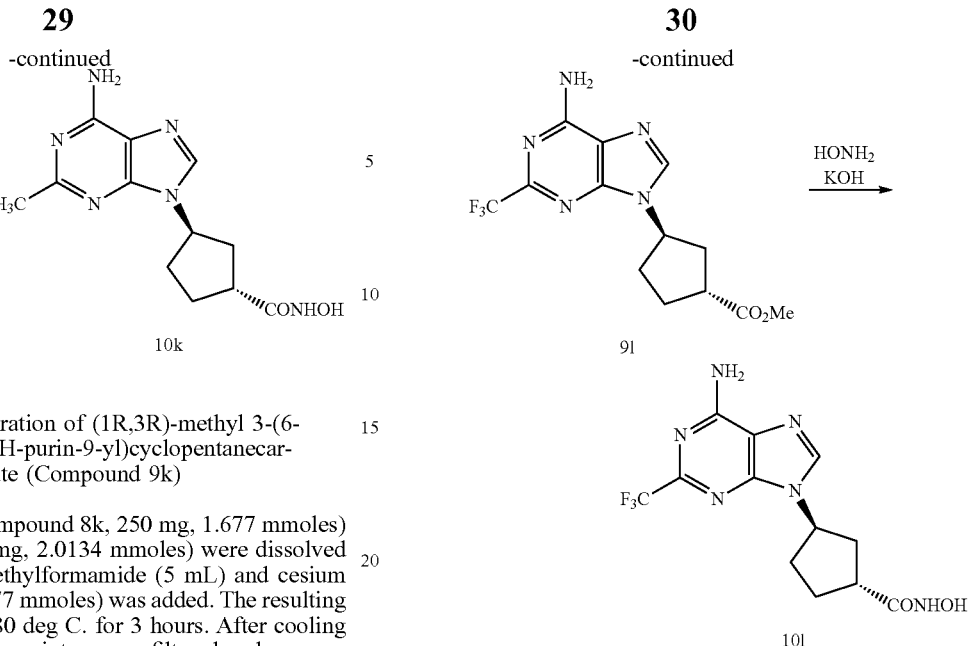

Example 8—Preparation of (1R,3R)-methyl 3-(6-amino-2-methyl-9H-purin-9-yl)cyclopentanecarboxylate (Compound 9k)

2-Methyladenine (compound 8k, 250 mg, 1.677 mmoles) and compound 5 (447 mg, 2.0134 mmoles) were dissolved in anhydrous N,N-dimethylformamide (5 mL) and cesium carbonate (547 mg, 1.677 mmoles) was added. The resulting mixture was stirred at 80 deg C. for 3 hours. After cooling to room temperature, the mixture was filtered and concentrated to dryness. The residue was purified on basic alumina (1% methanol in dichloromethane) giving compound 9k (162 mg, 35% yield) as a yellow solid. $^1$HNMR (500 MHz, DMSO-d$_6$) ☐ ppm: 8.15 (s, 1H), 7.1 (brs, 2H), 5.0-4.9 (m, 1H), 3.7 (s, 3H), 3.3-3.2 (m, 1H), 2.4 (s, 3H), 2.35 (m, 1H), 2.3-2.15 (m, 3H), 2.1-2.0 (m, 1H), 1.9 (m, 1H): Mass (m/z): 276.5 (M+H).

Example 9—Preparation of (1R,3R)-3-(6-amino-2-methyl-9H-purin-9-yl)-N-hydroxycyclopentanecarboxamide (Compound 10k)

Compound 9k (240 mg, 0.871 mmole) was dissolved in methanol (6 mL). Potassium hydroxide (1.46 g) was dissolved in methanol (7 mL). Hydroxylamine hydrochloride (1.15 g) was dissolved in methanol (10.5 mL). The potassium hydroxide solution was added to the hydroxylamine hydrochloride solution and the resulting mixture was stirred at 0 deg C. for 2 hours and then filtered. The hydroxylamine solution (6.8 mL, 0.95M in methanol, 6.468 mmoles) was slowly added to the compound 9k solution. The reaction was stirred at room temperature for 4 hours, after which it was concentrated to dryness. The residue was purified by preparative HPLC. Collected fractions were lyophilized. The residue was dissolved in methanol (5 mL) and treated with MP-carbonate resin (300 mg). After stirring for 2 hours, the resin was filtered and the filtrate was concentrated to dryness giving compound 10k (36 mg, 15% yield) as a white solid. $^1$HNMR (500 MHz, DMSO-d$_6$) δ ppm: 10.5 (brs, 1H), 8.8 (brs, 1H), 8.1 (s, 1H), 7.0 (brs, 2H), 4.9-4.8 (m, 1H), 2.9-2.8 (m, 1H), 2.4 (s, 3H), 2.3-2.0 (m, 5H), 1.8 (m, 1H); Mass (m/z): 277.4 (M+H).

Examples 10-11—Preparation of Compound 10l

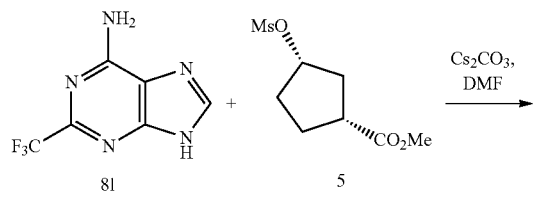

Example 10—Preparation of (1R,3R)-methyl 3-(6-amino-2-(trifluoromethyl)-9H-purin-9-yl)cyclopentanecarboxylate (Compound 9l)

2-Trifluoromethyladenine (compound 8l, 200 mg, 0.985 mmole) and compound 5 (284 mg, 1.28 mmole) were dissolved in anhydrous N,N-dimethylformamide (5 mL) and cesium carbonate (321 mg, 0.985 mmole) was added. The resulting mixture was stirred at 80 deg C. for 5 hours. After cooling to room temperature, the mixture was filtered and concentrated to dryness. The residue was purified on basic alumina (3% methanol in dichloromethane) giving compound 9l (176 mg, 41.7% yield) as an off-white solid. $^1$HNMR (500 MHz, DMSO-d$_6$) δ ppm: 8.5 (s, 1H), 7.9 (brs, 2H), 5.0 (m, 1H), 3.7 (s, 3H), 3.3-3.2 (m, 1H), 2.5-2.4 (m, 1H), 2.3-2.2 (m, 3H), 2.1 (m, 1H), 1.9 (m, 1H): Mass (m/z): 330.4 (M+H).

Example 11—Preparation of (1R,3R)-3-(6-amino-2-(trifluoromethyl)-9H-purin-9-yl)-N-hydroxycyclopentanecarboxamide (Compound 10l)

Compound 9l (170 mg, 0.516 mmole) was dissolved in methanol (5 mL). Potassium hydroxide (1.46 g) was dissolved in methanol (7 mL). Hydroxylamine hydrochloride (1.15 g) was dissolved in methanol (10.5 mL). The potassium hydroxide solution was added to the hydroxylamine hydrochloride solution and the resulting mixture was stirred at 0 deg C. for 2 hours and then filtered. The resulting hydroxylamine solution (4.03 mL, 0.95M in methanol, 3.831 mmoles) was slowly added to the compound 9l solution. The reaction was stirred at room temperature for 4 hours after which, it was concentrated to dryness. The residue was purified by preparative HPLC. Collected fractions were lyophilized. The residue was dissolved in methanol (5 mL) and treated with MP-carbonate resin (300 mg). After stirring for 2 hours, the resin was filtered and the filtrate was concentrated to dryness giving compound 10l (34 mg, 20% yield) as an off-white solid. $^1$HNMR (500 MHz, DMSO-d$_6$) δ ppm: 9.9 (brs, 1H), 9.7 (brs, 1H), 8.4 (s, 1H), 7.85 (brs, 2H), 5.01 (m, 1H), 2.84 (m, 1H), 2.3-2.05 (m, 5H), 1.9-1.8 (m, 1H); Mass (m/z): 331.4 (M+H).

Examples 12-13—Preparation of Compound 10m

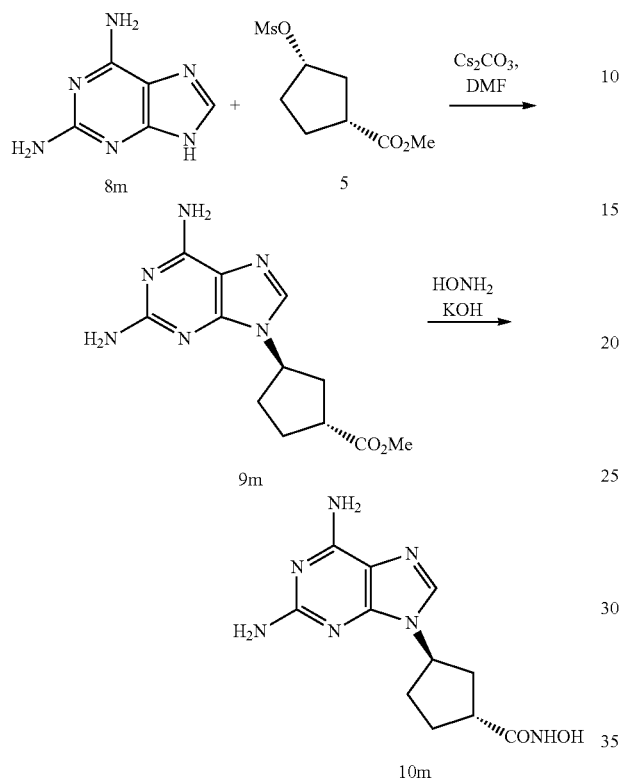

Example 12—Preparation of (1R,3R)-methyl 3-(2,6-diamino-9H-purin-9-yl)cyclopentanecarboxylate (Compound 9m)

2-Aminoadenine (compound 8m, 200 mg, 1.33 mmoles) and compound 5 (384 mg, 1.73 mmoles) were dissolved in anhydrous N,N-dimethylformamide (5 mL) and cesium carbonate (434 mg, 1.33 mmoles) was added. The resulting mixture was stirred at 80 deg C. for 5 hours. After cooling to room temperature, the mixture was filtered and concentrated to dryness. The residue was purified on basic alumina (5% methanol in dichloromethane) giving compound 9m (120 mg, 32.6% yield) as an off-white solid. $^1$HNMR (500 MHz, DMSO-$d_6$) δ ppm: 7.8 (s, 1H), 6.65 (brs, 2H), 5.8 (s, 2H), 4.8 (m, 1H), 3.7 (s, 3H), 3.2 (m, 1H), 2.4-2.2 (m, 2H), 2.2-2.1 (m, 2H), 1.9 (m, 2H): Mass (m/z): 277.3 (M+H).

Example 13—Preparation of (1R,3R)-3-(2,6-diamino-9H-purin-9-yl)-N-hydroxycyclopentanecarboxamide (Compound 10m)

Compound 9m (225 mg, 0.8146 mmole) was dissolved in methanol (5 mL). Potassium hydroxide (1.46 g) was dissolved in methanol (7 mL). Hydroxylamine hydrochloride (1.15 g) was dissolved in methanol (10.5 mL). The potassium hydroxide solution was added to the hydroxylamine hydrochloride solution and the resulting mixture was stirred at 0 deg C. for 2 hours and then filtered. The hydroxylamine solution (6.36 mL of a 0.95M solution in MeOH, 6.044 mmoles) was slowly added to the compound 9m solution. The reaction was stirred at room temperature for 4 hours after which, it was concentrated to dryness. The residue was purified by preparative HPLC. Collected fractions were lyophilized. The residue was dissolved in methanol (5 mL) and treated with MP-carbonate resin (250 mg). After stirring for 2 hours, the resin was filtered and the filtrate was concentrated to dryness giving compound 10m (56 mg, 25% yield) as a white solid. $^1$HNMR (500 MHz, DMSO-$d_6$) δ ppm: 10.5 (s, 1H), 8.8 (s, 1H), 7.8 (s, 1H), 6.6 (brs, 2H), 5.8 (brs, 2H), 4.9-4.8 (m, 1H), 2.9-2.8 (m, 1H), 2.3-2.0 (m, 6H); Mass (m/z): 278.2 (M+H).

Examples 14-15—Preparation of Compound 10n

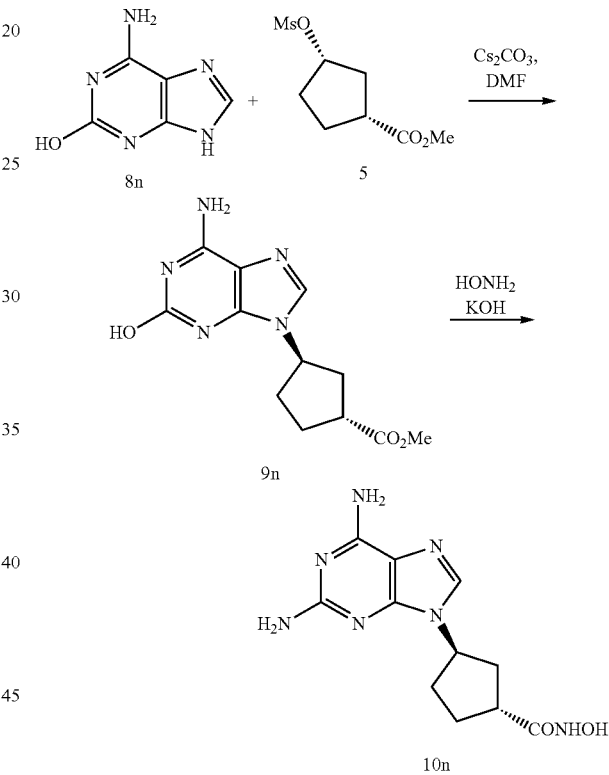

Example 14—Preparation of (1R,3R)-methyl 3-(6-amino-2-hydroxy-9H-purin-9-yl)cyclopentanecarboxylate (Compound 9n)

2-Hydroxyadenine (compound 8n, 1 g, 6.62 mmoles) and compound 5 (1.61 g, 7.28 mmoles) were dissolved in anhydrous N,N-dimethylformamide (20 mL) and cesium carbonate (2.15 mg, 6.62 mmoles) was added. The resulting mixture was stirred in a microwave reactor at 140 deg C. for 25 minutes. After cooling to room temperature, the mixture was filtered and concentrated to dryness. The residue was purified by preparative HPLC. Lyophilization of the pure fractions gave compound 9n (91 mg, 5% yield) as a white solid. $^1$HNMR (500 MHz, DMSO-$d_6$) δ ppm: 8.2 (s, 1H), 7.9 (brs, 2H), 5.4 (m, 1H), 3.6 (s, 3H), 3.0 (m, 1H), 2.2 (m, 5H), 1.9-1.8 (m, 1H): Mass (m/z): 278.3 (M+H).

Example 15—Preparation of (1R,3R)-3-(6-amino-2-hydroxy-9H-purin-9-yl)-N-hydroxycyclopentanecarboxamide (Compound 10n)

Compound 9n (70 mg, 0.2524 mmole) was dissolved in methanol (2 mL). Potassium hydroxide (1.46 g) was dissolved in methanol (7 mL). Hydroxylamine hydrochloride (1.15 g) was dissolved in methanol (10.5 mL). The potassium hydroxide solution was added to the hydroxylamine hydrochloride solution and the resulting mixture was stirred at 0 deg C. for 2 hours and then filtered. The hydroxylamine solution (1.97 mL of a 0.95M solution in MeOH, 1.8730 mmoles) was slowly to the compound 9n solution. The reaction was stirred at room temperature for 4 hours after which, it was concentrated to dryness. The residue was purified by preparative HPLC. Collected fractions were lyophilized. The residue was dissolved in methanol (2 mL) and treated with MP-carbonate resin (100 mg). After stirring for 2 hours, the resin was filtered and the filtrate was concentrated to dryness giving compound 10n (13 mg, 18% yield) as an off-white solid. $^1$HNMR (500 MHz, DMSO-$d_6$) δ ppm: 7.6 (s, 1H), 6.6 (brs, 2H), 5.3 (m, 1H), 3.0-2.9 (m, 1H), 2.7-2.6 (m, 1H), 2.0-1.6 (m, 5H), 1.2-1.05 (m, 1H); Mass (m/z): 279.4 (M+H).

Examples 16-17—Preparation of Compound 10o

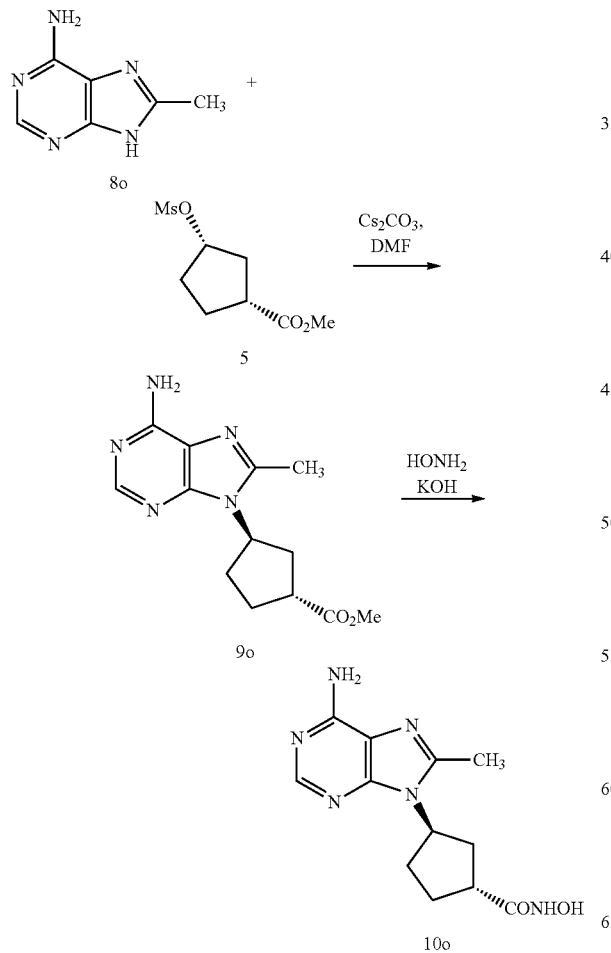

Example 16—Preparation of (1R,3R)-methyl 3-(6-amino-8-methyl-9H-purin-9-yl)cyclopentanecarboxylate (Compound 9o)

8-Methyladenine (compound 8o, 200 mg, 1.3409 mmoles) and compound 5 (387 mg, 1.743 mmoles) were dissolved in anhydrous N,N-dimethylformamide (5 mL) and cesium carbonate (437 mg, 1.3409 mmoles) was added. The resulting mixture was stirred at 80 deg C. for 5 hours. After cooling to room temperature, the mixture was filtered and concentrated to dryness. Purification on basic alumina (1% methanol in dichloromethane) gave compound 9o (130 mg, 35.2% yield) as an off-white solid. $^1$HNMR (500 MHz, DMSO-$d_6$) δ ppm: 8.1 (s, 1H), 7.0 (brs, 2H), 4.9 (m, 1H), 3.7-3.6 (s, 6H), 3.2 (m, 1H), 2.4-2.2 (m, 6H): Mass (m/z): 276.5 (M+H).

Example 17—Preparation of (1R,3R)-3-(6-amino-8-methyl-9H-purin-9-yl)-N-hydroxycyclopentanecarboxamide (Compound 10o)

Compound 9o (170 mg, 0.6152 mmole) was dissolved in methanol (5 mL). Potassium hydroxide (1.46 g) was dissolved in methanol (7 mL). Hydroxylamine hydrochloride (1.15 g) was dissolved in methanol (10.5 mL). The potassium hydroxide solution was added to the hydroxylamine hydrochloride solution and the resulting mixture was stirred at 0 deg C. for 2 hours and then filtered. The hydroxylamine solution (4.8 mL of a 0.95M solution in MeOH, 4.565 mmoles) was slowly added to the compound 9o solution. The reaction was stirred at room temperature for 4 hours after which, it was concentrated to dryness. The residue was purified by preparative HPLC. Collected fractions were lyophilized. The residue was dissolved in methanol (5 mL) and treated with MP-carbonate resin (250 mg). After stirring for 2 hours, the resin was filtered and the filtrate was concentrated to dryness giving compound 10o (37 mg, 22% yield) as a white solid. $^1$HNMR (500 MHz, DMSO-$d_6$) δ ppm: 10.5 (brs, 1H), 8.8 (brs, 1H), 8.1 (s, 1H), 7.0 (brs, 2H), 4.9-4.8 (m, 1H), 3.05-2.95 (m, 1H), 2.55 (s, 3H), 2.4 (m, 2H), 2.3-2.0 (m, 3H), 1.75 (m, 1H); Mass (m/z): 277.5 (M+H).

Examples 18-20—Preparation of Compound 10p

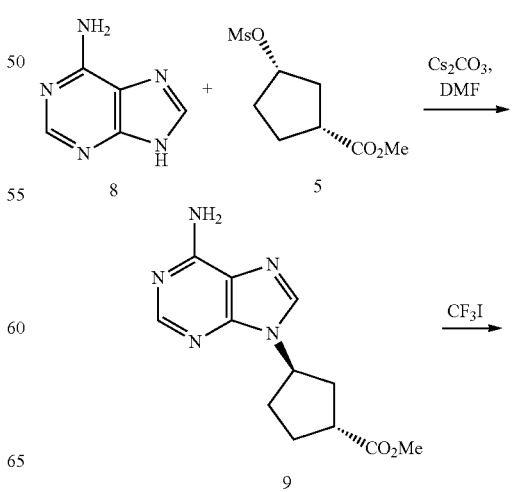

-continued

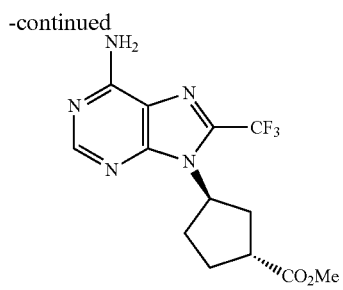

9p

↓ HONH₂ KOH

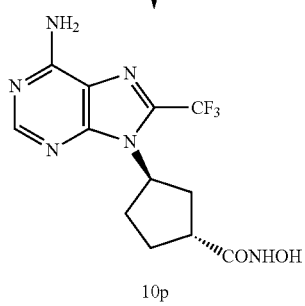

10p

Example 18—Preparation of (1R,3R)-methyl 3-(6-amino-9H-purin-9-yl)cyclopentanecarboxylate (Compound 9)

Adenine (compound 8, 200 mg, 1.4814 mmoles) and compound 5 (362 mg, 1.6296 mmoles) were dissolved in anhydrous N,N-dimethylformamide (6 mL) and cesium carbonate (483 mg, 1.4814 mmoles) was added. The resulting mixture was stirred at 80 deg C. for 5 hours. After cooling to room temperature, the mixture was filtered and concentrated to dryness. Purification on basic alumina (3% methanol in dichloromethane) gave compound 9 (160 mg, 41.4% yield) as a white solid. ¹HNMR (500 MHz, DMSO-d₆) δ ppm: 8.25 (s, 1H), 8.15 (s, 1H), 7.2 (brs, 2H), 5.0-4.9 (m, 1H), 3.65 (s, 3H), 3.3-3.2 (m, 1H), 2.4-2.1 (m, 6H); Mass (m/z): 262.5 (M+H).

Example 19—Preparation of (1R,3R)-methyl 3-(6-amino-8-(trifluoromethyl)-9H-purin-9-yl)cyclopentanecarboxylate (Compound 9p)

Trifluoroiodomethane (3M in DMSO, 5 mL, 15 mmoles) was slowly added to a solution of compound 9 (500 mg, 1.913 mmoles) in anhydrous dimethylsulfoxide (10 mL) at room temperature. Iron(II) sulfate (1M in water, 2 mL, 2 mmoles) and 30% hydrogen peroxide solution in water (3 mL) were added. The resulting mixture was stirred at 40-50 deg C. for 2 hours. The reaction mixture was then diluted with ethyl acetate (30 mL) and water (20 mL) and the aqueous phase was extracted with ethyl acetate (3×30 mL). The combined organic extracts were washed with brine (75 mL), dried over anhydrous sodium sulfate, filtered and concentrated. The residue was purified by preparative HPLC. Collected fractions were lyophilized and the residue was de-salted on treatment with MP-carbonate resin (250 mg) in methanol (5 mL). After stirring at room temperature for 2 hours, the resin was removed by filtration and the filtrate was concentrated to dryness giving compound 9p (63 mg, 10% yield) as an off-white solid. ¹HNMR (500 MHz, DMSO-d₆) δ ppm: 8.25 (s, 1H), 7.3 (brs, 2H), 5.05 (m, 1H), 3.5 (s, 3H), 2.6-2.5 (m, 1H), 2.4-2.15 (m, 5H), 1.9-1.8 (m, 1H); Mass (m/z): 330.4 (M+H).

Example 20—Preparation of (1R,3R)-3-(6-amino-8-(trifluoromethyl)-9H-purin-9-yl)-N-hydroxycyclopentanecarboxamide (Compound 10p)

Compound 9p (120 mg, 0.364 mmole) was dissolved in methanol (6 mL). Potassium hydroxide (1.46 g) was dissolved in methanol (7 mL). Hydroxylamine hydrochloride (1.15 g) was dissolved in methanol (10.5 mL). The potassium hydroxide solution was added to the hydroxylamine hydrochloride solution and the resulting mixture was stirred at 0 deg C. for 2 hours and then filtered. The hydroxylamine solution (2.84 mL of a 0.95M solution in MeOH, 2.7 mmoles) was slowly added to the compound 9p solution. The reaction was stirred at room temperature for 4 hours after which, it was concentrated to dryness. The residue was purified by preparative HPLC. Collected fractions were lyophilized. The residue was dissolved in methanol (5 mL) and treated with MP-carbonate resin (250 mg). After stirring for 2 hours, the resin was filtered and the filtrate was concentrated to dryness giving compound 10p (23 mg, 19% yield) as an off-white solid. ¹HNMR (500 MHz, DMSO-d₆) δ ppm: 10.6 (brs, 1H), 8.9 (brs, 1H), 8.25 (s, 1H), 7.8-7.7 (brs, 2H), 5.1-5.0 (m, 1H), 3.05 (m, 1H), 2.6 (m, 2H), 2.3-2.1 (m, 3H), 1.8 (m, 1H); Mass (m/z): 331.4 (M+H).

Examples 21-22—Preparation of Compound 10q

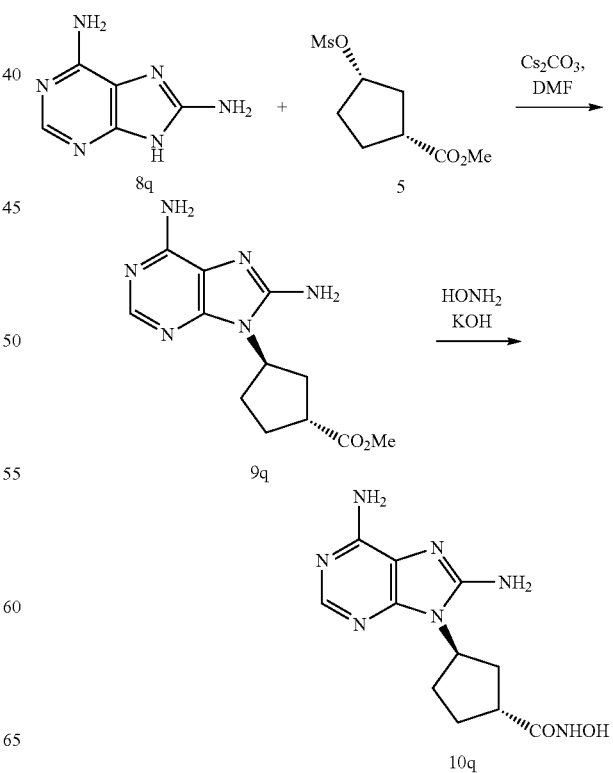

Example 21—Preparation of (1R,3R)-methyl 3-(6,8-diamino-9H-purin-9-yl)cyclopentanecarboxylate (Compound 9q)

8-Amninoadenine (compound 8q, 200 mg, 1.33 mmoles) and compound 5 (325 mg, 1.46 mmoles) were dissolved in anhydrous N,N-dimethylformamide (5 mL) and cesium carbonate (434 mg, 1.33 mmoles) was added. The resulting mixture was stirred at 80 deg C. for 5 hours. After cooling to room temperature, the mixture was filtered and concentrated to dryness. The residue was purified on basic alumina (10% methanol in dichloromethane) giving compound 9q (88 mg, 24% yield) as a white solid. $^1$HNMR (500 MHz, DMSO-$d_6$) δ ppm: 7.85 (s, 1H), 6.4 (brs, 2H), 6.3 (brs, 2H), 4.85-4.75 (m, 1H), 3.65 (s, 3H), 2.4-2.2 (m, 4H), 2.1-2.0 (m, 1H), 1.8-1.6 (m, 2H): Mass (m/z): 277.4 (M+H).

Example 22—Preparation of (1R,3R)-3-(6,8-diamino-9H-purin-9-yl)-N-hydroxycyclopentanecarboxamide (Compound 10q)

Compound 9q (130 mg, 0.4706 mmole) was dissolved in methanol (5 mL). Potassium hydroxide (1.46 g) was dissolved in methanol (7 mL). Hydroxylamine hydrochloride (1.15 g) was dissolved in methanol (10.5 mL). The potassium hydroxide solution was added to the hydroxylamine hydrochloride solution and the resulting mixture was stirred at 0 deg C. for 2 hours and then filtered. The hydroxylamine solution (3.67 mL of a 0.95M solution in MeOH, 3.49 mmoles) was slowly added to the compound 9q solution. The reaction was stirred at room temperature for 4 hours, after which it was concentrated to dryness. The residue was purified by preparative HPLC. Collected fractions were lyophilized. The residue was dissolved in methanol (5 mL) and treated with MP-carbonate resin (250 mg). After stirring for 2 hours, the resin was filtered and the filtrate was concentrated to dryness giving compound 10q (20 mg, 16% yield) as an off-white solid. $^1$HNMR (500 MHz, DMSO-$d_6$) δ ppm: 9.38 (brs, 2H), 7.88 (s, 1H), 6.37 (brs, 2H), 6.32 (brs, 2H), 4.79 (m, 1H), 3.00 (m, 1H), 2.36-2.33 (m, 2H), 2.12-2.03 (m, 3H), 1.7 (m, 1H); Mass (m/z): 278.3 (M+H).

Examples 23-24—Preparation of Compound 10r

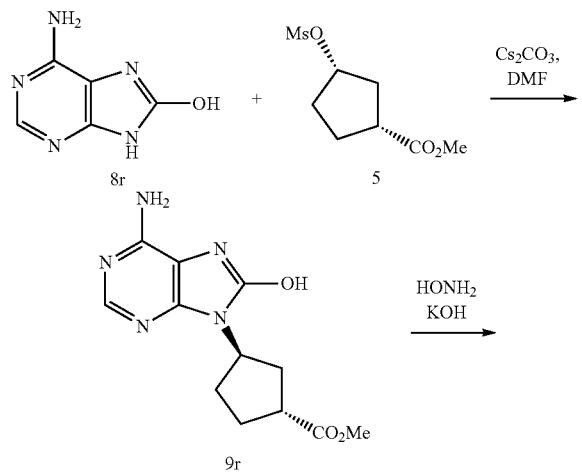

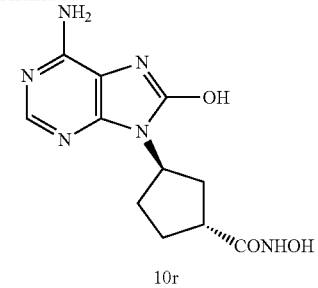

Example 23—Preparation of (1R,3R)-methyl 3-(6-amino-8-hydroxy-9H-purin-9-yl)cyclopentanecarboxylate (Compound 9r)

8-Hydroxyadenine (compound 8r, 200 mg, 1.32 mmoles) and compound 5 (323 mg, 1.45 mmoles) were dissolved in anhydrous N,N-dimethylformamide (5 mL) and cesium carbonate (431 mg, 1.324 mmoles) was added. The resulting mixture was stirred at 80 deg C. for 5 hours. After cooling to room temperature, the mixture was filtered and concentrated to dryness. The residue was purified by preparative HPLC. Collected fractions were lyophilized giving compound 9r (40 mg, 10.9% yield) as an off-white solid. $^1$HNMR (500 MHz, DMSO-$d_6$) δ ppm: 10.35 (brs, 1H), 8.1 (s, 1H), 6.7-6.5 (brs, 2H), 4.8 (m, 1H), 3.65 (s, 3H), 3.3 (m, 1H), 2.35-2.3 (3, 1H), 2.2-2.05 (m, 3H), 2.0-1.95 (m, 1H), 1.8-1.7 (m, 1H); Mass (m/z): 278.4 (M+H).

Example 24—Preparation of (1R,3R)-3-(6-amino-8-hydroxy-9H-purin-9-yl)-N-hydroxycyclopentanecarboxamide (Compound 10r)

Compound 9r (130 mg, 0.540 mmole) was dissolved in methanol (5 mL). Potassium hydroxide (1.46 g) was dissolved in methanol (7 mL). Hydroxylamine hydrochloride (1.15 g) was dissolved in methanol (10.5 mL). The potassium hydroxide solution was added to the hydroxylamine hydrochloride solution and the resulting mixture was stirred at 0 deg C. for 2 hours and then filtered. The hydroxylamine solution (4.22 mL of a 0.95M solution in MeOH, 4.013 mmoles) was slowly added to the compound 9r solution. The reaction was stirred at room temperature for 4 hours, after which it was concentrated to dryness. The residue was purified by preparative HPLC. Collected fractions were lyophilized. The residue was dissolved in methanol (5 mL) and treated with MP-carbonate resin (270 mg). After stirring for 2.5 hours, the resin was filtered and the filtrate was concentrated to dryness giving compound 10r (19.5 mg, 13% yield) as an off-white solid. $^1$HNMR (500 MHz, DMSO-$d_6$) δ ppm: 10.43 (brs, 1H), 8.77 (brs, 1H), 8.00 (s, 1H), 6.47 (brs, 2H), 4.82 (m, 1H), 2.90 (m, 1H), 2.35-2.15 (m, 2H), 2.1-1.85 (m, 3H), 1.7 (m, 1H); Mass (m/z): 279.5 (M+H).

Examples 25-45—Preparation of Compound 33

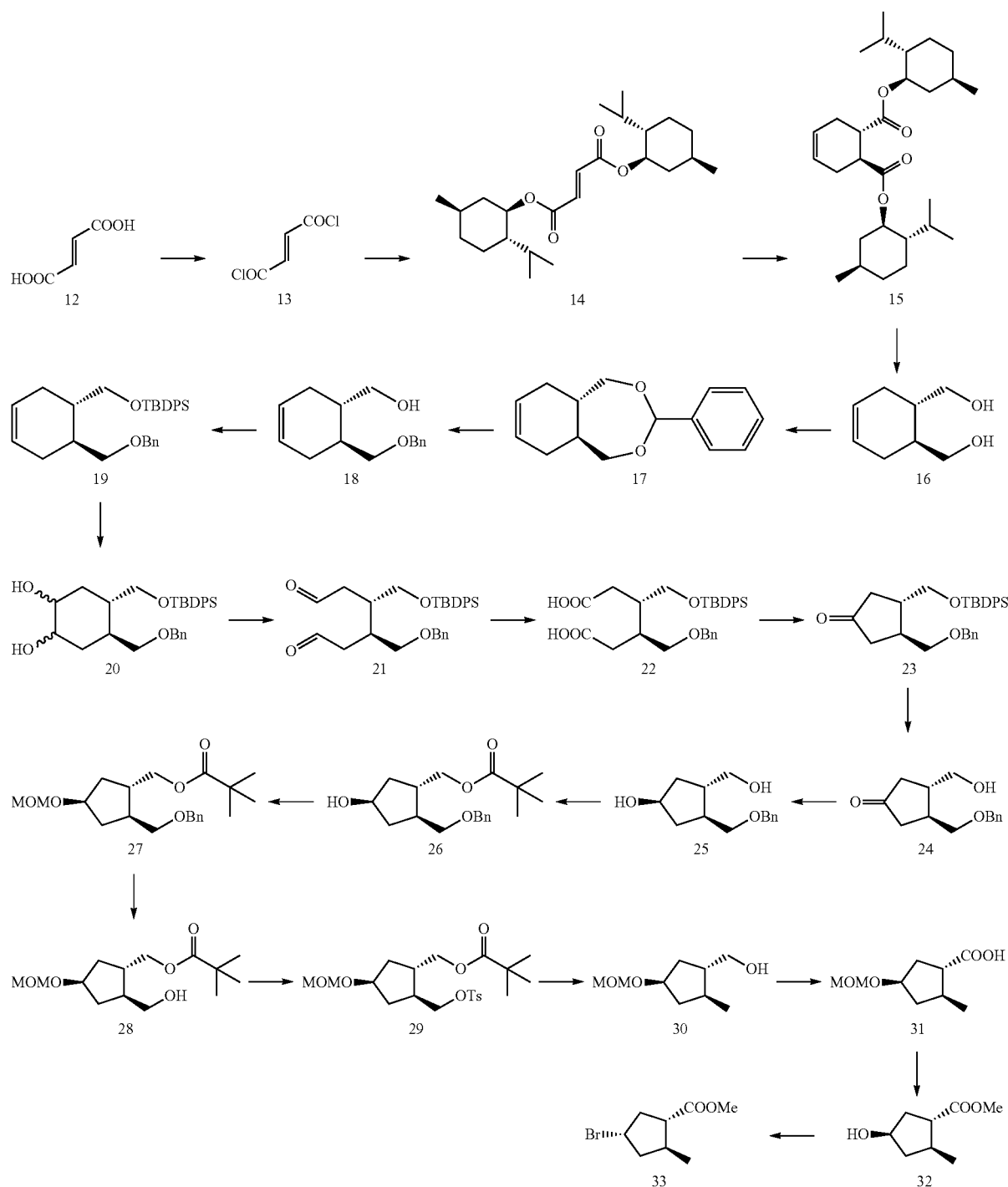

Example 25—Preparation of Fumaroyl Chloride (Compound 13)

Fumaric acid (compound 12, 120 g, 1.0338 moles) was combined with thionyl chloride (475 mL, 6.513 moles) and ferric chloride (1.2 g). The resulting mixture was heated to reflux for 4 hours, after which the reaction was concentrated to dryness. The residue was fractionally distilled (10 mm Hg, bath temp 100-110 deg C., vapor temp 60-70 deg C.) giving fumaroyl chloride (compound 13, 120 g, 76% yield) as a light-yellow liquid. Mass (m/z): 154.3 (M+H).

Example 26—Preparation of L-Menthyl Fumarate (Compound 14)

L-Menthol (103.6 g, 0.6635 mole) was dissolved in toluene (330 mL) and cooled to −20 deg C. under Argon. Fumaroyl chloride (compound 13, 50 g, 0.326 mole) was added followed by the addition of DIPEA (125.2 mL, 0.7191 mole) over 30 minutes. DMAP (1.99 g, 16.3 mmoles) was added immediately and the dark slurry mixture was slowly warmed to 2 deg C. over 2 hours. On completion of the reaction, the mixture was cooled to −20 deg C. and quenched with 3% aqueous sodium chloride solution (396 mL). The layers were separated and the organic layer was washed with aqueous hydrochloric acid containing 5% sodium chloride (0.15M, 530 mL). The organic phase was dried over anhydrous sodium sulfate, filtered and concentrated to dryness. Purification on silica gel (3% ethyl acetate in hexane) gave L-menthyl fumarate (compound 14, 101 g, 79% yield) as a brown liquid. $^1$HNMR (500 MHz, CDCl$_3$) δ ppm: 6.83 (s, 2H), 4.80 (m, 2H), 2.03 (d, 2H), 1.87 (m, 2H), 1.70 (d. 4H), 1.48 (n, 4H), 1.05 (m, 4H), 0.91 (m, 14H), 0.76 (d, 6H); Mass (m/z): 393.4 (M+H); SOR: [α]$_D^{25}$ −99.58° (C=1.0 in CHCl$_3$).

Example 27—Preparation of (1S,2S)-Di-(−)-menthyl Cyclohex-4-ene-1,2-dicarboxylate (Compound 15)

L-Menthyl fumarate (35 g, 89.28 mmoles) was dissolved in anhydrous dichloromethane (756 mL) and cooled to −78 deg C. under argon. Diethylaluminum chloride (1M in hexane, 205 mL, 205.3 mmoles) was added drop-wise maintaining the temperature at −78 deg C. After stirring at −78 deg C. for 30 minutes, butadiene (77.8 mL, 892 mmoles) was added in a single batch. The reaction mixture was stirred at −40 deg C. for 24 hours. Upon completion, the reaction mixture was quenched with the slow addition of aqueous hydrochloric acid (0.16M, 2.352 L) at −40 deg C. The resulting mixture was extracted with dichloromethane (2×250 mL) and the combined organic layers were washed with 5% aqueous sodium bicarbonate solution (284 mL) and brine (284 mL). The organic layer was dried over anhydrous sodium sulfate, filtered and concentrated to dryness. Purification on silica gel (2% ethyl acetate in hexane) gave compound 15 (16.74 g, 42% yield) as a pale yellow liquid. $^1$HNMR (500 MHz, CDCl$_3$) δ ppm: 5.67 (m, 2H), 4.66 (td, 2H), 2.85 (m, 2H), 2.5-1.85 (m, 4H), 1.8-0.7 (m. 18H, menthyl), 0.89 (d, 6H), 0.88 (d, 6H), 0.73 (d, 6H); Mass (m/z): 447.5 (M+H); SOR: [α]$_D^{25}$ −28.5° (C=2.4 in CHCl$_3$).

Example 28—Preparation of (1S,2S)-cyclohex-4-ene-1,2-diyldimethanol (Compound 16)

Lithium aluminum hydride (4.3 g, 114.3 mmoles) was suspended in ether (593 mL) and cooled to −78 deg C. under argon. Compound 15 (30 g, 67.2 mmoles) was dissolved in ether (380 mL) and added drop-wise to the lithium aluminum hydride suspension at −78° C. The mixture was stirred at room temperature for 12 hours. Upon completion, the reaction mixture was cooled to −20 deg C. Water (9.3 mL) was added followed by aqueous sodium hydroxide solution (3M, 9.3 mL) and water (28 mL). The mixture was stirred at room temperature for 30 minutes. The resulting precipitate was filtered and the filtrate was concentrated to dryness. Purification on silica gel (80% ethyl acetate in hexane) gave compound 16 (9.24 g, 75% yield) as colorless crystals. $^1$HNMR (500 MHz, CDCl$_3$) δ ppm: 5.65 (m, 2H), 3.76-3.55 (m, 4H), 3.18 (s, 2H), 2.18-1.63 (m, 6H); Mass (m/z): 184.6 (M+H+ACN); SOR: [α]$_D^{25}$ +70.5° (C=1.4 in CHCl$_3$).

Example 29—Preparation of (5aS,9aS)-3-phenyl-1,5,5a,6,9,9a-hexahydrobenzo[e][1,3]dioxepine (Compound 17)

Compound 16 (14 g, 98.5 mmoles), benzaldehyde (30 mL, 295 mmoles) and pyridinium p-toluene sulfonate (4.95 g, 19.7 mmoles) were dissolved in toluene (823 mL). The resulting mixture was heated to reflux for 2 hours in a round bottom flask fitted with a Dean-Stark trap. Upon completion, the reaction mixture was concentrated to dryness. Purification on silica gel (5% ethyl acetate in hexane) gave compound 17 (16.33 g, 72% yield) as colorless crystals. $^1$HNMR (500 MHz, CDCl$_3$) δ ppm: 7.55-7.30 (m, 5H), 5.82 (s, 1H), 5.71 (m, 2H), 4.02-3.95 (m, 1H), 3.80-3.70 (m. 1H), 3.55 (n, 2H), 2.09-1.90 (n, 2H), 1.77-1.59 (m, 4H); Mass (m/z): 231.3 (M+H); SOR: [α]$_D^{25}$ +207.5° (C=1.77 in CHCl$_3$).

Example 30—Preparation of ((1S,6S)-6-(benzyloxymethyl)cyclohex-3-enyl)methanol (Compound 18)

Compound 17 (16 g, 69.56 mmoles) was dissolved in anhydrous toluene (197 mL) and cooled to 0 deg C. under argon. Diisobutylaluminumhydride (25% in toluene, 160 mL, 278.2 mmoles) was added dropwise and the resulting mixture was stirred at 0 deg C. for 2 hours. Upon completion, methanol (9 mL) was added followed by the slow addition of aqueous sodium hydroxide (3M, 65 mL). The resulting mixture was diluted with ether (180 mL) and the aqueous phase was extracted with ether (2×60 mL). The combined organic phases were washed with saturated aqueous ammonium chloride (110 mL), dried over anhydrous sodium sulfate, filtered and concentrated to dryness. Purification on silica gel (5% ethyl acetate in hexane) gave compound 18 (15.82 g, 98% yield) as a colorless solid. $^1$HNMR (500 MHz, CDCl$_3$) δ ppm: 7.3 (m, 5H), 5.58 (m, 2H), 4.52 (s, 2H), 3.75-3.65 (m, 1H), 3.55-3.45 (m. 3H), 2.05-1.6 (m, 6H); Mass (m/z): 233.2 (M+H); SOR: [α]$_D^{25}$ +60.25° (C=4 in EtOH).

Example 31—Preparation of (1S,6S)-6-(benzyloxymethyl)cyclohex-3-enyl)methoxy)(tert-butyl)diphenylsilane (Compound 19)

Compound 18 (14 g, 0.0603 mol) and imidazole (10.2 g, 0.1508 mol) were dissolved in anhydrous N,N-dimethylformamide (126 mL) and cooled to 0 deg C. under argon. Choro-tert-butyldiphenylsilane (16.2 mL, 0.0633 mol) was slowly added and reaction mixture was stirred at room temperature for 12 hours. Upon completion, the reaction mixture was partitioned between ether (80 mL) and saturated aqueous ammonium chloride solution (80 mL). The organic phase was washed with brine (50 mL), dried over anhydrous sodium sulfate, filtered and concentrated to dryness. Purification on silica gel (1% EtOAc in hexane) gave compound 19 (20.42 g, 72% yield) as a thick colorless liquid. $^1$HNMR (500 MHz, CDCl$_3$) δ ppm: 7.71-7.66 (m, 4H), 7.45-7.27 (m, 11H), 5.65 (s, 2H), 4.44 (s, 2H), 3.68 (m. 2H), 3.46 (m, 2H), 2.22-1.87 (m, 6H), 1.08 (s, 9H); Mass (m/z): 471.4 (M+H); SOR: [α]$_D^{25}$ −34.5° (C=2.85 in CHCl$_3$).

Example 32—Preparation of (4S,5S)-4-(benzyloxymethyl)-5-((tert-butyldiphenylsilyloxy)methyl)cyclohexane-1,2-diol (Compound 20)

Compound 19 (20 g, 42.55 mmoles) and N-methylmorpholine N-oxide (10.5 g, 90.2 mmoles) were dissolved in dichloromethane (820 mL). Osmium tetroxide (0.1M in carbon tetrachloride, 9.36 mL, 0.936 mmole) was slowly added. After stirring for 6 hours at room temperature, saturated aqueous $Na_2S_2O_5$ (300 mL) was added. The aqueous layers were separated and the aqueous layer was extracted with dichloromethane (2×50 mL). The combined organic phases were washed with saturated aqueous ammonium chloride solution (400 mL), dried over anhydrous sodium sulfate, filtered and concentrated to dryness. Purification on silica gel (50% ethyl acetate in hexane) gave compound 20 (13 g, 65% yield) as a brown liquid. $^1$HNMR (500 MHz, $CDCl_3$) δ ppm: 7.65 (m, 4H), 7.45-7.2 (m, 11H), 4.44 (m, 2H), 4.0 (s, 1H) 3.68 (m. 3H), 3.46 (m, 2H), 2.22-1.87 (m, 6H), 1.08 (s, 9H); Mass (m/z): 471.4 (M+H); SOR: +34.5° (C=2.85 in $CHCl_3$).

Example 33—Preparation of (3S,4S)-3-(benzyloxymethyl)-4-((tert-butyldiphenylsilyloxy)methyl)hexanedial (Compound 21)

Compound 20 (12.5 g, 24.8 mmoles) was dissolved in tetrahydrofuran (109 mL) and cooled to 0 deg C. Sodium periodate (0.75M in water, 66 mL, 496 mmoles) was added and the reaction was stirred at 0 deg C. for 2 hours. Upon completion, the mixture was diluted with 1% aqueous sodium bicarbonate solution (350 mL) and extracted with ether (4×130 mL). The combined organic phases were dried over anhydrous sodium sulfate, filtered and concentrated to dryness to give compound 21, which was used without further purification.

Example 34—Preparation of (3S,4S)-3-(benzyloxymethyl)-4-((tert-butyldiphenylsilyloxy)methyl)hexanedioic acid (Compound 22)

Compound 21 isolated from Example 33 was dissolved in acetonitrile (56 mL) and cooled to 0 deg C. Sodium phosphate monobasic (0.95M in water, 123.9 mL, 117 mmoles) was added followed by 30% hydrogen peroxide solution (9.1 mL, 80.4 mmoles) and $NaClO_2$ (1M in water, 70.4 mL, 70.4 mmoles). The resulting mixture was diluted with acetonitrile (407 mL) and vigorously stirred for 12 hours at room temperature. Upon completion, ether (270 mL) was added. The layers were separated and the aqueous phase was acidified with 1M aqueous hydrochloric acid to adjust the pH to 2-3. The resulting mixture was extracted with ether (4×90 mL). The combined in organic layers were washed with brine (200 mL), dried over anhydrous sodium sulfate, filtered and concentrated to dryness. The crude material was recrystallized from ether/hexane giving compound 22 (8.94 g, 67.5% yield, 2 steps) as a colorless solid. $^1$HNMR (500 MHz, $CDCl_3$) δ ppm: 7.68 (m, 3H), 7.45-7.2 (m, 12H), 4.39 (s, 2H), 3.7-3.6 (m, 2H), 3.52-3.47 (m. 2H), 2.6-2.35 (m, 6H), 1.07 (s, 9H); Mass (m/z): 535.4 (M+H); SOR: −4.95° (C=2.24 in MeOH).

Example 35—Preparation of (3S,4S)-3-(benzyloxymethyl)-4-((tert-butyldiphenylsilyloxy)methyl)cyclopentanone (Compound 23)

Compound 22 (12 g, 22.4 mmoles) was dissolved in acetic anhydride (124 mL). Sodium acetate (1.07 g) added and the reaction was rapidly heated to reflux for 1 hour. Upon completion, the reaction was cooled to room temperature and diluted with toluene (296 mL). The mixture was concentrated to dryness with azeotroping with toluene to remove residual acetic anhydride and acetic acid. The residue was purified on silica gel (4% ethyl acetate in hexane) giving compound 23 (8.14 g, 77% yield) as a brown liquid. $^1$HNMR (500 MHz, $CDCl_3$) δ ppm: 7.68-7.64 (m, 4H), 7.46-7.27 (m, 11H), 4.49 (s, 2H), 3.72-3.71 (m, 2H), 3.56-3.38 (m. 2H), 2.55-2.16 (m, 6H), 1.08 (s, 9H); Mass (m/z): 473.4 (M+H); SOR: +27.65° (C=4.2 in $CHCl_3$).

Example 36—Preparation of (3S,4S)-3-(benzyloxymethyl)-4-(hydroxymethyl)cyclopentanone (Compound 24)

Compound 23 (8 g, 16.9 mmoles) was dissolved in tetrahydrofuran (124 mL) and cooled to 0 deg C. Tetrabutylammonium fluoride (1M in tetrahydrofuran, 20.3 mL, 20.3 mmoles) was slowly added. The mixture was stirred at 0 deg C. for 30 minutes and then for 90 minutes at room temperature. Upon completion, the reaction was cooled to 0 deg C. and quenched on addition of 50% saturated aqueous ammonium chloride solution (100 mL). The aqueous phase was extracted with ethyl acetate (3×25 mL). The combined organic layers were washed with brine (75 mL), dried over anhydrous sodium sulfate, filtered and concentrated to dryness. Purification on silica gel (50% ethyl acetate in hexane) gave compound 24 (2.81 g, 71% yield) as a colorless oil. $^1$HNMR (500 MHz, $CDCl_3$) δ ppm: 7.35 (m, 5H), 4.58 (s, 2H), 3.72-3.44 (m, 4H), 2.51-2.39 (m. 2H), 2.09-1.98 (m, 2H), 2.42-2.25 (m, 2H); Mass (m/z): 235.2 (M+H); SOR: +62.90° (C=2.54 in $CHCl_3$).

Example 37—Preparation of (1S,3S,4S)-3-(benzyloxymethyl)-4-(hydroxymethyl)cyclopentanol (Compound 25)

Compound 24 (1 g, 4.27 mmoles) was dissolved in acetonitrile (120 mL) and cooled to −5 deg C. Anhydrous acetic acid (14.6 mL, 256.4 mmoles) was slowly added followed by the addition of sodium triactoxyborohydride (13.57 g, 64 mmoles) in a single batch. The reaction was stirred at room temperature for 24 hours. Upon completion, the reaction mixture was cooled to 0 deg C. followed by the successive addition of saturated aqueous ammonium chloride (153 mL), saturated aqueous sodium tartarate (184 mL), saturated aqueous sodium bicarbonate (260 mL) and ethyl acetate (153 mL). The resulting mixture was stirred at room temperature for 1 hour. The organic layer was separated and the aqueous layer was further extracted with ethyl acetate (2×50 mL). The combined organic phases were dried over anhydrous sodium sulfate, filtered and concentrated to dryness. Purification on silica gel (3% methanol in dichloromethane) gave compound 25 (807 mg, 80% yield) as colorless crystals. $^1$HNMR (500 MHz, $CDCl_3$) δ ppm: 7.3 (m, 5H), 4.51 (s, 2H), 4.19 (m, 1H), 3.7-3.52 (m. 2H), 3.45-3.35 (m, 2H), 3.1 (brs, 1H), 2.4-2.2 (m, 2H), 2.19-1.95 (m, 2H), 1.84-1.67 (m, 1H), 1.48-1.37 (m, 2H); Mass (m/z): 237.2 (M+H); SOR: −6.92° (C=0.95 in $CHCl_3$).

Example 38—Preparation of ((1S,2S,4R)-2-(benzyloxymethyl)-4-hydroxycyclopentyl)methyl pivalate (Compound 26)

Compound 25 (8.3 g, 35.1 mmoles) and DMAP (4.31 g, 35.1 mmoles) were dissolved in anhydrous dichloromethane (83 mL) and cooled to 0 deg C. under argon. Pivaloyl chloride (4.29 mL, 35.1 mmoles) was added dropwise and the reaction mixture was stirred at room temperature for 2 hours. Upon completion, the reaction mixture was concentrated to dryness. Purification of the residue on silica gel (30% ethyl acetate in hexane) gave compound 26 (7.79 g, 69.35% yield) as a colorless oil. $^1$HNMR (500 MHz, DMSO-$d_6$) δ ppm: 7.4-7.25 (m, 5H), 4.5 (m, 3H), 4.15 (m, 1H), 4.05 (m, 1H), 3.9 (m, 1H), 3.5-3.35 (m, 2H), 2.18 (m, 1H), 1.95-1.85 (m, 2H), 1.7-1.3 (m, 3H), 1.1 (s, 9H); Mass (m/z): 321.2 (M+H).

Example 39—Preparation of ((1S,2S,4R)-2-(benzyloxymethyl)-4-(methoxymethoxy)cyclopentyl) methyl pivalate (Compound 27)

Compound 26 (7 g, 21.8 mmoles) was dissolved in anhydrous dichloromethane (70 mL) and cooled to 0 deg C. under argon. Diisopropylethylamine (11.42 mL, 65.5 mmoles) was added followed by the dropwise addition of chloromethyl methylether (1.96 mL, 24.03 mmoles). The reaction mixture was stirred at room temperature for 2 hours. Upon completion, the reaction mixture was concentrated to dryness. Purification of the residue on silica gel (12% ethyl acetate in hexane) gave compound 27 (6.22 g, 78.35% yield) as a colorless oil. $^1$HNMR (500 MHz, DMSO-$d_6$) δ ppm: 7.4-7.25 (m, 5H), 4.65-4.6 (s, 2H), 4.5 (s, 2H), 4.15-3.85 (m, 3H), 3.45-3.4 (m, 2H) 3.2 (s, 3H), 2.18-1.78 (m, 4H), 1.6-1.4 (m, 2H), 1.1 (s, 9H); Mass (m/z): 365.3 (M+H).

Example 40—Preparation of ((1S,2S,4R)-2-(hydroxymethyl)-4-(methoxymethoxy)cyclopentyl) methyl pivalate (Compound 28)

Compound 27 (6.8 g, 18.6 mmoles) was dissolved in methanol (70 mL) and 20% palladium hydroxide on carbon (0.68 g) was added. The reaction mixture was degassed under vacuum and stirred under a hydrogen atmosphere for 4 hours. Upon completion, the mixture was filtered through Celite and washed with methanol (50 mL). The filtrate was concentrated to dryness and the residue was purified on silica gel (30% ethyl acetate in hexane) giving compound 28 (4.33 g, 85% yield) as a colorless oil. $^1$HNMR (500 MHz, DMSO-$d_6$) δ ppm: 4.55 (m, 3H), 4.15-4.02 (m, 2H), 3.9 (m, 1H) 3.45 (m, 1H), 3.25 (s, 3H), 3.15 (d, 1H), 2.1 (m, 1H), 1.9 (m, 1H), 1.85-1.7 (m, 2H), 1.6-1.5 (m, 1H), 1.48-1.4 (m, 1H), 1.1 (s, 9H); Mass (m/z): 275.3 (M+H).

Example 41—Preparation of ((1S,2S,4S)-4-(methoxymethoxy)-2-(tosyloxymethyl)cyclopentyl) methyl pivalate (Compound 29)

Compound 28 (4.7 g, 17.13 mmoles) was dissolved in anhydrous dichloromethane (50 mL) and cooled to 0 deg C. DMAP (2.1 g, 17.13 mmoles) and diisopropylethylamine (5.97 mL, 34.26 mmoles) were added followed by p-toluenesulfonyl chloride (4.9 g, 25.7 mmoles). After stirring for 2 hours at room temperature, the reaction mixture was concentrated to dryness. Purification of the residue on silica gel (20% ethyl acetate in hexane) gave compound 29 (5.79 g, 76% yield) as a colorless liquid. $^1$HNMR (500 MHz, DMSO-$d_6$) δ ppm: 7.8 (d, 2H), 7.48 (d, 2H), 4.55 (s, 2H), 4.15-4.05 (m, 2H), 3.95-3.85 (m, 3H), 3.15 (s, 3H), 2.4 (s, 3H), 2.05-1.9 (m, 3H), 1.8 (m, 1H), 1.5-1.4 (m, 2H), 1.1 (s, 9H); Mass (m/z): 446.3 (M+H$_2$O).

Example 42—Preparation of ((1S,2S,4R)-4-(methoxymethoxy)-2-methylcyclopentyl)methanol (Compound 30)

Lithium aluminum hydride (1.8 g, 47.6 mmoles) was suspended in ether (70 mL) and cooled to 0 deg C. Compound 29 (6.8 g, 15.8 mmoles) was dissolved in ether (70 mL) and added dropwise to the lithium aluminum hydride suspension. The mixture was stirred at room temperature for 2 hours and then cooled to 0 deg C. The reaction was quenched at 0 deg C. on addition of sodium sulfate decahydrate (6.8 g) with rapid stirring for 2 hours. The precipitate was filtered through Celite and washed with ether (3×50 mL). The combined filtrates were concentrated to dryness. The residue was purified on silica gel (30% ethyl acetate in hexane) giving compound 30 (1.92 g, 70% yield) as a pale-yellow oil. $^1$HNMR (500 MHz, DMSO-$d_6$) δ ppm: 4.55 (s, 2H), 4.45 (m, 1H), 3.95 (m, 1H), 3.4 (m. 1H), 3.35-3.3 (m, 4H), 2.1 (m, 1H), 1.75 (m, 1H), 1.65-1.5 (m, 3H), 1.2 (m, 1H), 1.0 (d, 3H); Mass (m/z): 175.2 (M+H).

Example 43—Preparation of (1S,2S,4R)-4-(methoxymethoxy)-2-methylcyclopentanecarboxylic acid (Compound 31)

Compound 30 (2 g, 11.4 mmoles) was dissolved in anhydrous dichloromethane (50 mL) and cooled to 0 deg C. under argon. Dess-martin periodinane (5.85 g, 13.7 mmoles) was added and the reaction was stirred at 0 deg C. for 3 hours. Upon completion, the reaction was quenched with saturated aqueous sodium bicarbonate solution (10 mL) combined with saturated aqueous $Na_2S_2O_3$ solution (10 mL). The layers were separated and the aqueous layer was further extracted with ethyl acetate (3×50 mL). The combined organic phases were dried over anhydrous sodium sulfate, filtered and concentrated to dryness giving the intermediate aldehyde.

The intermediate aldehyde was dissolved in tert-butanol (30 mL) and aqueous potassium permanganate solution (1M, 20 mL, 20 mmoles) was added. The reaction was stirred at room temperature for 1 hour after which, it was titrated with saturated aqueous $Na_2SO_3$ solution until the purple color was eliminated. The resulting brown precipitate was dissolved on titration with aqueous hydrochloric acid (1M) until the solution reached pH 2. The resulting mixture was then extracted with ethyl acetate (3×50 mL). The combined organic phases were dried over anhydrous sodium sulfate, filtered and concentrated to dryness. The crude isolated compound 31 (2 g) was used without further purification.

Example 44—Preparation of (1S,2S,4R)-methyl 4-hydroxy-2-methylcyclopentanecarboxylate (Compound 32)

Crude compound 31 (2 g) was dissolved in methanol (3 mL). Methanolic hydrochloric acid (2M, 12 mL) was added dropwise. Following addition, the reaction was stirred at room temperature for 2 hours. Upon completion, the reaction mixture was concentrated to dryness. Purification of the residue on silica gel (30% ethyl acetate in hexane) gave compound 32 (1.04 g, 58% yield) as a brown liquid. $^1$HNMR (500 MHz, DMSO-$d_6$) δ ppm: 4.65 (brs, 1H), 4.15 (m, 1H), 3.6 (s, 3H), 2.45 (m, 1H), 2.15-1.95 (m, 2H), 1.9-1.7 (m, 2H), 1.18-1.1 (m, 1H), 1.05 (d, 3H); Mass (m/z): 159.2 (M+H).

Example 45—Preparation of (1S,2S,4S)-methyl 4-bromo-2-methylcyclopentanecarboxylate (Compound 33)

Compound 32 (1.5 g, 9.48 mmoles) was dissolved in anhydrous dichloromethane (15 mL). The solution was cooled to −20 deg C. and carbon tetrabromide (6.29 g, 18.9 mmoles) was added with stirring. On dissolution of the carbon tetrabromide, triphenylphosphine (5.21 g, 19.9 mmoles) was added and the reaction was stirred at −20 deg C. for 4 hours. Upon completion, the reaction was partitioned between dichloromethane (30 mL) and saturated aqueous sodium bicarbonate solution (15 mL). The layers were separated and the aqueous phase was washed with dichloromethane (2×30 mL). The combined organic phases were washed with brine (25 mL), dried over anhydrous sodium sulfate, filtered and concentrated to dryness. Purification of the residue on silica gel (5% ethyl acetate in hexane) gave compound 33 (1.04 g, 50% yield) as a colorless liquid. $^1$HNMR (500 MHz, DMSO-$d_6$) δ ppm: 4.6 (m, 1H), 3.62 (s, 3H), 2.7-2.6 (m, 1H), 2.5-2.4 (m, 1H), 23-2.2 (m, 1H), 2.15-2.08 (m, 1H), 1.05 (d, 3H); Mass (m/z): 221.1 (M+H).

Examples 46-48—Preparation of Compound 10s

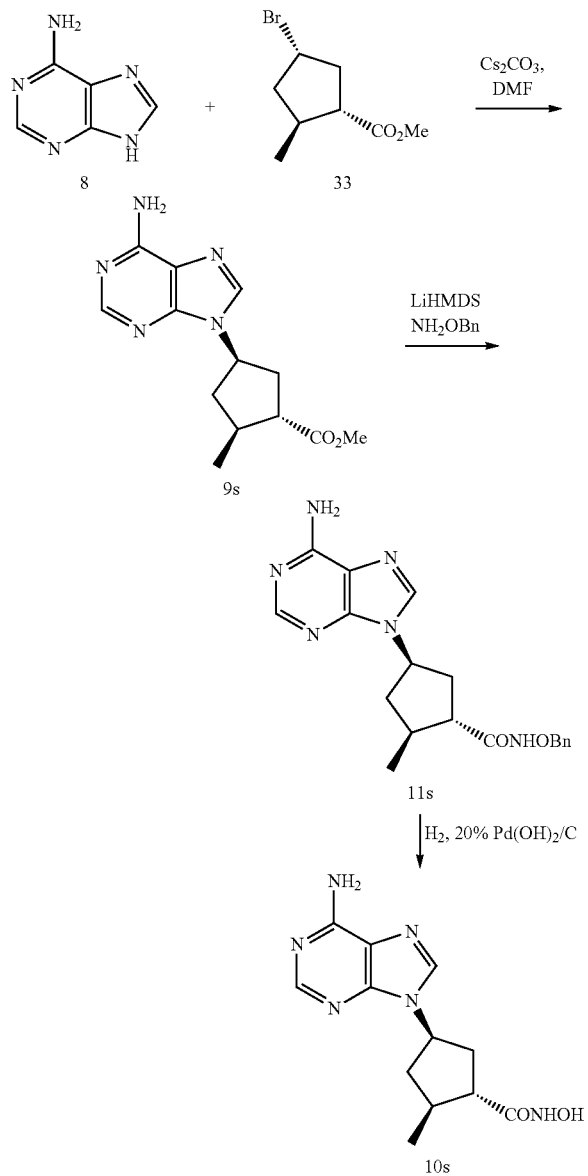

Example 46—Preparation of (1S,2S,4R)-methyl 4-(6-amino-9H-purin-9-yl)-2-methylcyclopentanecarboxylate (Compound 9s)

Adenine (compound 8, 184 mg, 1.3630 mmoles) and compound 33 (100 mg, 0.4543 mmole) were dissolved in anhydrous N,N-dimethylformamide (2 mL) and cesium carbonate (148 mg, 0.4543 mmole) was added. The resulting mixture was stirred in microwave reactor at 100 deg C. for 60 minutes. After cooling to room temperature, the mixture was filtered and the filtrate was concentrated to dryness. Purification of the residue on basic alumina (3% methanol in dichloromethane) gave compound 9s (50 mg, 40% yield) as an off-white solid. Mass (m/z): 276.2 (M+H).

Example 47—Preparation of (1S,2S,4R)-4-(6-amino-9H-purin-9-yl)-N-(benzyloxy)-2-methylcyclopentanecarboxamide (Compound 11s)

Compound 9s (50 mg, 0.1809 mmole) and O-benzylhydroxylamine hydrochloride (57.8 mg, 0.3619 mmole) were dissolved in anhydrous tetrahydrofuran (5 mL) and cooled to −78 deg C. Lithium hexamethyldisilazide (LiHMDS, 1.4M solution in THF, 0.4 mL, 0.5609 mmole) was added dropwise and the resulting mixture was stirred at −78 deg C. for 2 hours. Upon completion, the reaction was quenched with saturated aqueous ammonium chloride solution (10 mL). The layers were separated and the he aqueous phase was washed with ethyl acetate (3×15 mL). The combined organic layers were dried over anhydrous sodium sulfate, filtered and concentrated to dryness. The residue was purified on basic alumina (3% methanol in dichloromethane) giving compound 11s (40 mg, 60.3% yield) as a colorless solid. Mass (m/z): 367.3 (M+H).

Example 48—Preparation of (1S,2S,4R)-4-(6-amino-9H-purin-9-yl)-N-hydroxy-2-methylcyclopentanecarboxamide (Compound 10s)

Compound 11s (40 mg, 0.1091 mmole) was dissolved in methanol (4 mL) and 20% palladium hydroxide on carbon (10 mg) was added. The reaction mixture was degassed under vacuum and stirred under a hydrogen atmosphere for 2 hours. On completion, the reaction was filtered through Celite and washed with methanol (10 mL). The combined filtrates were concentrated to dryness and the residue was purified by preparative HPLC giving two isomers as TFA salts. The major isomer was treated with MP-carbonate resin (40 mg) in methanol (1 mL). After stirring at room temperature for 2 hours, the resin was removed by filtration and the filtrate was concentrated to dryness giving compound 10s (2 mg, 10% yield) as an off-white solid. Mass (m/z): 277.2 (M+H).

Examples 49-51—Preparation of Compound 10t

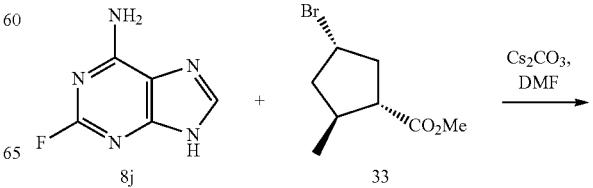

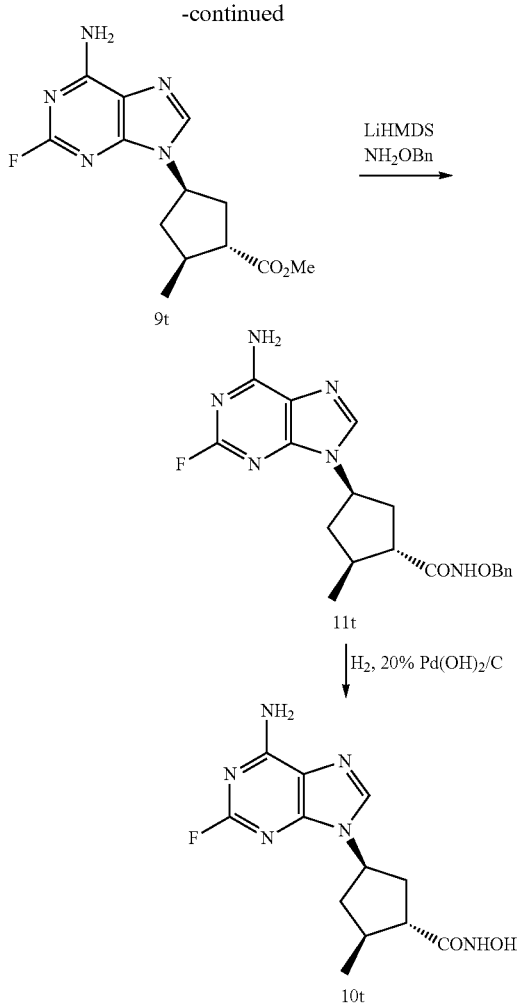

Example 49—Preparation of (1S,2S,4R)-4-(6-amino-9H-purin-9-yl)-N-hydroxy-2-methylcyclopentanecarboxamide (Compound 9t)

2-Fluoroadenine (compound 8j, 208 mg, 1.3630 mmoles) and compound 33 (100 mg, 0.4543 mmole) were dissolved in anhydrous N,N-dimethylformamide (2 mL) and cesium carbonate (148 mg, 0.4543 mmole) was added. The resulting mixture was stirred in microwave reactor at 100 deg C. for 50 minutes. After cooling to room temperature, the mixture was filtered and the filtrate was concentrated to dryness. Purification of the residue on basic alumina (5% methanol in dichloromethane) gave compound 9t (53 mg, 40% yield) as an off-white solid. Mass (m/z): 294.1 (M+H).

Example 50—Preparation of (1S,2S,4R)-4-(6-amino-2-fluoro-9H-purin-9-yl)-N-(benzyloxy)-2-methylcyclopentanecarboxamide (Compound 11t)

Compound 9t (50 mg, 0.1705 mmole) and O-benzylhydroxylamine hydrochloride (54.5 mg, 0.3411 mmole) were dissolved in anhydrous tetrahydrofuran (5 mL) and cooled to −78 deg C. Lithium hexamethyldisilazide (LiHMDS, 1.4M solution in THF, 0.37 mL, 0.5287 mmole) was added dropwise and the resulting mixture was stirred at −78 deg C. for 2 hours. Upon completion, the reaction was quenched with saturated aqueous ammonium chloride solution (10 mL). The layers were separated and the he aqueous phase was washed with ethyl acetate (3×15 mL). The combined organic layers were dried over anhydrous sodium sulfate, filtered and concentrated to dryness. The residue was purified on basic alumina (3% methanol in dichloromethane) giving compound 11t (41 mg, 62.5 mg) as a colorless solid. Mass (m/z): 385.3 (M+H).

Example 51—Preparation of (1S,2S,4R)-4-(6-amino-2-fluoro-9H-purin-9-yl)-N-(benzyloxy)-2-methylcyclopentanecarboxamide (Compound 10t)

Compound 11t (40 mg, 0.1040 mmole) was dissolved in methanol (4 mL) and 20% palladium hydroxide on carbon (10 mg) was added. The reaction mixture was degassed under vacuum and stirred under a hydrogen atmosphere for 2 hours. On completion, the reaction was filtered through Celite and washed with methanol (10 mL). The combined filtrates were concentrated to dryness and the residue was purified by preparative HPLC giving two isomers as TFA salts. The major isomer was treated with MP-carbonate resin (40 mg) in methanol (1 mL). After stirring at room temperature for 2 hours, the resin was removed by filtration and the filtrate was concentrated to dryness giving compound 10t (2.9 mg, 12.7% yield) as an off-white solid. Mass (m/z): 295.4 (M+H).

Examples 52-53—Preparation of Compound 8u

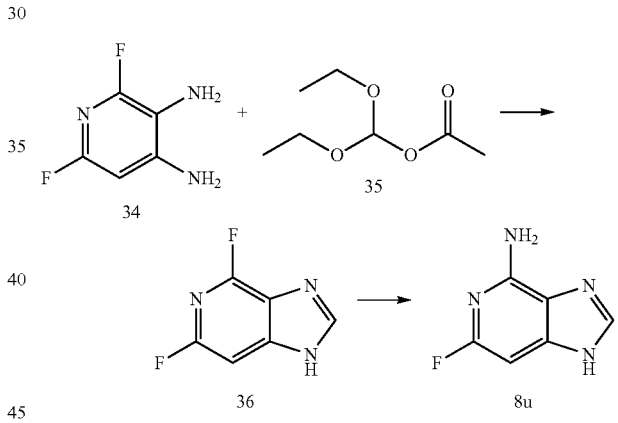

Example 52—Preparation of 4,6-difluoro-1H-imidazo[4,5-c]pyridine (Compound 36)

2,6-Difluoropyridine-3,4-diamine (compound 34, 1 g, 6.89 mmoles) and diethoxymethyl acetate (11.26 mL, 69.4 mmoles) were thoroughly combined in a round bottom flask. The solid mixture was heated to 100 deg C. for 1 hour. Upon completion, the reaction mixture was concentrated to dryness. The residue was purified on basic alumina (3% methanol in dichloromethane) giving compound 36 (908 mg, 85% yield) as a white solid. Mass (m/z): 156.1 (M+H). $^1$HNMR (500 MHz, DMSO-$d_6$) □ ppm: 13.4 (brs, 1H), 8.50 (s, 1H), 7.26 (s, 1H).

Example 53—Preparation of 6-fluoro-1H-imidazo[4,5-c]pyridin-4-amine (Compound 8u)

Compound 36 (1 g, 6.44 mmoles) was combined with ethanolic ammonia (10% w/v, 10 mL) and stirred in a microwave reactor at 130 deg C. for 90 minutes. After cooling to room temperature, the reaction mixture was concentrated to dryness. The residue was purified on basic alumina (5% methanol in dichloromethane) giving compound 8u (440 mg, 45% yield) as an off-white solid. $^1$HNMR (500 MHz, DMSO-$d_6$) δ ppm: 12.5 (s, 1H), 8.05 (s, 1H), 6.61 (s, 2H), 6.32 (s, 1H).

Examples 54-56—Preparation of Compound 10u

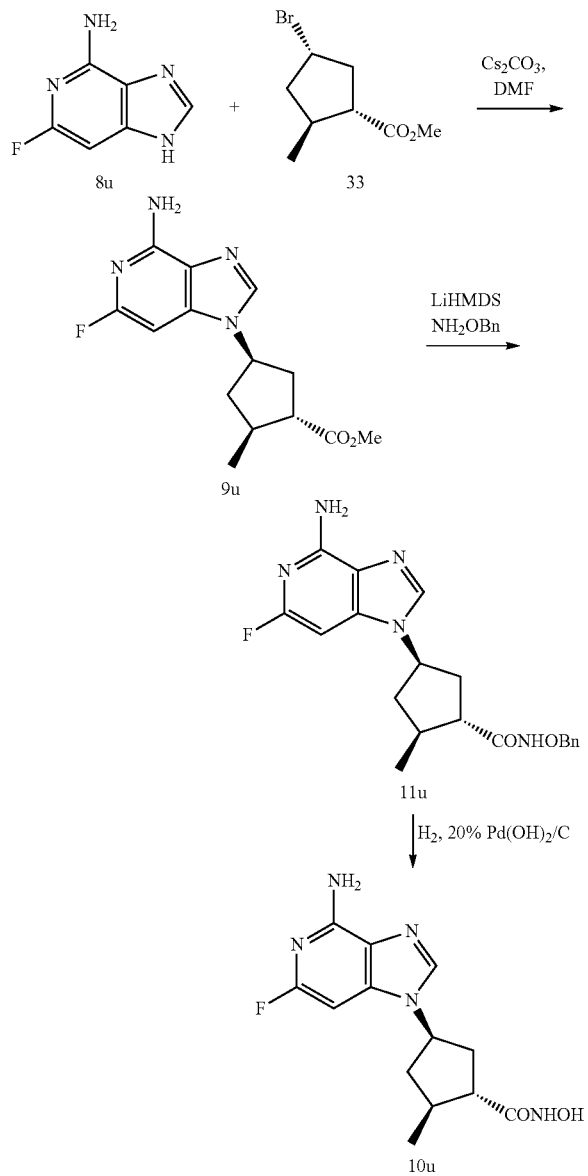

Example 54—Preparation of (1S,2S,4R)-methyl 4-(6-amino-2-fluoro-9H-purin-9-yl)-2-methylcyclopentanecarboxylate (Compound 9u)

Compound 8u (691 mg, 4.543 mmoles) and compound 33 (500 mg, 2.26 mmoles) were dissolved in anhydrous N,N-dimethylformamide (10 mL) and cesium carbonate (740 mg, 2.27 mmoles) was added. The resulting mixture was stirred in microwave reactor at 100 deg C. for 60 minutes. After cooling to room temperature, the mixture was filtered and the filtrate was concentrated to dryness. Purification of the residue on basic alumina (5% methanol in dichloromethane) gave compound 9u (500 mg, 37.6% yield) as an off-white solid. Mass (m/z): 293.2 (M+H).

Example 55—Preparation of (1S,2S,4R)-4-(6-amino-2-fluoro-9H-purin-9-yl)-N-(benzyloxy)-2-methylcyclopentanecarboxamide (Compound 11u)

Compound 9u (250 mg, 0.855 mmole) and O-benzylhydroxylamine hydrochloride (274 mg, 1.71 mmoles) were dissolved in anhydrous tetrahydrofuran (25 mL) and cooled to −78 deg C. Lithium hexamethyldisilazide (LiHMDS, 1.4M solution in THF, 1.85 mL, 2.65 mmoles) was added dropwise and the resulting mixture was stirred at −78 deg C. for 2 hours. Upon completion, the reaction was quenched with saturated aqueous ammonium chloride solution (40 mL). The layers were separated and the aqueous phase was washed with ethyl acetate (3×50 mL). The combined organic layers were dried over anhydrous sodium sulfate, filtered and concentrated to dryness. The residue was purified on basic alumina (5% methanol in dichloromethane) giving compound 11u (200 mg, 61% yield) as a colorless solid. Mass (m/z): 384.3 (M+H).

Example 56—Preparation of (1S,2S,4R)-4-(6-amino-2-fluoro-9H-purin-9-yl)-N-hydroxy-2-methylcyclopentanecarboxamide (Compound 10u)

Compound 11u (200 mg, 0.521 mmole) was dissolved in methanol (15 mL) and 20% palladium hydroxide on carbon (50 mg) was added. The reaction mixture was degassed under vacuum and stirred under a hydrogen atmosphere for 2 hours. On completion, the reaction was filtered through Celite and washed with methanol (40 mL). The combined filtrates were concentrated to dryness and the residue was purified by preparative HPLC giving two isomers as TFA salts. The major isomer was treated with MP-carbonate resin (200 mg) in methanol (5 mL). After stirring at room temperature for 2 hours, the resin was removed by filtration and the filtrate was concentrated to dryness giving compound 10u (30 mg, 19.7% yield) as an off-white solid. $^1$HNMR (500 MHz, DMSO-$d_6$) δ ppm: 10.6 (s, 1H), 8.95 (s, 1H), 8.21 (s, 1H), 6.72 (s, 2H), 6.41 (s, 1H), 4.95 (m, 1H), 2.32-2.42 (m, 3H), 2.03-2.21 (m. 2H), 1.71 (m, 1H), 1.05 (d, 3H); Mass (m/z): 294.2 (M+H). Purity by LC-MS: 99.4%.

Examples 57-59—Preparation of Compound 10v

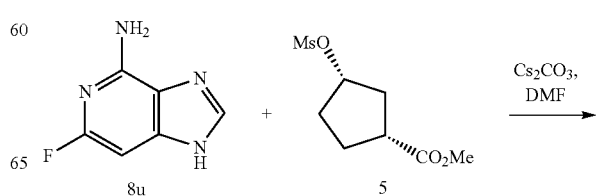

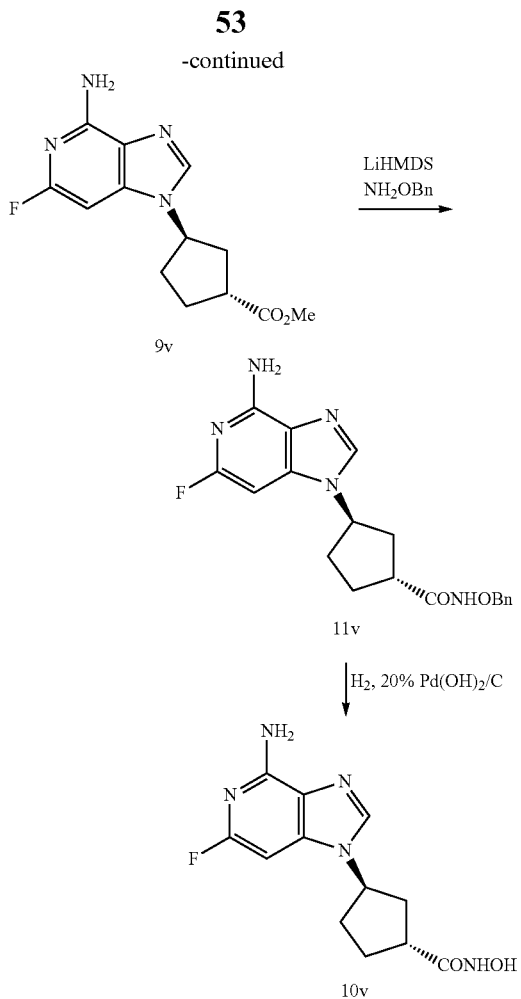

Example 57—Preparation of (1R,3R)-methyl 3-(4-amino-6-fluoro-1H-imidazo[4,5-c]pyridin-1-yl)cyclopentanecarboxylate (Compound 9v)

Compound 8u (68.5 mg, 0.4504 mmole) and compound 5 (50 mg, 0.2252 mmole) were dissolved in anhydrous DMF (2 mL). Cesium carbonate (73.4 mg, 0.2252 mmole) was added and the resulting mixture was stirred at 70 deg C. for 4 h. After cooling to room temperature, the mixture was filtered and the filter cake was washed with EtOAc (10 mL). The combined filtrates were concentrated to dryness under reduced pressure. The resulting residue was purified on basic alumina (5% methanol in dichloromethane) giving compound 9v (23.5 mg, 37.6% yield) as an off-white solid. Purity by LC-MS: 86.02% (Mass (m/z): 279.2 (M+H)).

Example 58—Preparation of (1R,3R)-3-(4-amino-6-fluoro-1H-imidazo[4,5-c]pyridin-1-yl)-N-(benzyloxy)cyclopentanecarboxamide (Compound 11v)

Compound 9v (30 mg, 0.1078 mmole) and O-benzylhydroxylamine hydrochloride (34.4 mg, 0.2156 mmole) were dissolved in anhydrous tetrahydrofuran (4 mL) and cooled to −78 deg C. Lithium hexamethyldisilazide (LiHMDS, 1.4 M in tetrahydrofuran, 0.23 mL, 0.3342 mmole) was slowly added and the reaction was stirred at −78 deg C. fir 2 hours. The reaction was quenched with saturated aqueous NH$_4$Cl (6 mL). The aqueous mixture was extracted with ethyl acetate (3×10 mL). The combined organic layers were dried over anhydrous sodium sulfate, filtered and concentrated to dryness. Purification on basic alumina (6% methanol in dichloromethane) gave compound 11v (19.9 mg, 50% yield) as a white solid. Purity by LC-MS: 93.90% (Mass (m/z): 370.3 (M+H)).

Example 59—Preparation of (1R,3R)-3-(4-amino-6-fluoro-1H-imidazo[4,5-c]pyridin-1-yl)-N-hydroxycyclopentanecarboxamide (Compound 10v)

Compound 11v (20 mg, 0.0541 mmole) was dissolved in methanol (3 mL). 20% palladium hydroxide on carbon (5 mg) was added. The reaction mixture was degassed under vacuum and stirred under a hydrogen atmosphere for 2 hours. Upon completion, the reaction mixture was filtered through Celite and the Celite pad was washed with methanol (40 mL). The combined filtrates were concentrated to dryness and the residue was purified by preparative HPLC giving two isomers as TFA salts. The major isomer was dissolved in methanol (5 mL) and treated with MP-carbonate resin (30 mg). After stirring at room temperature for 2 hours, the mixture was filtered and the filtrate was concentrated to dryness giving compound 10v (1.8 mg, 11.9% yield). Purity by LC-MS: 95.14%.

Examples 60-64—Preparation of Compound 38

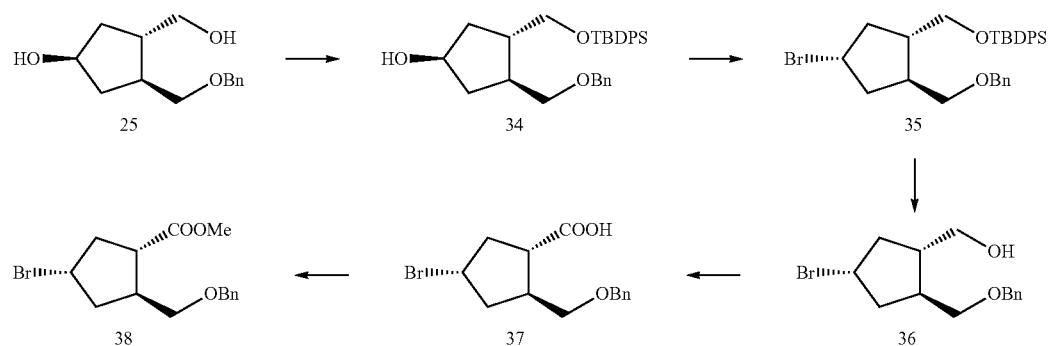

Example 60—Preparation of (1R,3S,4S)-3-(benzyloxymethyl)-4-((tert-butyldiphenylsilyloxy)methyl) cyclopentanol (Compound 34)

Compound 25 (Example 37, 1.5 g, 8.474 mmoles) and imidazole (1.94 g, 21.18 mmoles) were dissolved in anhydrous dichloromethane and cooled to −10 deg C. under argon. Chloro-tert-butyldiphenylsilane (1.78 mL, 8.89 mmoles) was added dropwise and the reaction was stirred at −10 deg C. for 2 hours. Upon completion, the reaction was quenched with saturated aqueous ammonium chloride solution (20 mL). The layers were separated and the aqueous phase was washed with dichloromethane (2×25 mL). The combined organic phases were washed with brine (30 mL), dried over anhydrous sodium sulfate, filtered and concentrated to dryness. Purification of the residue silica gel (20% ethyl acetate in hexane) gave compound 34 (2.13 g, 53% yield) as a thick colorless liquid. $^1$HNMR (500 MHz, CDCl$_3$) δ ppm: 7.65 (m, 4H), 7.50-7.25 (m, 11H), 4.55 (s, 2H), 4.2 (brs. 1H), 3.7 (m, 1H), 3.6 (m, 1H), 3.5 (s, 2H), 3.35 (d, 1H), 2.35 (m, 1H), 2.2-2.05 (m, 2H), 1.8-1.7 (m, 1H), 1.5 (m, 1H), 1.25 (m, 1H), 1.0 (s, 9H); Mass (m/z): 475.4 (M+H).

Example 61—Preparation of (((1S,2S,4S)-2-(benzyloxymethyl)-4-bromocyclopentyl)methoxy)(tert-butyl)diphenylsilane (Compound 35)

Compound 34 (5.2 g, 10.1 mmoles) was dissolved in anhydrous dichloromethane (60 mL) and carbon tetrabromide (6.71 g, 20.2 mmoles) was added. The mixture was cooled to −10 deg C. and triphenylphosphine (5.57 g, 21.2 mmoles) was added. The reaction was stirred at −10 deg C. for 4 hours. Upon completion, the reaction mixture was partitioned between dichloromethane (50 mL) and saturated aqueous sodium bicarbonate solution (25 mL). The layers were separated and the aqueous phase was washed with dichloromethane (2×50 mL). The combined organic layers were washed with brine (50 mL). dried over anhydrous sodium sulfate, filtered and concentrated to dryness. Purification of the residue on silica gel (10% ethyl acetate in hexane) gave compound 35 (3.53 g, 65% yield) as a colorless liquid. $^1$HNMR (500 MHz, CDCl$_3$) δ ppm: 7.65 (m, 4H), 7.45-7.25 (m, 11H), 4.5-4.4 (m, 2H), 4.35 (m. 1H), 3.8-3.7 (m, 2H), 3.5-3.3 (m, 2H), 2.5-2.35 (m, 2H), 2.25-1.9 (m, 4H), 1.05 (s, 9H); Mass (m/z): 539 (M+H).

Example 62—Preparation of (1S,2S,4R)-2-(benzyloxymethyl)-4-bromocyclopentyl)methanol (Compound 36)

Compound 35 (4.8 g, 8.95 mmoles) was dissolved in anhydrous tetrahydrofuran (80 mL) and cooled to 0 deg C. under argon. Tetrabutylammoniumfluoride (1M in tetrahydrofuran, 10.7 mL, 10.7 mmoles) was added dropwise. The resulting mixture was stirred at 0 deg C. for 30 minutes and at room temperature for 90 minutes. Upon completion, the reaction was cooled to 0 deg C. and quenched with 50% saturated aqueous ammonium chloride solution (50 mL). The layers were separated and the aqueous phase was washed with ethyl acetate (3×25 mL). The combined organic layers were washed with brine (50 mL), dried over anhydrous sodium sulfate, filtered and concentrated to dryness. Purification of the residue on silica gel (20% ethyl acetate in hexane) gave compound 36 (2.01 g, 75% yield) as a yellow liquid. $^1$HNMR (500 MHz, CDCl$_3$) δ ppm: 7.4-7.3 (m, 5H), 4.6 (s, 2H), 4.38 (m, 1H), 3.7-3.52 (m, 2H), 3.5 (m, 1H), 3.3 (m, 1H), 2.6-2.45 (m, 2H), 2.2 (m, 1H), 2.12-1.95 (m, 2H), 1.9-1.75 (m, 2H); Mass (m/z): 301.3 (M+H).

Example 63—Preparation of (1S,2S,4S)-2-(benzyloxymethyl)-4-bromocyclopentanecarboxylic acid (Compound 37)

Compound 36 (1.2 g, 4.02 mmoles) was dissolved in acetone (15 mL) and cooled to 0 deg C. Jones reagent (4 mL) was added dropwise and the resulting mixture was stirred for 1 hour maintaining the temperature below 20 deg C. Upon completion, the reaction was cooled to 0 deg C. and isopropanol (10 mL) was added. The resulting mixture was filtered and concentrated to dryness. The residue was diluted with ethyl acetate (50 mL), cooled to 0 deg C. and treated with aqueous hydrochloric acid solution (2M, 5 mL). The layers were separated and the aqueous phase was washed with ethyl acetate (2×30 mL). The combined organic phases were washed with brine, dried over anhydrous sodium sulfate, filtered and concentrated to dryness. Purification of the residue on silica gel (30% ethyl acetate in hexane) gave compound 37 (798 mg, 63.6% yield) as a colorless oil. $^1$HNMR (500 MHz, CDCl$_3$) δ ppm: 7.4-7.3 (m, 5H), 4.65-4.55 (m, 2H), 4.38 (m, 1H), 3.7-3.6 (m. 1H), 3.55-3.45 (m, 1H), 3.0-2.9 (m, 1H), 2.85-2.75 (m, 1H), 2.6-2.5 (m, 2H), 2.3-2.2 (m, 1H), 2.1-2.0 (m, 1H); Mass (m/z): 313.2 (M+H).

Example 64—Preparation of (1S,2S,4S)-methyl 2-(benzyloxymethyl)-4-bromocyclopentanecarboxylate (Compound 38)

Methanol (5 mL) was cooled to 0 deg C. under argon and acetyl chloride (0.27 mL, 3.84 mmoles) was added. After stirring for 5 minutes, Compound 37 (1 g, 3.2 mmoles) was added. The mixture was stirred at room temperature for 1 hour. Upon completion the reaction mixture was concentrated to dryness. Purification of the residue on silica gel (5% ethyl acetate in hexane) gave compound 38 (793 mg, 76% yield) as a colorless oil. $^1$HNMR (500 MHz, CDCl$_3$) δ ppm: 7.4-7.3 (m, 5H), 4.6-4.5 (s, 2H), 4.4-4.3 (m, 1H), 3.7 (s, 3H), 3.55 (d, 2H), 2.95-2.85 (m, 1H), 2.8-2.7 (m, 1H), 2.65-2.55 (m, 1H), 2.45-2.35 (m, 1H), 2.3-2.2 (m, 1H), 2.15-2.1 (m, 1H); Mass (m/z): 327.3 (M+H).

Examples 65-67—Preparation of Compound 10g and Compound 10h

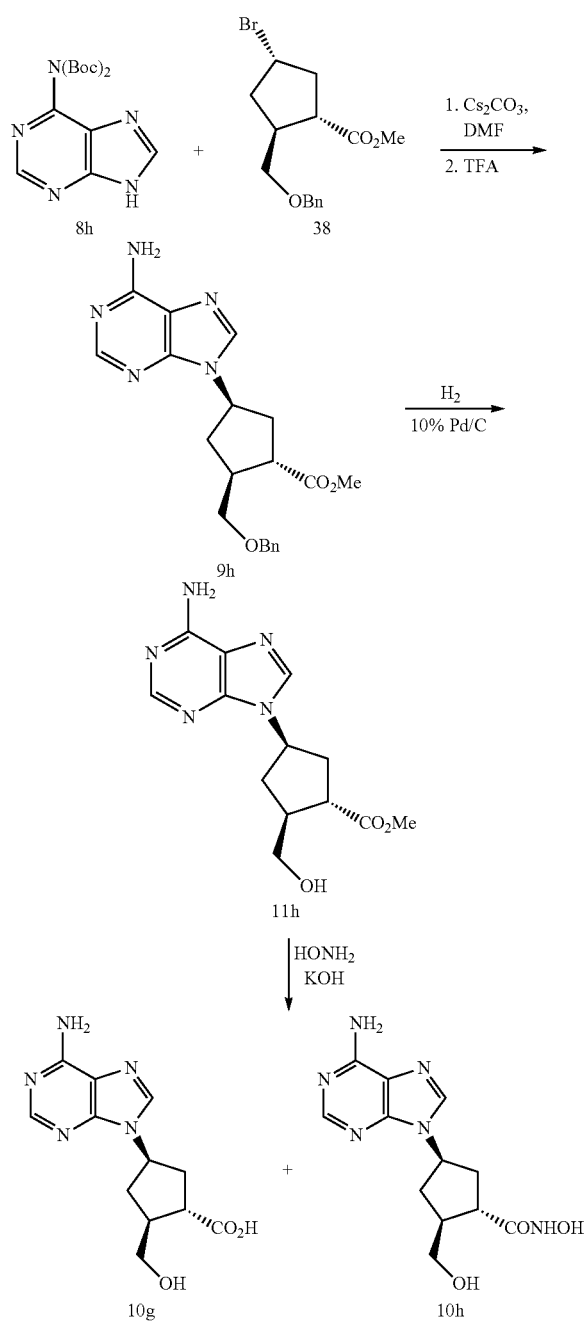

Example 65—Preparation of (1S,2S,4R)-methyl 4-(6-amino-9H-purin-9-yl)-2-(benzyloxymethyl)cyclopentanecarboxylate (Compound 9h)

Compound 8h (534 mg, 1.595 mmoles) and compound 38 (520 mg, 1.595 mmoles) were dissolved in anhydrous N,N-dimethylformamide (10 mL) and cesium carbonate (1.039 g, 3.190 mmoles) was added. The resulting mixture was stirred under nitrogen at 50 deg C. for 12 hours. After cooling to room temperature, the mixture was filtered and the solids were washed with ethyl acetate (2×15 mL). The combined filtrates were concentrated to dryness and the residue was suspended in anhydrous dichloromethane (15 mL). Trifluoracetic acid (3 mL) was added dropwise and the resulting mixture was stirred at room temperature for 2 hours. Upon completion, the mixture was concentrated to dryness and the residue was purified on basic alumina (3% methanol in dichloromethane) giving compound 9h (397 mg, 65% yield, 2 steps) as a colorless liquid. $^1$HNMR (500 MHz, CDCl$_3$) δ ppm: 8.35 (s, 1H), 7.9 (s, 1H), 7.4-7.3 (m, 5H), 5.8-5.7 (brs, 2H), 5.1 (m, 1H), 4.6-4.5 (s. 2H), 3.7 (s, 3H), 3.6 (m, 2H), 3.1 (m, 1H), 2.7-2.5 (m, 2H), 2.45-2.35 (m, 1H), 2.2-1.9 (m, 2H); Mass (m/z): 382.4 (M+H).

Example 66—Preparation of (1S,2S,4R)-methyl 4-(6-amino-9H-purin-9-yl)-2-(hydroxymethyl)cyclopentanecarboxylate (Compound 11h)

Compound 9h (200 mg, 0.5243 mmole) was dissolved in methanol (10 mL) and 10% palladium on carbon (80 mg) was added. Then the reaction mixture was degassed under vacuum and stirred under a hydrogen atmosphere (60 psi) for 2 days. Additional 10% palladium on carbon (30 mg) was added and the reaction was stirred under a hydrogen atmosphere (60 psi) for an additional 20 days. Upon completion, the reaction mixture was filtered through Celite and washed with methanol (30 mL). The combined filtrates were concentrated to dryness and the residue was purified on basic alumina (6% methanol in dichloromethane) giving compound 11h (114 mg, 75% yield) as a pale-yellow liquid. $^1$HNMR (500 MHz, DMSO-d$_6$) δ ppm: 8.3 (s, 1H), 8.15 (s, 1H), 7.2 (s, 2H), 5.0-4.85 (m, 1H), 4.8-4.7 (m, 1H), 3.7 (s, 3H), 3.6-3.4 (m. 2H), 3.0-2.9 (m, 1H), 2.45-2.2 (m, 4H), 2.0 (m, 1H); Mass (m/z): 292.4 (M+H).

Example 67—Preparation of (1S,2S,4R)-4-(6-amino-9H-purin-9-yl)-2-(hydroxymethyl)cyclopentanecarboxylic acid (Compound 10g) and (1S,2S,4R)-4-(6-amino-9H-purin-9-yl)-N-hydroxy-2-(hydroxymethyl)cyclopentanecarboxamide (Compound 10h)

Compound 11h (120 mg, 0.411 mmole) was dissolved in methanol (5 mL) and a freshly prepared solution of hydroxylamine (3.19 mL of a 0.95M solution in methanol, 16.11 mmoles) was slowly added. The reaction was stirred at room temperature for 2 hours, after which it was concentrated to dryness. The residue was purified by preparative HPLC giving two sets of fractions (13.79 minutes, compound 10g; 2.85 minutes, compound 10h). Each set of fractions were separately combined and lyophilized. The two residues were separately dissolved in methanol (5 mL) and treated with MP-carbonate resin (200 mg). After stirring for 2 hours, the mixtures were separately filtered and concentrated to dryness giving compound 10g (30 mg, 26.3% yield) and compound 10h (27 mg, 22.5% yield) as off-white solids.

Compound 10g analytical data: 98.47% purity by LC-MS; $^1$HNMR (500 MHz, DMSO-d$_6$) δ ppm: 12.3 (brs, 1H), 8.24 (s, 1H), 8.1 (s, 1H), 7.32 (s, 1H), 4.80 (brs, 2H), 3.53-3.42 (m. 4H), 2.74-2.72 (m, 1H), 2.32-2.2 (m, 4H), 2.0-1.94 (m, 1H); Mass (m/z): 278.4 (M+H).

Compound 10h analytical data: 97.17% purity by LC-MS. $^1$HNMR (500 MHz, DMSO-d$_6$) ☐ ppm: 8.24 (s, 1H), 8.1 (s, 1H), 7.32 (s, 1H), 7.17 (s, 1H), 6.8 (s, 1H), 4.94-4.90 (m, 1H), 3.52-3.44 (m. 2H), 2.76-2.74 (m, 1H), 2.32-2.2 (m, 4H), 2.0-1.94 (m, 1H); Mass (m/z): 293.4 (M+H).

Examples 68-79—Preparation of Compound 51

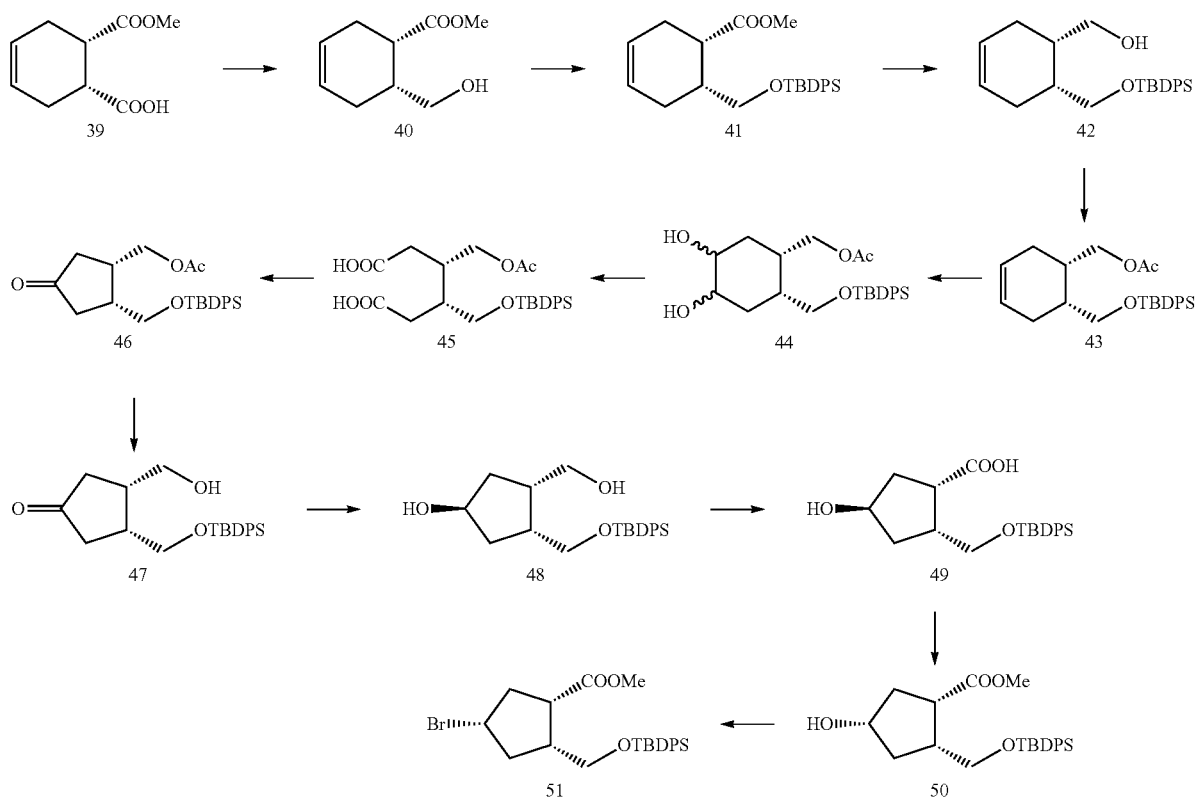

Example 68—Preparation of (1S,6R)-methyl 6-(hydroxymethyl)cyclohex-3-enecarboxylate (Compound 40)

Compound 39 (4 g, 21.71 mmoles) was dissolved in anhydrous diethyl ether (80 mL) and cooled to 0 deg C. under argon. Triethylamine (4.5 mL, 32.5 mmoles) followed by isobutylchloroformate (3.4 mL, 26.06 mmoles). After stirring at 0 deg C. for 30 minutes, the reaction was diluted with diethyl ether (50 mL) and washed with water (50 mL). The organic layer was dried over anhydrous sodium sulfate, filtered and concentrated to dryness. The residue was dissolved in tetrahydrofuran (80 mL) and water (16 mL) was added. The solution was cooled to 0 deg C. and sodium borohydride (1.64 g 43.35 mmoles) was added in portions. The reaction was stirred at 0 deg C. for 1 hour. Upon completion, the reaction was quenched with water (10 mL) at 0 deg C. The resulting mixture was extracted with ethyl acetate (2×70 mL). The combined organic extracts were dried over anhydrous sodium sulfate, filtered and concentrated to dryness giving compound 40 (3.5 grams, 94.8% yield), which was directly used in the next step without purification. $^1$HNMR (500 MHz, CDCl$_3$) δ ppm: 5.7 (s, 2H), 3.7 (s, 3H), 3.6-3.4 (m, 2H), 2.9-2.8 (m, 1H), 2.5-2.2 (m, 4H), 2.1-2.0 (m, 2H); Mass (m/z): 171.6 (M+H).

Example 69—Preparation of (1S,6R)-methyl 6-((tert-butyldiphenylsilyloxy)methyl)cyclohex-3-enecarboxylate (Compound 41)

Crude compound 40 (3.5 g, 20.58 mmoles) was dissolved in anhydrous dichloromethane (52 mL) and imidazole (3.5 g, 51.47 mmoles) was added. The resulting solution was cooled to −10 deg C. and choro-tert-butyldiphenylsilane (5.5 mL, 21.6 mmol) was slowly added. The reaction was stirred at −10 deg C. for 2 hours. Upon completion, the reaction was partitioned between dichloromethane (50 mL) and saturated aqueous ammonium chloride solution (40 mL). The layers were separated and the organic phase was washed with brine (50 mL), dried over anhydrous sodium sulfate, filtered and concentrated to dryness. The residue was purified on silica gel (2% ethyl acetate in hexane) giving compound 41 (4.75 grams, 54% yield, 2 steps) as a colorless liquid. $^1$HNMR (500 MHz, DMSO-d$_6$) δ ppm: 7.6 (m, 4H), 7.5-7.4 (m, 6H), 5.65-5.55 (m, 2H), 3.6-3.5 (m, 2H), 3.48 (s, 3H), 2.8 (m, 1H), 2.4 (m, 1H), 2.2-2.1 (m, 3H), 2.1-2.0 (m, 1H), 1.0 (s, 9H); Mass (m/z): 409.5 (M+H).

Example 70—Preparation of ((1S,6R)-6-((tert-butyldiphenylsilyloxy)methyl)cyclohex-3-enyl)methanol (Compound 42)

Compound 41 (4.7 g, 11.5 mmoles) was dissolved in anhydrous tetrahydrofuran (57 mL) and cooled to −78 deg C. under argon. Diisobutylaluminumhydride (DIBAL, 25% solution in toluene, 6.52 mL, 11.5 mmoles) was slowly added and the mixture was stirred at −78 deg C. for 2 hours. Upon completion, dichloromethane (9 mL) was added followed by aqueous sodium hydroxide solution (1M, 3 mL). After warming to room temperature, the mixture was extracted with dichloromethane (2×30 mL). The combined organic extracts were washed with saturate aqueous ammonium chloride solution (110 mL), dried over anhydrous sodium sulfate, filtered and concentrated to dryness. The residue was purified on silica gel (7% ethyl acetate in hexane) giving compound 42 (3.32 grams, 76% yield) as a pale-yellow liquid. $^1$HNMR (500 MHz, DMSO-d$_6$) δ ppm: 7.6 (m, 4H), 7.5-7.4 (m, 6H), 5.8 (brs, 1H), 5.6 (m, 2H), 4.35 (m, 1H), 3.7 (m, 1H), 3.6 (m, 1H), 3.4-3.3 (m, 1H), 3.25-3.2 (m, 1H), 2.1-1.9 (m, 5H), 1.0 (s, 9H); Mass (m/z): 381.5 (M+H).

Example 71—Preparation of ((1S,6R)-6-((tert-butyldiphenylsilyloxy)methyl)cyclohex-3-enyl)methyl acetate (Compound 43)

Compound 42 (5 g, 13.15 mmoles) was dissolved in anhydrous pyridine (10.7 mL) and cooled to 0 deg C. Acetic anhydride (10.7 mL) was slowly added and the mixture was stirred at room temperature for 3 hours. Upon completion, the reaction mixture was concentrated to dryness. The residue was purified on silica gel (3% ethyl acetate in hexane) giving compound 43 (5 grams, 90.5% yield) as a colorless liquid. $^1$HNMR (500 MHz, DMSO-$d_6$) δ ppm: 7.6 (m, 4H), 7.5-7.4 (m, 6H), 5.65-5.55 (m, 2H), 4.1-4.0 (m, 1H), 3.9-3.8 (m, 1H), 3.7 (m, 1H), 3.6 (m, 1H), 2.2 (m, 1H), 2.1-2.0 (m, 3H), 1.9 (s, 3H), 1.9-1.8 (m, 2H), 1.0 (s, 9H); Mass (m/z): 423.5 (M+H).

Example 72—Preparation of ((1S,2R)-2-((tert-butyldiphenylsilyloxy)methyl)-4,5-dihydroxycyclohexyl)methyl acetate (Compound 44)

Compound 43 (3.4 g, 8.056 mmoles) was dissolved in anhydrous dichloromethane (140 mL) and N-methylmorpholine N-oxide (2 g, 17.08 mmoles) was added. Osmium tetroxide (0.1M solution in carbon tetrachloride, 77 mL, 0.177 mmole) was added and the reaction was stirred at room temperature for 16 hours. Upon completion, saturated aqueous $Na_2S_2O_5$ solution (60 mL) was added. The layers were separated and the aqueous phase was further extracted with dichloromethane (2×30 mL). The combined organic phases were washed with saturated aqueous ammonium chloride solution (80 mL), dried over anhydrous sodium sulfate, filtered and concentrated to dryness. The residue was purified on silica gel (60% ethyl acetate in hexane) giving compound 44 (2.57 grams, 70% yield) as a brown liquid. $^1$HNMR (500 MHz, DMSO-$d_6$) δ ppm: 7.6 (m, 4H), 7.5-7.4 (m, 6H), 4.35-4.25 (m, 2H), 4.0-3.9 (m, 2H), 3.65-3.55 (m, 4H), 2.25-2.15 (m, 2H), 1.9 (s, 3H), 1.7-1.5 (m, 4H), 1.0 (s, 9H); Mass (m/z): 457.5 (M+H).

Example 73—Preparation of (3S,4R)-3-(acetoxymethyl)-4-((tert-butyldiphenylsilyloxy)methyl)hexanedioic acid (Compound 45)

Compound 44 (4 g, 8.771 mmoles) was dissolved in tetrahydrofuran (34 mL) and cooled to 0 deg C. Sodium periodate (0.75M aqueous solution, 23 mL, 17.54 mmoles) was added and the mixture was stirred at 0 deg C. for 2 hours. The resulting mixture was diluted with 1% aqueous sodium bicarbonate solution (120 mL) and washed with ether (4×40 mL). The combined organic phases were dried over anhydrous sodium sulfate, filtered and concentrated to dryness giving the expected crude bis-aldehyde intermediate.

The crude bis-aldehyde intermediate was dissolved in acetonitrile (18 mL) and cooled to 0 deg C. To this solution was added sodium phosphate dibasic (0.95M aqueous solution, 44 mL, 41.85 mmoles), 30% aqueous hydrogen peroxide solution (3.23 mL, 28.58 mmoles) and $NaClO_2$ (1M aqueous solution, 25 mL, 25.04 mmoles). The resulting mixture was diluted with acetonitrile (130 mL) and vigorously stirred at room temperature for 12 hours. Upon completion, the reaction was washed with ether (90 mL). The layers were separated and the pH of the aqueous phase was adjusted to 2-3 using 1M aqueous hydrochloric acid. The aqueous solution was washed with ether (4×30 mL). The combined organic extracts were washed with brine (70 mL), dried over anhydrous sodium sulfate, filtered and concentrated to dryness. The residue was recrystallized from ether/hexane giving compound 45 (3.07 grams, 72% yield, 2 steps) as a colorless solid. $^1$HNMR (500 MHz, DMSO-$d_6$) δ ppm: 12.2-12.05 (brs, 2H), 7.6 (m, 4H), 7.5-7.4 (m, 6H), 4.1 (m, 1H), 4.0 (m, 1H), 3.7-3.6 (m, 2H), 2.5-2.2 (m, 6H), 1.9 (s, 3H), 1.0 (s, 9H); Mass (m/z): 487.4 (M+H).

Example 74—Preparation of ((1S,2R)-2-((tert-butyldiphenylsilyloxy)methyl)-4-oxocyclopentyl) methyl acetate (Compound 46)

Compound 45 (2 g, 4.11 mmoles) was dissolved in acetic anhydride (21 mL) and sodium acetate (0.179 g) was added. The mixture was heated to reflux for 1 hour after which, it was cooled to room temperature. The resulting mixture was diluted with toluene (50 mL) and concentrated to dryness azeotropically removing the acetic anhydride. The residue was purified on silica gel (20% ethyl acetate in hexane) giving compound 46 (1.46 grams, 80% yield) as a colorless liquid. $^1$HNMR (500 MHz, DMSO-$d_6$) δ ppm: 7.6 (m, 4H), 7.5-7.4 (m, 6H), 4.2 (m, 2H), 3.8-3.6 (m, 2H), 2.8-2.7 (m, 1H), 2.6-2.5 (m, 1H), 2.4-2.3 (m, 2H), 2.2-2.1 (m, 2H), 1.9 (s, 3H), 1.0 (s, 9H); Mass (m/z): 447.4 (M+H).

Example 75—Preparation of (3R,4S)-3-((tert-butyldiphenylsilyloxy)methyl)-4-(hydroxymethyl)cyclopentanone (Compound 47)

Compound 46 (1.4 g, 3.301 mmoles) was dissolved in anhydrous methanol (20 mL) and sodium methoxide (178 mg, 3.301 mmoles) was added. The reaction was stirred at room temperature for 2 hours after which, it was quenched with acidic DOWEX resin. After stirring at room temperature for an additional 2 hours until the mixture reached pH=6, the mixture was filtered and the filtrate was concentrated to dryness giving compound 47 (0.98 grams, 77.7% yield) as a light brown liquid. $^1$HNMR (500 MHz, DMSO-$d_6$) δ ppm: 7.6 (m, 4H), 7.5-7.4 (m, 6H), 3.8-3.7 (m, 2H), 3.3-3.2 (m, 2H), 2.1-2.0 (m, 3H), 1.3-1.2 (m, 3H), 1.0 (s, 9H); Mass (m/z): 383.4 (M+H).

Example 76—Preparation of (1S,3R,4S)-3-((tert-butyldiphenylsilyloxy)methyl)-4-(hydroxymethyl)cyclopentanol (Compound 48)

Compound 47 (2.4 g, 6.282 mmoles) was dissolved in acetonitrile (288 mL) and cooled to −5 deg C. under argon. Anhydrous acetic acid (21.7 mL, 376.9 mmoles) was slowly added followed by addition of sodium triacetoxyborohydride (19.97 g, 94.24 mmoles) in a single batch. The mixture was stirred at room temperature for 24 hours after which, it was cooled to 0 deg C. Saturated aqueous ammonium chloride solution (375 mL) was added followed by saturated aqueous sodium tartarate solution (435 mL), saturated aqueous sodium bicarbonate solution (624 mL) and ethyl acetate (375 mL). The resulting mixture was stirred at room temperature for 1 hour. The layers were then separated and the aqueous layer was washed with ethyl acetate (2×100 mL). The combined organic phases were dried over anhydrous sodium sulfate, filtered and concentrated to dryness. The residue was purified on silica gel (80% ethyl acetate in hexane) giving compound 48 (1.69 grams, 70% yield) as a white solid. $^1$HNMR (500 MHz, DMSO-$d_6$) δ ppm: 7.6 (m, 4H), 7.5-7.4 (m, 6H), 4.35-4.25 (m, 2H), 4.15 (brs, 1H), 3.7 (m, 1H), 3.6 (m, 1H), 3.5-3.4 (m, 1H), 2.45-2.35 (m, 1H), 2.3-2.2 (m, 1H), 1.7-1.6 (m, 4H), 1.0 (s, 9H); Mass (m/z): 385.5 (M+H).

Example 77—Preparation of (1S,2R,4R)-2-((tert-butyldiphenylsilyloxy)methyl)-4-hydroxycyclopentanecarboxylic acid (Compound 49)

Compound 48 (1.1 g, 2.8645 mmoles) was dissolved in anhydrous acetonitrile (11 mL) and a solution of copper(I) triflate (108 mg, 0.2864 mmole) in acetonitrile (1 mL) was added followed by a solution of bipyridine (44.7 mg, 0.2864 mmole) in acetonitrile (1 mL), a solution of TEMPO (44.7 mg, 0.2864 mmole) in acetonitrile (1 mL) and a solution of N-methyl imidazole (47 mg, 0.5729 mmole) in acetonitrile (1 mL). The resulting dark brown mixture was rapidly stirred open to air and a color change from brown to green/blue was noted. The reaction was monitored by thin layer chromatography (40% ethyl acetate in hexane) until all starting material was consumed. Upon completion, the reaction was neutralized with 1N aqueous HCl, diluted with water (10 mL) and washed with dichloromethane (3×40 mL). The combined organic extracts were dried over anhydrous sodium sulfate, filtered and concentrated to dryness giving the required intermediate aldehyde (1.1 gram, crude isolate).

The intermediate aldehyde (1.1 g) was dissolved in tert-butanol (31 mL) and cooled to 0 deg C. An aqueous solution of sodium phosphate monobasic (20%, 28.16 mL) was added followed by 2-methyl-2-butene (28.16 mL) and the resulting mixture was stirred at 0 deg C. for 5 minutes. Sodium chlorite (2.77 g, 30.63 mmoles) was added and the reaction was stirred at room temperature for 5 hours. Upon completion, the reaction was concentrated to remove the volatile components. The residue was diluted with ethyl acetate (25 mL) and the resulting mixture was washed with brine (30 mL). The organic phase was dried over anhydrous sodium sulfate, filtered and concentrated to dryness. The isolated crude compound 49 (1 gram) was used without further purification. Mass (m/z): 397.3 (M+H).

Example 78—Preparation of (1S,2R,4R)-methyl 2-((tert-butyldiphenylsilyloxy)methyl)-4-Hydroxy-cyclopentanecarboxylate (Compound 50)

Crude compound 49 (1.8 g, 4.52 mmoles) was dissolved an anhydrous methanol (21.6 mL) and anhydrous toluene (32.4 mL) was added. Trimethylsilyl diazomethane (0.87M in hexane, 7.7 mL, 6.78 mmoles) was slowly added and the reaction was stirred at room temperature for 1 hour. Upon completion, the reaction mixture was concentrated to dryness. The residue was purified on silica gel (25% ethyl acetate in hexane) giving compound 50 (242 mg, 20.53% yield, 3 steps) as a colorless liquid. $^1$HNMR (500 MHz, DMSO-$d_6$) δ ppm: 7.6 (m, 4H), 7.5-7.4 (m, 6H), 4.6 (m, 1H), 4.25 (brs, 1H), 3.6-3.5 (m, 2H), 3.5 (s, 3H), 3.1 (m, 1H), 2.7-2.6 (m, 1H), 2.1-2.0 (m, 1H), 1.8-1.7 (m, 1H), 1.65-1.6 (m, 2H), 1.0 (s, 9H); Mass (m/z): 413.4 (M+H).

Example 79—Preparation of (1S,2R,4S)-methyl 4-bromo-2-((tert-butyldiphenylsilyloxy)methyl)cyclopentanecarboxylate (Compound 51)

Compound 50 (400 mg, 0.9701 mmole) was dissolved in anhydrous dichloromethane (6 mL) and cooled to −20 deg C. under argon. Carbon tetrabromide (643 mg, 1.940 mmoles) was added followed by triphenylphosphine (534 mg, 2.037 mmoles) and the resulting mixture was stirred at −20 deg C. for 4 hours. Upon completion, the reaction mixture was partitioned between dichloromethane (10 mL) and saturated aqueous sodium bicarbonate solution (10 mL). The layers were separated and the aqueous phase was washed with dichloromethane (2×10 mL). The combined organic layers were washed with brine (15 mL), dried over anhydrous sodium sulfate, filtered and concentrated to dryness. The residue was purified on silica gel (5% ethyl acetate in Hexane) giving compound 51 (276 mg, 60% yield) as a pale-yellow liquid. $^1$HNMR (500 MHz, DMSO-$d_6$) δ ppm: 7.6 (m, 4H), 7.5-7.4 (m, 6H), 4.3 (m, 1H), 3.7 (m, 1H), 3.6 (m, 1H), 3.5 (s, 3H), 3.0-2.9 (m, 1H), 2.5 (m, 2H), 2.4 (m, 1H), 2.3-2.2 (m, 1H), 2.0-1.9 (m, 1H), 1.0 (s, 9H); Mass (m/z): 475.2 (M+H).

Examples 80-83—Preparation of Compound 10i

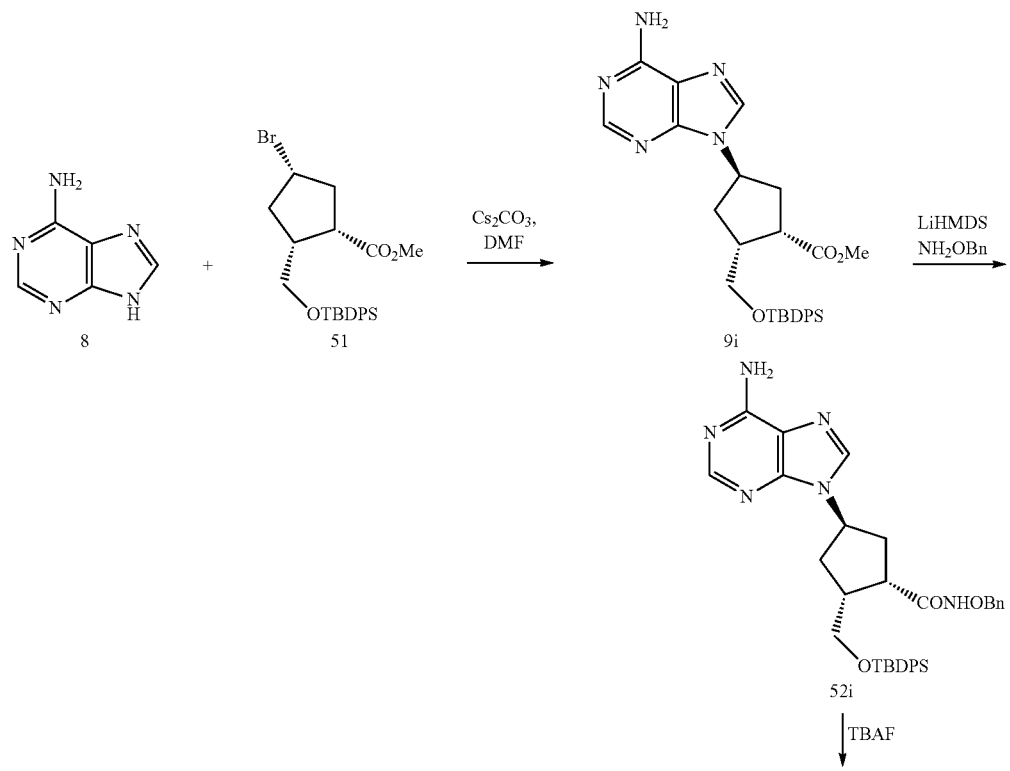

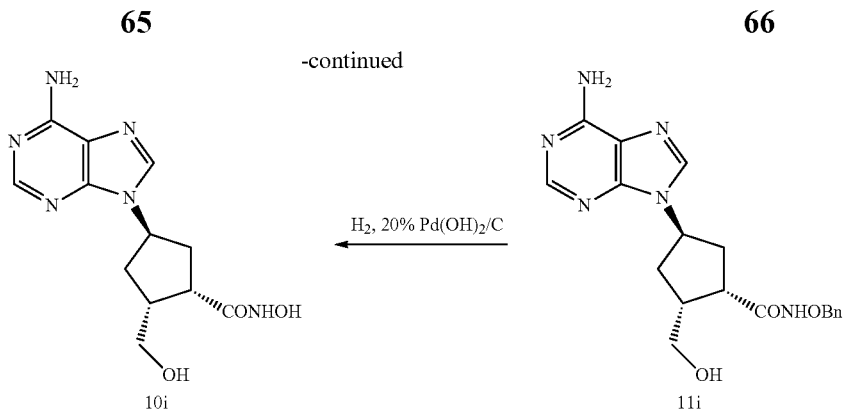

Example 80—Preparation of (1S,2R,4R)-methyl 4-(6-amino-9H-purin-9-yl)-2-((tert-butyldiphenylsilyloxy)methyl)cyclopentanecarboxylate (Compound 9i)

Adenine (compound 8, 236 mg, 1.745 mmoles) and compound 51 (276 mg, 0.5818 mmole) were dissolved in anhydrous N,N-dimethylformamide (5 mL) and cesium carbonate (569 mg, 1.745 mmoles) was added. The resulting mixture was stirred at 60 deg C. for 24 hours. After cooling to room temperature, the mixture was filtered and the filter cake was washed with ethyl acetate (20 mL). The filtrate was concentrated to dryness. The residue was purified on basic alumina (5% methanol in dichloromethane) giving compound 9i (100 mg, 32.6% yield) as a colorless liquid. (Mass (m/z): 530.5 (M+H)).

Example 81—Preparation of (1S,2R,4R)-4-(6-amino-9H-purin-9-yl)-N-(benzyloxy)-2-((tert-butyl-diphenylsilyloxy)methyl)cyclopentanecarboxamide (Compound 52i)

Compound 9i (100 mg, 0.188 mmole) and O-benzylhydroxylamine hydrochloride (60.4 mg, 0.377 mmole) were dissolved in anhydrous tetrahydrofuran and cooled to −78 deg C. under argon. Lithium hexamethyldisilazide (LiHMDS, 1.4M in tetrahydrofuran, 0.41 mL, 0.585 mmole) was slowly added and the resulting mixture was stirred at −78 deg C. for 2 hours. Upon completion, the reaction was quenched with saturated aqueous ammonium chloride solution (5 mL). The resulting mixture was washed with ethyl acetate (3×15 mL). The combined organic layers were dried over anhydrous sodium sulfate, filtered and concentrated to dryness. The residue was purified on basic alumina (6% methanol in dichloromethane) giving compound 52i (82 mg, 70% yield) as a pale yellow liquid. Mass (m/z): 621.4 (M+H).

Example 82—Preparation of (1S,2R,4R)-4-(6-amino-9H-purin-9-yl)-N-(benzyloxy)-2-(hydroxymethyl)cyclopentanecarboxamide (Compound 11i)

Compound 52i (82 mg, 0.132 mmole) was dissolved in tetrahydrofuran (4 mL) and cooled to 0 deg C. under argon. Tetrabutylammoniumfluoride (1M in tetrahydrofuran, 0.15 mL, 0.15 mmole) was slowly added and the resulting mixture was stirred at 0 deg C. for 30 minutes and at room temperature for an additional 90 minutes. Upon completion, the reaction was cooled to 0 deg C. and quenched with 50% saturated aqueous ammonium chloride solution (4 mL). After stirring at room temperature for 1 hour, the mixture was washed with ethyl acetate (3×10 mL). The combined organic phases were washed with brine (10 mL), dried over anhydrous sodium sulfate, filtered and concentrated to dryness. Crude compound 11i was isolated as a pale-yellow liquid and was used in the next reaction without purification. Mass (m/z): 383.3 (M+H).

Example 83—Preparation of (1S,2R,4R)-4-(6-amino-9H-purin-9-yl)-N-hydroxy-2-(hydroxymethyl)cyclopentanecarboxamide (Compound 10i)

Crude compound 11i (50 mg, 0.13 mmole) was dissolved in methanol (4 mL) and 20% palladium hydroxide on carbon (10 mg) was added. The resulting mixture was degassed under vacuum and stirred under a hydrogen atmosphere for 2 hours. Upon completion, the reaction was filtered through Celite and the Celite pad was washed with methanol (6 mL). The combined filtrates were concentrated to dryness. The residue was purified by preparative HPLC giving compound 10i as its TFA salt. The TFA salt was dissolved in methanol (1 mL) and MP-carbonate resin (50 mg) was added. After stirring at room temperature for 2 hours, the mixture was filtered and the filtrate was concentrated to dryness giving compound 10i free base (5 mg, 3.2% yield) as a brown solid. Mass (m/z): 293.3 (M+H).

Examples 84-87—Preparation of Compounds 10a and 10b

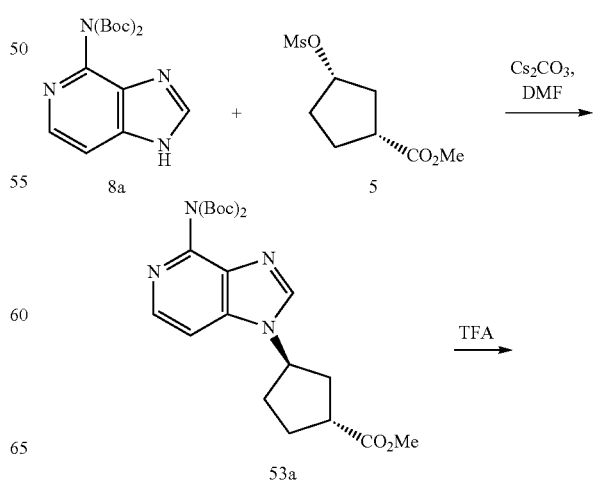

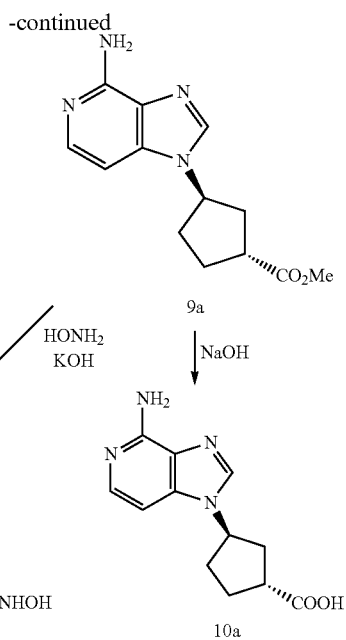

Example 84—Preparation of (1R,3R)-methyl 3-(4-(bis(tert-butoxycarbonyl)amino)-1H-imidazo[4,5-c]pyridin-1-yl)cyclopentanecarboxylate (Compound 53a)

Compound 8a (460 mg, 1.37 mmoles) and compound 5 (611 mg, 2.75 mmoles) were dissolved in anhydrous N,N-dimethylformamide (7 mL) and cesium carbonate (900 mg, 2.75 mmoles) was added. The resulting mixture was stirred at 50 deg C. for 2 days. After cooling to room temperature, the mixture was filtered and concentrated to dryness. The residue was purified on basic alumina (50% ethyl acetate in hexane) giving compound 53a (75 mg, 12% yield) as an off-white solid. $^1$HNMR (500 MHz, DMSO-d$_6$) δ ppm: 8.38 (d, 1H), 7.99 (s, 1H), 7.38 (d, 1H), 4.85 (m, 1H), 3.75 (s, 3H), 3.23 (m, 1H), 2.62 (m, 1H), 2.42 (m, 1H), 2.38-2.20 (m, 4H), 1.38 (s, 18H); Mass (m/z): 461.5 (M+H).

Example 85—Preparation of (1R,3R)-methyl 3-(4-amino-1H-imidazo[4,5-c]pyridin-1-yl)cyclopentanecarboxylate (Compound 9a)

Compound 53a (800 mg, 1.37 mmoles) was dissolved in anhydrous dichloromethane (15 mL). Trifluoroacetic acid (3 mL) was added dropwise and the resulting mixture was stirred at room temperature for 2 hours. Upon completion, the reaction mixture was concentrated to dryness. The residue was purified on basic alumina (3% methanol in dichloromethane) giving compound 9a (303 mg, 85% yield) as a colorless liquid. $^1$HNMR (500 MHz, DMSO-d$_6$) δ ppm: 8.2 (s, 1H), 7.65 (d, 1H), 6.8 (m, 1H), 6.2 (brs, 2H), 4.45 (m, 1H), 3.65 (s, 3H), 3.6 (m, 1H), 3.2 (m, 1H), 2.4 (m, 1H), 2.2 (m, 3H), 1.9 (m, 1H); Mass (m/z): 261.4 (M+H).

Example 86—Preparation of (1R,3R)-3-(4-amino-1H-imidazo[4,5-c]pyridin-1-yl)cyclopentanecarboxylic acid (Compound 10a)

Compound 9a (150 mg, 0.3937 mmole) was dissolved in methanol (3 mL) and aqueous sodium hydroxide solution (2M, 2 mL) was added. The reaction was stirred at room temperature for 1 hour. Upon completion, the reaction mixture was concentrated to dryness. The residue was purified by preparative HPLC giving compound 10a (30 mg, 21.14% yield) as an off-white solid. $^1$HNMR (500 MHz, DMSO-d$_6$) □ ppm: 13.4 (brs, 1H), 8.61 (s, 1H), 8.53 (brs, 2H), 7.75 (d, 1H), 7.31 (d, 1H), 5.0 (m, 1H), 3.16 (m. 1H), 2.42 (m, 1H), 2.35-2.10 (m, 3H), 2.12-1.95 (m, 1H), 1.95-1.82 (m, 1H); Mass (m/z): 247.5 (M+H).

Example 87—Preparation of (1R,3R)-3-(4-amino-1H-imidazo[4,5-c]pyridin-1-yl)-N-hydroxycyclopentanecarboxamide (Compound 10b)

Compound 9a (70 mg, 0.269 mmole) was dissolved in methanol (3 mL). Potassium hydroxide (1.46 g) was dissolved in methanol (7 mL). Hydroxylamine hydrochloride (1.15 g) was dissolved in methanol (10.5 mL). The potassium hydroxide solution was added to the hydroxylamine hydrochloride solution and the resulting mixture was stirred at 0 deg C. for 2 hours and then filtered. The hydroxylamine solution (4.22 mL of a 0.95M solution in MeOH, 4.013 mmoles) was slowly added to the compound 9a solution. The reaction was stirred at room temperature for 4 hours, after which it was concentrated to dryness. The residue was purified by preparative HPLC. Collected fractions were lyophilized. The residue was dissolved in methanol (3 mL) and treated with MP-carbonate resin (100 mg). After stirring for 2.5 hours, the resin was filtered and the filtrate was concentrated to dryness giving compound 10b (35 mg, 50% yield) as a white solid. $^1$HNMR (500 MHz, DMSO-d$_6$) δ ppm: 10.43 (brs, 1H), 8.27 (s, 1H), 7.75 (d, 1H), 6.84 (d, 1H), 6.44 (brs, 2H), 4.45 (m, 1H), 3.82 (m, 1H), 2.31 (m, 2H), 2.1 (m, 4H); Mass (m/z): 262.4 (M+H).

Examples 88-93—Preparation of Compounds 10c and 10d

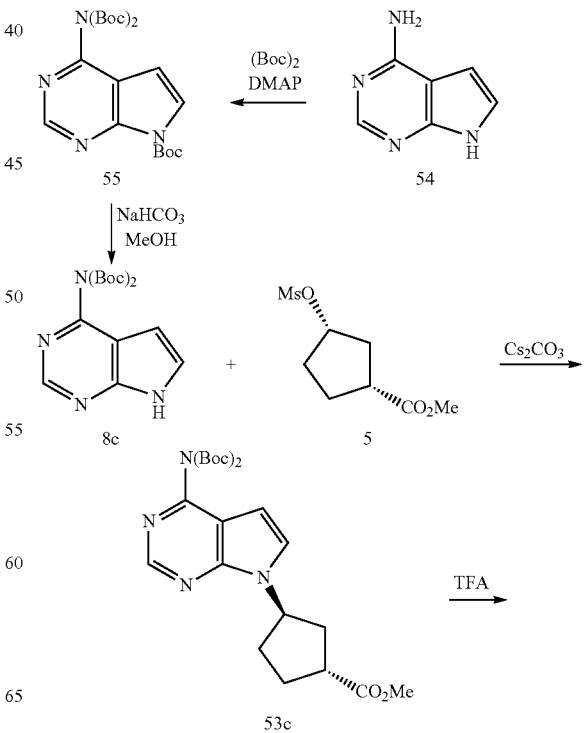

-continued

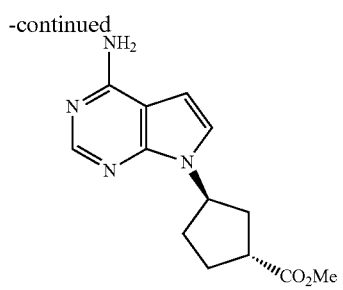

9c

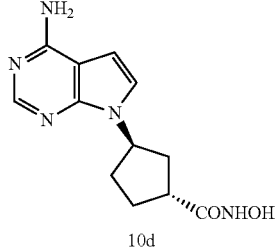

10d            10c

Example 88—Preparation of tert-butyl 4-(bis(tert-butoxycarbonyl)amino)-7H-pyrrolo[2,3-d]pyrimidine-7-carboxylate (Compound 55)

Compound 54 (1.9 g, 14.1 mmoles) was dissolved in anhydrous tetrahydrofuran (40 mL) and cooled to 0 deg C. DMAP (7 g, 56 mmoles) was added followed by di-tert-butyl dicarbonate (10.65 g, 49 mmoles). The reaction was stirred at room temperature for 24 hours, after which it was concentrated to dryness. The residue was dissolved in ethyl acetate (50 mL) and washed with saturated aqueous potassium bisulfate solution (2×25 mL). The organic phase was dried over anhydrous sodium sulfate, filtered and concentrated to dryness. The residue was purified on silica gel (10% ethyl acetate in hexane) giving compound 55 (3.49 g, 75% yield) as a pale yellow solid. $^1$HNMR (500 MHz, CDCl$_3$) δ ppm: 8.41 (m, 2H), 7.83 (d, 1H), 1.65 (s, 9H), 1.38 (s, 18H); Mass (m/z): 435.2 (M+H).

Example 89—Preparation of 4-(bis(tert-butoxycarbonyl)amino)-7H-pyrrolo[2,3-d]pyrimidine (Compound 8c)

Compound 55 (2.9 g, 4.6 mmoles) was dissolved in methanol (60 mL) and saturated aqueous sodium bicarbonate solution (4.6 mL) was added. The reaction was stirred at room temperature for 2 hours. Upon completion, the reaction was concentrated and the resulting aqueous residue was partitioned between chloroform (50 mL) and water (25 mL). The layers were separated and the organic phase was dried over anhydrous sodium sulfate, filtered and concentrated to dryness. The residue was triturated with hexane (20 mL), filtered and dried under vacuum giving compound 8c (800 mg, 52% yield) as an off-white solid. $^1$HNMR (500 MHz, CDCl$_3$) δ ppm: 8.31 (m, 2H), 7.96 (d, 1H), 7.38 (brs, NH), 1.38 (s, 18H); Mass (m/z): 335.2 (M+H).

Example 90—Preparation of (1R,3R)-methyl 3-(4-(bis(tert-butoxycarbonyl)amino)-7H-pyrrolo[2,3-d]pyrimidin-7-yl)cyclopentanecarboxylate (Compound 53c)

Compound 8c (500 mg, 1.49 mmoles) and compound 5 (398 mg, 1.79 mmoles) were dissolved in anhydrous N,N-dimethylformamide (15 mL) and cesium carbonate (487 mg, 1.49 mmoles) was added. The resulting mixture was stirred at 50 deg C. for 15 hours. After cooling to room temperature, the mixture was filtered and concentrated to dryness. The residue was purified on basic alumina (3% methanol in dichloromethane) giving compound 8c (206 mg, 30% yield) as an off-white solid. Mass (m/z): 461.4 (M+H).

Example 91—Preparation of (1R,3R)-methyl 3-(4-amino-7H-pyrrolo[2,3-d]pyrimidin-7-yl)cyclopentanecarboxylate (Compound 9c)

Compound 53c (200 mg, 0.4343 mmole) was suspended in anhydrous dichloromethane (5 mL) and trifluoroacetic acid (1 mL) was added dropwise. The mixture was stirred at room temperature for 2 hours after which, it was concentrated to dryness. The residue was purified on basic alumina (3% methanol in dichloromethane) giving compound 9c (85 mg, 75% yield) as a pale yellow solid. $^1$HNMR (500 MHz, DMSO-d$_6$) δ ppm: 8.12 (s, 1H), 7.25 (s, 1H), 6.95 (brs, 2H), 6.55 (d, 1H), 5.55 (m, 1H), 3.65 (s, 3H), 3.22 (m, 1H), 2.32 (m, 1H), 2.22 (m, 3H), 1.95 (m, 1H), 1.82 (m, 1H); Mass (m/z): 261.4 (M+H).

Example 92—Preparation of (1R,3R)-3-(4-amino-7H-pyrrolo[2,3-d]pyrimidin-7-yl)cyclopentanecarboxylic acid (Compound 10c)

Compound 9c (80 mg, 0.307 mmole) was dissolved in methanol (3 mL) and aqueous sodium hydroxide solution (2 M, 2 mL) was added. The reaction was stirred at room temperature for 1 hours after which, it was concentrated to dryness. The residue was purified by preparative HPLC giving compound 10c (30 mg, 39.7% yield) as an off-white solid. $^1$HNMR (500 MHz, DMSO-d$_6$) ☐ ppm: 9.54 (brs, 1H), 8.55 (brs, 1H), 8.45 (s, 1H), 7.55 (s, 1H), 7.03 (s, 1H), 5.10 (m, 1H), 3.06 (m. 1H), 2.42 (m, 1H), 2.22-1.80 (m, 5H), Mass (m/z): 247.4 (M+H).

Example 93—Preparation of (1R,3R)-3-(4-amino-7H-pyrrolo[2,3-d]pyrimidin-7-yl)-N-hydroxycyclopentanecarboxamide (Compound 10d)

Compound 9c (150 mg, 0.538 mmole) was dissolved in methanol (3 mL). Potassium hydroxide (1.46 g) was dissolved in methanol (7 mL). Hydroxylamine hydrochloride (1.15 g) was dissolved in methanol (10.5 mL). The potassium hydroxide solution was added to the hydroxylamine hydrochloride solution and the resulting mixture was stirred at 0 deg C. for 2 hours and then filtered. The hydroxylamine solution (4.08 mL of a 0.95M solution in MeOH, 4.013 mmoles) was slowly added to the compound 9c solution. The reaction was stirred at room temperature for 4 hours, after which it was concentrated to dryness. The residue was purified by preparative HPLC. Collected fractions were lyophilized. The residue was dissolved in methanol (5 mL) and treated with MP-carbonate resin (200 mg). After stirring for 2 hours, the resin was filtered and the filtrate was concentrated to dryness giving compound 10d (54 mg, 36% yield) as an off-white solid. $^1$HNMR (500 MHz, DMSO-d$_6$) δ ppm: 10.5 (brs, 1H), 8.7 (brs, 1H), 8.04 (s, 1H), 7.22 (s, 1H), 6.95 (brs, 2H), 6.52 (s, 1H), 5.05 (m, 1H), 2.828 (m, 1H), 2.22-1.82 (m, 6H); Mass (m/z): 262.5 (M+H).

Examples 94-101—Preparation of Compounds 10e and 10f

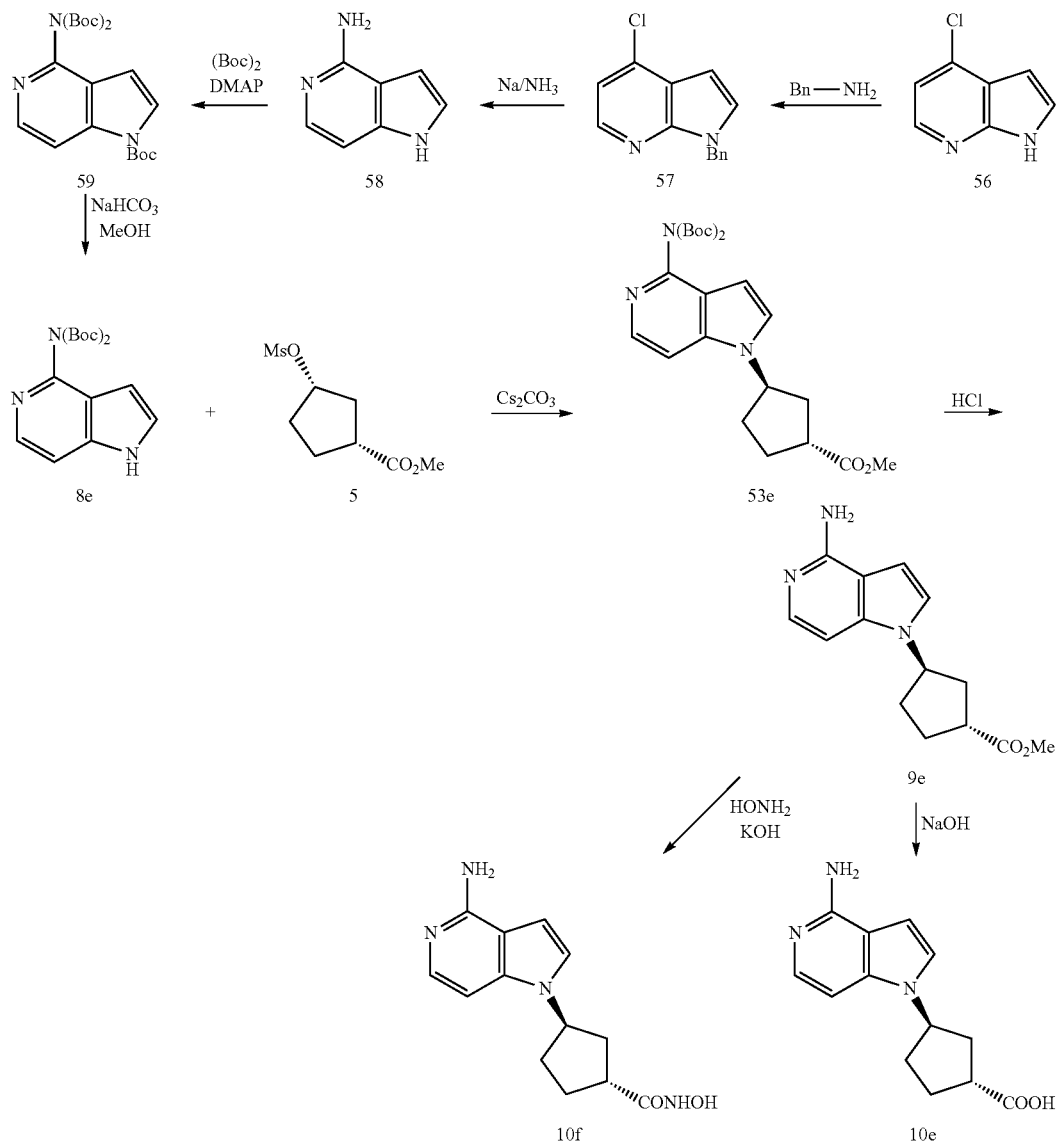

Example 94—Preparation of 1-benzyl-1H-pyrrolo [3,2-c] pyridin-4-amine (Compound 57)

Compound 56 (1 g, 6.54 mmoles) and benzylamine (3.6 mL, 32.67 mmoles) were combined in a sealed tube and heated to 175 deg C. for 8 hours. Upon completion, the reaction mixture was dissolved in methanol (15 mL) and then concentrated to dryness. The residue was purified by preparative HPLC. Collected fractions were lyophilized and the isolated residue was dissolved in a mixture of 10% methanol in dichloromethane (10 mL). The resulting mixture was made basic on addition of solid sodium carbonate (200 mg). The remaining solids were filtered and washed with 10% methanol in dichloromethane (5 mL). The combined filtrates were concentrated to dryness giving compound 57 (245 mg, 17% yield) as an off-white solid. $^1$HNMR (500 MHz, CDCl$_3$) δ ppm: 7.4-7.3 (m, 5H), 4.6-4.5 (s, 2H), 4.4-4.3 (m, 1H), 3.7 (s, 3H), 3.55 (d, 2H), 2.95-2.85 (m, 1H), 2.8-2.7 (m, 1H), 2.65-2.55 (m, 1H), 2.45-2.35 (m, 1H), 2.3-2.2 (m, 1H), 2.15-2.1 (m, 1H); Mass (m/z): 224.2 (M+H)

Example 95—Preparation of 1H-pyrrolo [3,2-c] pyridin-4-amine (Compound 58)

Compound 57 (1.4 g, 6.27 mmoles) was dissolved in anhydrous tetrahydrofuran (20 mL) and cooled to −78 deg C. under argon. Liquid ammonia (50 mL) was added followed by sodium metal (1.4 g, 62.7 mmoles). The blue color of the reaction mixture was noted. Upon completion, the reaction was quenched with solid ammonium chloride (5 g) and allowed to warm to room temperature. The resulting material was partitioned between aqueous sodium bicarbonate solution (10%, 25 mL) and ethyl acetate (50 mL). The layers were separated. The organic phase was dried over anhydrous sodium sulfate, filtered and concentrated to dryness giving compound 58 (416 mg, 50% yield) as a brown liquid. Mass (m/z): 134.6 (M+H).

Example 96—Preparation of tert-butyl 4-(bis (tert-butoxycarbonyl) amino)-1H-pyrrolo [3,2-c]pyridine-1-carboxylate (Compound 59)

Under nitrogen, compound 58 (1.2 g, 9.02 mmoles) was dissolved in a mixture of acetonitrile (10 mL) and dichloromethane (20 mL) at room temperature. DMAP (4.4 g, 36 mmoles) was added and the mixture was cooled to 0 deg C. After stirring at 0 deg C. for 30 minutes, di-tert-butyl dicarbonate (8.6 mL, 35.7 mmoles) was added. The reaction was stirred at room temperature for 24 hours after which, it was concentrated to dryness. The residue was diluted with ethyl acetate (50 mL) and washed with saturated aqueous potassium bisulfate solution (25 mL). The layers were separated and the organic phase was dried over anhydrous sodium sulfate, filtered and concentrated to dryness. The residue was purified on silica gel (10% ethyl acetate in hexane) giving compound 59 (2.73 g, 70% yield). $^1$HNMR (500 MHz, CDCl$_3$) δ ppm: 8.41 (m, 1H), 7.93 (d, 1H), 7.65 (d, 1H), 6.5 (d, 1H), 1.65 (s, 9H), 1.38 (s, 18H); Mass (m/z): 434.5 (M+H).

Example 97—Preparation of 4-(bis (tert-butoxycarbonyl) amino)-1H-pyrrolo [3,2-c] pyridine (Compound 8e)

Compound 59 (2 g, 4.6 mmoles) was dissolved in methanol (60 mL) and saturated aqueous sodium bicarbonate solution (4 mL) was added. The resulting mixture was stirred at room temperature for 2 days after which, the reaction was concentrated to remove the methanol. The aqueous residue was partitioned between chloroform (50 mL) and water (25 mL). The layers were separated and the organic phase was dried over anhydrous sodium sulfate, filtered and concentrated to dryness. The resulting crude compound 8e (1.2 g, 80% yield) was used without further purification. $^1$HNMR (500 MHz, CDCl$_3$) δ ppm: 9.2 (brs, 1H), 8.18 (d, 2H), 7.25 (m, 1H), 6.5 (d, 1H), 1.38 (s, 18H); Mass (m/z): 334.4 (M+H).

Example 98—Preparation of (1R,3R)-methyl 3-(4-(bis(tert-butoxycarbonyl)amino)-1H-imidazo[4,5-c] pyridin-1-yl)cyclopentanecarboxylate (Compound 53e)

Compound 8e (460 mg, 1.37 mmoles) and compound 5 (611 mg, 2.75 mmoles) were dissolved in anhydrous N,N-dimethylformamide (7 mL) and cesium carbonate (900 mg, 2.75 mmoles) was added. The resulting mixture was stirred at 50 deg C. for 16 hours. Upon completion, the reaction was cooled to room temperature, filtered and concentrated to dryness. The residue was purified on silica gel (50% ethyl acetate in hexane) giving compound 53e (170 mg, 26.9%) as an off-white solid. $^1$HNMR (500 MHz, DMSO-d$_6$) δ ppm: 8.38 (d, 1H), 7.99 (s, 1H), 7.38 (d, 1H), 4.85 (m, 1H), 3.75 (s, 3H), 3.23 (m, 1H), 2.62 (m, 1H), 2.42 (m, 1H), 2.38-2.20 (m, 4H), 1.38 (s, 18H); Mass (m/z): 461.5 (M+H).

Example 99—Preparation of (1R,3R)-methyl 3-(4-amino-1H-imidazo[4,5-c]pyridin-1-yl)cyclopentanecarboxylate (Compound 9e)

Compound 53e (250 mg, 0.543 mmole) was suspended in ethyl acetate (2 mL) and a solution of hydrochloric acid in ethyl acetate (2M, 2 mL) was added dropwise. The reaction was stirred at room temperature for 2 hours after which, it was concentrated to dryness. The residue was purified by preparative HPLC. Lyophilization of the collected fractions gave compound 9e (28 mg, 20% yield) as an off-white solid. $^1$HNMR (500 MHz, DMSO-d$_6$) δ ppm: 7.6 (m, 1H), 7.38 (m, 1H), 7.2 (brs, 2H), 6.95 (m, 1H), 6.8 (m, 1H) 4.82 (m, 1H), 3.60 (s, 3H), 3.42 (m, 1H), 2.2-1.85 (m, 6H); Mass (m/z): 260.5 (M+H).

Example 100—Preparation of (1R,3R)-3-(4-amino-1H-pyrrolo[3,2-c]pyridin-1-yl)cyclopentanecarboxylic acid (Compound 10e)

Compound 9e (80 mg, 0.308 mmole) was dissolved in methanol (3 mL) and an aqueous sodium hydroxide solution (2M, 2 mL) was added. The reaction was stirred at room temperature for 1 hour after which, it was concentrated to dryness. The residue was purified by preparative HPLC. Collected fractions were lyophilized giving compound 10e (25 mg, 33% yield) as an off-white solid. $^1$HNMR (500 MHz, DMSO-d$_6$) δ ppm: 12.5 (brs, 1H), 8.2 (brs, 2H), 7.72-7.52 (m, 2H), 7.2 (d, 1H), 7.05 (d, 1H), 5.00 (m, 1H), 3.10 (m, 1H), 2.1 (m, 2H), 1.9 (m, 2H). Mass (m/z): 246.5 (M+H).

Example 101—Preparation of (1R,3R)-3-(4-amino-1H-imidazo[4,5-c]pyridin-1-yl)-N-hydroxycyclopentanecarboxamide (Compound 10f)

Compound 9e (80 mg, 0.308 mmole) was dissolved in methanol (3 mL). Potassium hydroxide (1.46 g) was dissolved in methanol (7 mL). Hydroxylamine hydrochloride (1.15 g) was dissolved in methanol (10.5 mL). The potassium hydroxide solution was added to the hydroxylamine hydrochloride solution and the resulting mixture was stirred at 0 deg C. for 2 hours and then filtered. The hydroxylamine solution (2.4 mL of a 0.95M solution in MeOH, 2.283 mmoles) was slowly added to the compound 9e solution. The reaction was stirred at room temperature for 4 hours, after which it was concentrated to dryness. The residue was purified by preparative HPLC. Collected fractions were lyophilized. The residue was dissolved in methanol (5 mL) and treated with MP-carbonate resin (150 mg). After stirring for 2 hours, the resin was filtered and the filtrate was concentrated to dryness giving compound 10f (30 mg, 37.5% yield) as a white solid. $^1$HNMR (500 MHz, DMSO-d$_6$) δ ppm: 10.5 (brs, 1H), 8.7 (brs, 1H), 7.55 (d, 1H), 7.40 (m, 1H), 6.62 (m, 2H), 6.0 (brs, 2H), 4.70 (m, 1H), 2.70 (m, 1H) 2.40-1.80 (m, 6H); Mass (m/z): 261.5 (M+H).

Example 102—Preparation of Compound 10

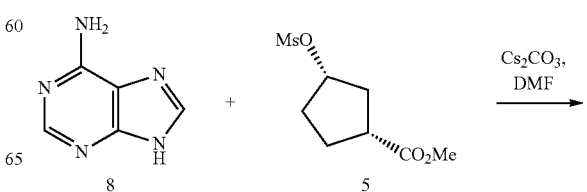

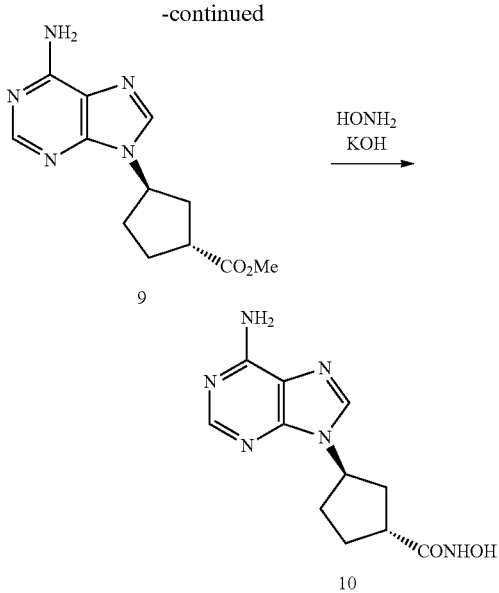

Example 102—Preparation of (1R,3R)-3-(6-amino-9H-purin-9-yl)-N-hydroxycyclopentanecarboxamide (Compound 10)

Compound 10 was prepared from compound 5 and compound 8 according to example 8 and example 9. Analytical data were consistent with data published in Levy, et al., J Med. Chem. 2003, 46, 2177-2186.

Examples 103-107—Biological Evaluation of Adenylyl Cyclase Inhibitors

Example 103—General Description of Assays

Compounds were assayed for their ability to attenuate cyclic AMP (cAMP) production in cardiomyocyte membrane preparations isolated from transgenic mice. Transgenic mice were separately bred to overproduce type V adenylyl cyclase, type VI adenylyl cyclase and type II adenylyl cyclase. cAMP levels were determined using a Cyclic AMP Competitive ELISA kit purchased from ThermoFischer Scientific (Cat# EMSCAMPL).

Example 104—Protocol for Generation of Membrane Preparations from Transgenic Mouse Heart Tissue Buffer A (pH 8) was prepared comprising final concentrations of the following: 50 mM Tris, 1 mM EGTA, 1 mM EDTA, 1 mM DTT, 100 mM sucrose, 20 µg/mL TPCK (protease inhibitor), 20 µg/mL TLCK (protease inhibitor), 1 mM PMSF (protease inhibitor), 10 µg/mL leupeptin (protease inhibitor) and 10 µg/mL aprotinin (protease inhibitor).

Buffer B (pH 8) was prepared comprising final concentrations of the following: 50 mM Tris, 1 mM EDTA, 100 mM sucrose, 0.2 mM PMSF (protease inhibitor), 2 µg/mL leupeptin (protease inhibitor) and 2 µg/mL aprotinin (protease inhibitor).

Hearts were surgically excised from transgenic mice. Each isolated heart was treated with 3-4 mL of buffer A and cooled to 0 deg C. for 5 minutes. Treated hearts were homogenized for 10 seconds using a Polytron homogenizer cooled to 0 deg C. and set to speed 6. Homogenized hearts were centrifuged at 500×g at 4 deg C. for 10 minutes. Supernatants were transferred to ultracentrifuge tubes and centrifuged at 35,000 rpm at 4 deg C. for 40 minutes. Isolated pellets were combined with buffer B (500 µL) and sonicated to a suspension. Protein concentration was determined using a commercial Bradford assay kit. Membrane preparations were stored at −80 deg C.

Example 105—Protocol for Adenylyl Cyclase Membrane Assay

Buffer R (pH 8) was prepared comprising final concentrations in water of the following: HEPES (20 mM), magnesium chloride (5 mM), EDTA (0.5 mM), ATP (0.1 mM), phospho creatinine (1 mM), creatinine phosphokinase (8 units/mL), IBMX (200 µM), forskolin (50 µM) or control (DMSO in water).

Inhibitor solutions were prepared by dilution of stock solutions of inhibitors (10 mM in DMSO) to a final concentration of 100 µM in water. Serial dilutions with water were subsequently made in order to determine IC50 values.

Reaction mixtures were prepared comprising buffer R (10 µL), inhibitor or control (10 µL), and water (75 µL).

A reaction mixture was pre-incubated at 30 deg C. for 5 minutes. A membrane preparation (e.g. 5 µL for type V Adenylyl Cyclase comprising 2 µg of membrane protein per 5 µL of preparation) was added and the mixture was incubated at 30 deg C. for 15 minutes. The reaction was stopped by addition of 0.1 M hydrochloric acid (100 µL) and cooled to 0 deg C. The resulting mixture was incubated at 0 deg C. for 60 minutes. The cAMP concentration of the supernatant was measured using a Cyclic AMP Competitive ELISA kit purchased from ThermoFischer Scientific.

Example 106—Protocol for Adenylyl Cyclase Cell-Based Assay

H9c2(2-1) myoblast cell line was obtained from ATCC (CRL-1446). Cells ($10^5$ cells/mL) were seeded in 24-well plates at $5 \times 10^4$ cells per well. Cells were allowed to attach over 24 hours. The cells were then washed with PBS. Serum-free DMEM supplemented with 20 mM HEPES and 0.5 mM IBMX was added and the cells were incubated at 37 deg C. for 20 minutes. An Adenylyl Cyclase inhibitor (0.001-100 µM in DMSO/water with DMSO concentration <1%) was added and the mixture was incubated at 37 deg C. for 10 minutes. Forskolin (50 µM in DMSO/water with DMSO concentration <1%) was added and the mixture was incubated at 37 deg C. for 10 minutes. As an alternative to forskolin, isoproterenol (5 mM in DMSO/water with DMSO concentration <1%) was added and the mixture was incubated at 37 deg C. for 15 minutes. The media was removed and the cells were lysed by addition of 0.1 M hydrochloric acid (200 µL) 0 deg C. Lysed mixtures were maintained at 0 deg C. for 10-20 minutes and the plates were then centrifuged at 3,000×g for 5 minutes. cAMP levels in the supernatant were measured using the ThermoScientific cAMP competitive ELISA (EMSCAMPL) kit with samples acetylated in glass or polypropylene tubes.

Example 107—Results for Adenylyl Cyclase Membrane Assays and Adenylyl Cyclase Cell-Based Assays Adenylyl cyclase inhibitors were assayed as described in Example 105 and Example 106. The results for all assayed compounds are illustrated in the following table:

| Cmpd ID | Structure | Membrane IC$_{50}$ (μM) | | | H9c2 Cell IC$_{50}$ (μM) | |
|---|---|---|---|---|---|---|
| | | Type V | Type VI | Type II | Forskolin | Isoproterenol |
| 10 | adenine-cyclopentyl-CONHOH | 0.15 | 0.25 | | 9.63 | 27 |
| 10a | imidazopyridine-cyclopentyl-COOH | >10.00 | | | | |
| 10b | imidazopyridine-cyclopentyl-CONHOH | 0.29 | | | 8.50 | |
| 10c | pyrrolopyrimidine-cyclopentyl-COOH | >100.00 | | | | |
| 10d | pyrrolopyrimidine-cyclopentyl-CONHOH | 0.98 | | | | |
| 10e | pyrrolopyridine-cyclopentyl-COOH | >10.00 | | | | |

-continued

| Cmpd ID | Structure | Membrane IC$_{50}$ (μM) | | | H9c2 Cell IC$_{50}$ (μM) | |
|---|---|---|---|---|---|---|
| | | Type V | Type VI | Type II | Forskolin | Isoproterenol |
| 10f | 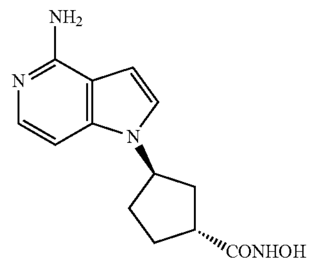 | >100.00 | | | | |
| 10g | 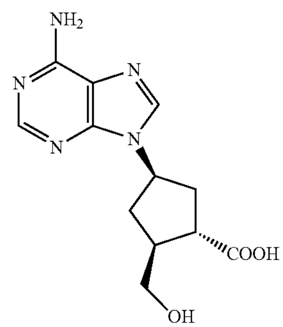 [SMILES: Nc1ncnc2c1ncn2[C@@H]1C[C@H](CO)[C@@H](C(=O)O)C1] | >100.00 | | | | |
| 10h | 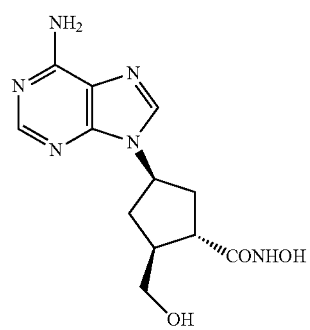 | 1.90 | | | 18.00 | |
| 10i | 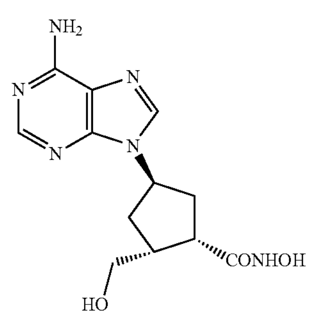 | 3.10 | | | | |
| 10j | 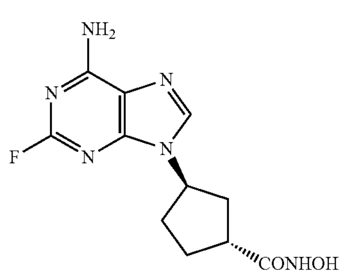 | 0.08 | 0.21 | 5.58 | 2.32 | 2.45 |

-continued

| Cmpd ID | Structure | Membrane IC$_{50}$ (μM) | | | H9c2 Cell IC$_{50}$ (μM) | |
|---|---|---|---|---|---|---|
| | | Type V | Type VI | Type II | Forskolin | Isoproterenol |
| 10k | | 4.89 | | | | |
| 10l | | 6.45 | | | | |
| 10m | | 3.50 | | | | |
| 10n | | >300 | | | | |
| 10o | | >300 | | | | |

-continued

| Cmpd ID | Structure | Membrane IC$_{50}$ (μM) | | | H9c2 Cell IC$_{50}$ (μM) | |
|---|---|---|---|---|---|---|
| | | Type V | Type VI | Type II | Forskolin | Isoproterenol |
| 10p | | >300 | | | | |
| 10q | | >300 | | | | |
| 10r | | >300 | | | | |
| 10s | | 0.51 | | | | |
| 10t | | 0.13 | | | | |

-continued

| Cmpd ID | Structure | Membrane IC$_{50}$ (μM) | | | H9c2 Cell IC$_{50}$ (μM) | |
| --- | --- | --- | --- | --- | --- | --- |
| | | Type V | Type VI | Type II | Forskolin | Isoproterenol |
| 10u | (structure) | 0.07 | | 13.4 | 0.94 | 2.44 |
| 10v | (structure) | 0.03 | 0.03 | 1.11 | 1.14 | 1.89 |

Example 108—Compound 10u Reduced Infarct Size and Limited Reperfusion Injury Mouse Ischemia and Reperfusion Model 3-4-month-old male CS7BL/6 mice purchased from Jackson Laboratory were anesthetized by an injection of 2% 2,2,2-tribromomethanol (0.66 mg/kg i.p.; Aldrich Chemical, St. Louis, Mo.). The mice were then orally intubated and mechanically ventilated. The heart was accessed via a thoracotomy at the fourth intercostals space and 7-0 silk suture passed under the left anterior descending coronary artery (LAD) at the point where it emerged from under the left atrial flap. Myocardial ischemia was achieved by occluding the LAD against a 22-gauge J-shaped stainless-steel probe and verified by visually noting the regional akinesis and blanching of the left ventricle. The chest was closed in layers, with the long end of the probe remaining outside the chest wall, allowing the animals to be removed from the ventilator. After 30 min. of ischemia, reperfusion was initiated by carefully pulling the probe out from the ligature and then removing it from the chest cavity. Following the surgical procedure, the mice were allowed to recover on a warmed surface, with supplemental oxygen delivered from a nose cone. I/R were verified by three lead electrocardiograms, which were obtained preoperatively, at the end of the ischemic interval and immediately after the initiation of reperfusion. Mice fully recovered from the surgical procedure were returned to standard animal housing conditions. The mice were under 24 hrs. of reperfusion followed by sacrifice and dual staining of the heart with TTC and Alcian Blue. Compounds of the invention were administered as an i.v. infusion at 0.06 mg/kg. Adenosine was used for comparison at the same dose.

Results:

The ability of the AC5 inhibitors of the invention to reduce infarct size after 30 min of Coronary Artery Occlusion (CAO) and 24 hr. of Coronary Artery Reperfusion (CAR) was examined in an animal model. In mice, left ventricle (LV) infarct size was lower when compounds 10 and 10u were delivered at CAR (20% and 22% respectively) compared to vehicle (33%) and adenosine (38%). Area at Risk (AAR) was the same in all groups (Illustrated in FIG. 3).

What is claimed is:

1. A compound of Formula I wherein,

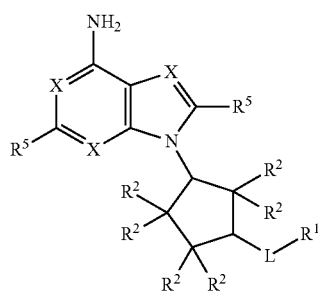

wherein,
$R^1$ is COOH, COOCH$_3$, CONH$_2$ or CONHOH;
Each $R^2$ is independently H, C$_1$-C$_6$ alkyl or —(CH$_2$)$_m$—R$^3$, wherein at least 3 R$^2$ groups must be H; or, independently of other R$^2$ groups, two R$^2$ groups residing on adjacent carbon atoms join to form a carbon-carbon double bond;
Each $R^3$ is independently OR$^4$, N(R$^4$)$_2$, SR$^4$, COOH, COOCH$_3$ or CONH$_2$;
Each $R^4$ is independently H or C$_1$-C$_6$ alkyl;
Each $R^5$ is independently F, Cl, Br, I, OH, OR$^6$, N(R$^6$)$_2$, SR$^6$, C$_1$-C$_6$ alkyl, CF$_3$, NO$_2$, COOH, COOCH$_3$, CONH$_2$, SO$_3$H, PO$_3$H or CN;
Each $R^6$ is independently H or C$_1$-C$_6$ alkyl;
$R^7$ is H or C$_1$-C$_6$ alkyl;
L is a direct link or —(CH$_2$)$_n$—Y—(CH$_2$)$_o$—;
Each X is independently N or CH;
Y is a direct link, O, S or NR$^7$;
m is an integer from 0 to 5;
n is an integer from 0 to 5;
o is an integer from 0 to 5, wherein if L is not a direct link, o is not 0;

Each stereogenic center is independently either R or S; and,
If all $R^2$ groups are H, at least one of $R^5$ is not H or at least one of X is not N.

2. A compound of claim 1 comprising a structure of Formula I

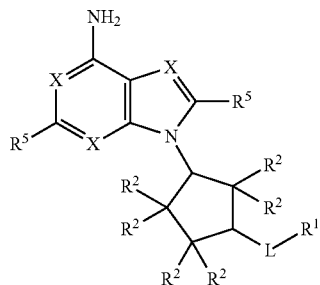

wherein,
$R^1$ is COOH or CONHOH;
Each $R^2$ is independently H, $C_1$-$C_6$ alkyl or —(CH$_2$)$_m$—$R^3$, wherein at least 3 $R^2$ groups must be H;
Each $R^3$ is $OR^4$;
Each $R^4$ is H;
Each $R^5$ is independently F, OH, $OR^6$, $N(R^6)_2$, $SR^6$, $C_1$-$C_6$ alkyl, $CF_3$, $NO_2$, COOH, $CONH_2$, or CN;
Each $R^6$ is H;
$R^7$ is H or $C_1$-$C_6$ alkyl;
L is a direct link or —(CH$_2$)$_n$—Y—(CH$_2$)$_o$—;
Each X is independently N or CH;
Y is a direct link, O or $NR^7$;
m is an integer from 0 to 3;
n is an integer from 0 to 3;
o is an integer from 0 to 3, wherein if L is not a direct link, o is not 0;
Each stereogenic center is independently either R or S; and,
If all $R^2$ groups are H, at least one of $R^5$ is not H or at least one of X is not N.

3. A compound of claim 1 comprising a structure of Formula I

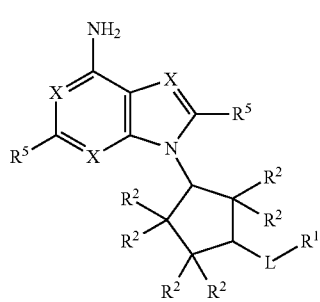

wherein,
$R^1$ is CONHOH;
Each $R^2$ is independently H, $C_1$-$C_6$ alkyl or —(CH$_2$)$_m$—$R^3$, wherein at least 3 $R^2$ groups must be H;
Each $R^3$ is $OR^4$;
Each $R^4$ is H;

Each $R^5$ is independently F, OH, $OR^6$, $N(R^6)_2$, $SR^6$, $C_1$-$C_6$ alkyl, $CF_3$, $NO_2$, COOH, $CONH_2$, or CN;
Each $R^6$ is H;
L is a direct link;
Each X is independently N or CH;
m is an integer from 0 to 3;
Each stereogenic center is independently either R or S; and,
If all $R^2$ groups are H, at least one of $R^5$ is not H or at least one of X is not N.

4. A compound of claim 1 comprising a structure of Formula I

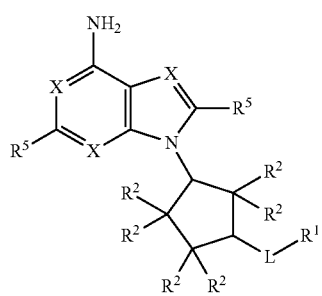

wherein, said structure of Formula I further comprises a pharmaceutically acceptable salt form.

5. A compound of claim 1 comprising a structure of Formula I

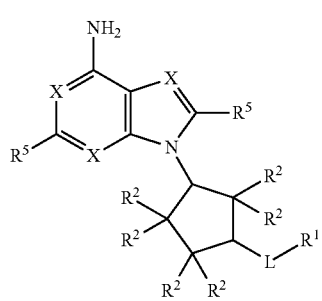

wherein, said structure of Formula I further comprises a pharmaceutically acceptable co-crystal form.

6. A method of preparing a compound of Formula I

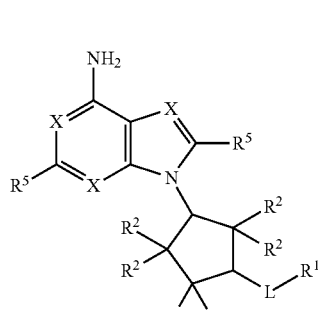

wherein,
$R^1$ is COOH, $COOCH_3$, $CONH_2$ or CONHOH;
Each $R^2$ is independently H, $C_1$-$C_6$ alkyl or —(CH$_2$)$_m$—$R^3$, wherein at least 3 $R^2$ groups must be H; or, independently of other $R^2$ groups, two $R^2$ groups residing on adjacent carbon atoms join to form a carbon-carbon double bond;

Each $R^3$ is independently $OR^4$, $N(R^4)_2$, $SR^4$, COOH, $COOCH_3$ or $CONH_2$;
Each $R^4$ is independently H or $C_1$-$C_6$ alkyl;
Each $R^5$ is independently F, Cl, Br, I, OH, $OR^6$, $N(R^6)_2$, $SR^6$, $C_1$-$C_6$ alkyl, $CF_3$, $NO_2$, COOH, $COOCH_3$, $CONH_2$ $SO_3H$, POSH or CN;
Each $R^6$ is independently H or $C_1$-$C_6$ alkyl;
$R^7$ is H or $C_1$-$C_6$ alkyl;
L is a direct link or —$(CH_2)_n$—Y—$(CH_2)_o$—;
Each X is independently N or CH;
Y is a direct link, O, S or $NR^7$;
m is an integer from 0 to 5;
n is an integer from 0 to 5;
o is an integer from 0 to 5, wherein if L is not a direct link, o is not 0;
Each stereogenic center is independently either R or S; and,
If all $R^2$ groups are H, at least one of $R^5$ is not H or at least one of X is not N;
Comprising the steps of:
(1) Reacting a compound of Formula II with a compound of Formula III

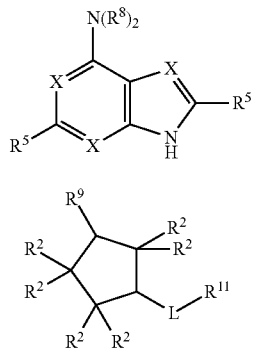

wherein, all substitutions are defined according to claim 1 and wherein,

Each $R^8$ is independently H or a suitable protecting group selected from the list comprising but not limited to Boc, Cbz, Fmoc, Teoc, benzyl and benzylidene;
$R^9$ is Cl, Br, I or $OR^{10}$;
$R^{10}$ is H, Methanesulfonyl, Trifluoromethanesulfonyl, Toluenesulfonyl or Nitrophenylsulfonyl;
$R^{11}$ is $COOR^{12}$; and,
$R^{12}$ is H or $C_1$-$C_6$ alkyl;
(2) Removing a protecting group if a protecting group is present;
(3) Converting a carboxylic acid or an ester to a hydroxamic acid.

7. A pharmaceutical composition comprising an effective amount of a compound of claim 1 or a pharmaceutically acceptable salt or co-crystal thereof, and a pharmaceutically acceptable diluent or carrier.

8. A method of treating a patient suffering from heart disease comprising administering an effective amount of a pharmaceutical composition of claim 6 to the patient in need thereof.

9. The method of claim 7, wherein the heart disease is congestive heart failure.

10. The method of claim 7, wherein the heart disease is acute myocardial infarction.

11. The method of claim 7, wherein the heart disease is acute coronary artery syndrome.

12. A method of reducing infarct size and/or limiting, decreasing and/or inhibiting coronary reperfusion injury in a patient suffering from a coronary ischemic injury said method comprising administering during or after reperfusion a pharmaceutically effective amount of compounds of claim 1 capable of inhibiting Adenylyl Cyclase Type V.

* * * * *